(12) United States Patent
Sugawara et al.

(10) Patent No.: US 8,222,429 B2
(45) Date of Patent: Jul. 17, 2012

(54) PHOTODISSOCIABLE PROTECTIVE GROUP

(75) Inventors: Kazuki Sugawara, Ikoma (JP); Yoshinori Gosyo, Ikoma (JP)

(73) Assignee: National University Corporation Nara Institute of Science and Technology, Ikoma-Shi (JP)

( * ) Notice: Subject to any disclaimer, the term of this patent is extended or adjusted under 35 U.S.C. 154(b) by 0 days.

(21) Appl. No.: 12/921,597

(22) PCT Filed: Jan. 8, 2009

(86) PCT No.: PCT/JP2009/050102
§ 371 (c)(1), (2), (4) Date: Sep. 9, 2010

(87) PCT Pub. No.: WO2009/113322
PCT Pub. Date: Sep. 17, 2009

(65) Prior Publication Data
US 2011/0028738 A1 Feb. 3, 2011

(30) Foreign Application Priority Data
Mar. 11, 2008 (JP) .................................. 2008-61795

(51) Int. Cl.
*C07D 335/06* (2006.01)
(52) U.S. Cl. ........................................................ 549/23
(58) Field of Classification Search ........................ None
See application file for complete search history.

(56) References Cited

FOREIGN PATENT DOCUMENTS

| JP | 11-029500 A | 2/1999 |
|---|---|---|
| JP | 2004-051624 A | 2/2004 |
| JP | 2008-214344 A | 9/2008 |

OTHER PUBLICATIONS

S. Kitani, "Thiochromone Kokkaku o Yusuru Shinki Hikari Kairisei Hogoki no Gosei to Kino (Synthesis and function of thiochromone skelton as New Photodissociable protective group)," Heisei 19 Nendo Hakase Ronbun Yoshishu, Nara Institute of Science and Technology Center for Industry-Government-Academia Collaboration, Jun. 9, 2008, pp. 31-32 and cover pages (4 sheets) and English translation thereof (3 pages).
K. Sugahara, "Peptide Gosei o Shiko shita Shinld. Hikari Kairisei Hogoki no Oyo Kenkyu (Investigation of New Photolablie protective group targeting for peptide synthesis)," Heisei 19 Nendo Shushi Ronbun Yoshishu, Nara Institute of Science and Technology Center for Industry-Government-Academia Collaboration, Feb. 15, 2008, pp. 105-106 and cover pages (4 sheets) and English translation thereof (3 pages).
Givens, R. S., et al., "Photochemistry of Phosphate Esters: An Efficient Method for the Generation of Electrophiles," J. Am. Chem. Soc., 106 (22), 1984, pp. 6860-6861.
Patchornik, A., et al., "Photosensitive Protecting Groups," J. Am. Chem. Soc., 92(21), 1970, pp. 6333-6335.
Kitani, S., et al., "Synthesis and characterization of thiochromone S,S-dioxides as new photolabile protecting groups," Chem. Commun., (18), 2008, pp. 2103-2105.
G. Mayer, et al., "Biologically Active Molecules with a "Light Switch"," Angew. Chem. Int. Ed., 2006, 45, pp. 4900-4921.
S.P.A. Fodor et al., "Light-Directed, Spatially Addressable Parallel Chemical Synthesis,"; Science, 1991, 251, pp. 767-773.
International Search Report dated Mar. 10, 2009, issued for PCT/JP2009/050102.

*Primary Examiner* — Janet Andres
*Assistant Examiner* — Timothy R Rozof
(74) *Attorney, Agent, or Firm* — Edwards Wildman Palmer LLP; James E. Armstrong, IV; Junko Harada

(57) ABSTRACT

The present invention provides a photolabile protecting group that can be removed by light irradiation under mild conditions. More specifically, the present invention provides a method comprising protecting a reactive functional group (e.g., a hydroxyl group, amino group, carboxyl group, carbonyl group, phosphodiester group, etc.) by the photolabile protecting group, and then removing the photolabile protecting group simply by light irradiation under neutral conditions. The present invention relates to a compound represented by Formula (3):

(3)

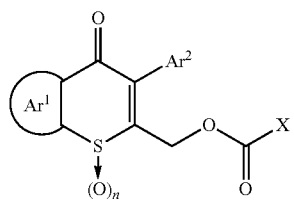

wherein $Ar^1$ is an optionally substituted aromatic or heteroaromatic ring, $Ar^2$ is an optionally substituted aryl or heteroaryl group, X is a leaving group, and n is an integer of 1 or 2; and a method of protecting and deprotecting an amino group etc. using the compound.

3 Claims, 2 Drawing Sheets

PHOTODISSOCIABLE PROTECTIVE GROUP

TECHNICAL FIELD

The present invention relates to a photolabile protecting group, and a method of protecting and deprotecting a functional group using the protecting group.

BACKGROUND ART

In the field of synthetic organic chemistry, protection and deprotection reactions of reactive functional groups (e.g., hydroxyl groups, amino groups, carboxyl groups, carbonyl groups, phosphodiester groups, etc.) are essential particularly for the construction of complex molecules. However, such deprotection reactions necessitate further addition of reagents, which may result in the degradation of compounds and the production of by-products.

Against this background, photolabile protecting groups that allow deprotection of reactive functional groups under neutral conditions have recently attracted attention (e.g., Non-Patent Document 1). Since photolabile protecting groups do not necessitate further addition of reagents and can be removed by light irradiation under neutral conditions, they are also applicable to acid- or base-sensitive compounds. Therefore, photolabile protecting groups have a great deal of potential as protecting groups in organic synthesis.

Moreover, since photolabile protecting groups can be eliminated by light, the size of the reaction field can be reduced to a nanoscale level. For example, in 1991, Fordor et al. successfully synthesized a DNA microarray using a photolabile protecting group by merging combinatorial chemistry with technology of photolithography for semiconductor production (Non-Patent Document 2).

Moreover, a caged compound, which is a biologically active molecule protected by a photodegradable protecting group, allowing the molecule to temporarily lose its activity, is made present in a cell, and the molecule is irradiated with light to become a bioactive substance, which can induce biological reactions. Using this technique, the time and place in which signal molecules express their functions can be controlled by the time and place in which light is irradiated; additionally, the expression level can theoretically be controlled by the amount of irradiating light. Therefore, a powerful method of real-time control of the space-time kinetics of molecules involved in signal transfer can be achieved.

Along with the development of microarrays and caged compounds described above, photolabile protecting groups that can easily be removed by light irradiation have been actively developed in recent years. Specific examples thereof are shown below. Examples of compounds currently often used in microarrays or caged compounds include nitrobenzyl derivatives represented by Formula (A) (Non-Patent Document 3) and coumarin derivatives represented by Formula (B) (Non-Patent Document 4).

[Chem. 1]

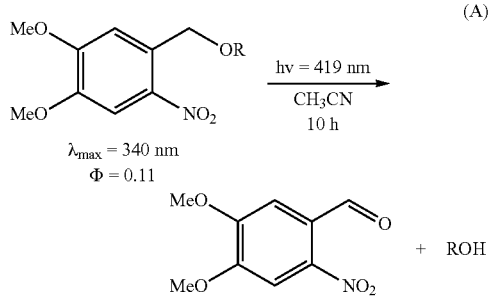

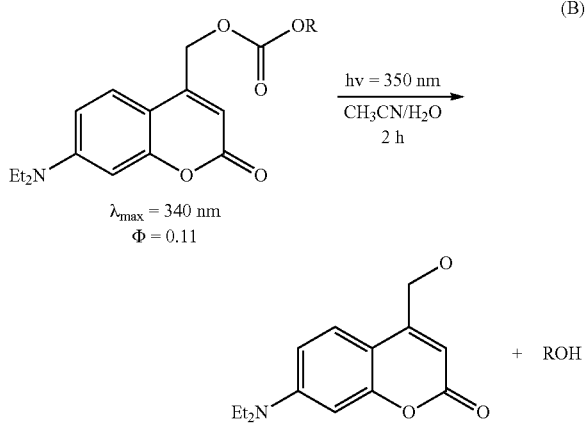

These compounds almost quantitatively release alcohol upon light irradiation; however, almost no compounds that allow simple quantitative determination of deprotection are known. For example, Patent Document 1 indicates that a protecting group that has an o-aminocinnamic acid skeleton is removed from a bioactive substance by light irradiation, thereby generating a carbostyryl derivative with strong fluorescence, and that the deprotected free bioactive substance can be quantified by measuring the fluorescence intensity.

If photolabile protecting groups that facilitate the protection and deprotection of not only the hydroxyl groups and amino groups described above, but also other reactive functional groups (e.g., carboxyl groups, carbonyl groups, phosphodiester groups, etc.) are developed, such photolabile protecting groups will be very useful in the fields of organic chemistry and photochemistry, as well as biology, and have the potential of being used in a wide application.

Patent Document 1: Japanese Unexamined Patent Publication No. 1999-29500

Non-Patent Document 1: G. Mayer, A. Heckel, Angew. Chem. Int. Ed., 2006, 45, 4900

Non-Patent Document 2: Fodor, S. P. A.; Read, J. L.; Pirrung, M. C.; Stryer, L. T.; Lu, A.; Solas, D.; Science, 1991, 251, 767-773.

Non-Patent Document 3: Patchornik, A., Amit, B., and Woodward, R. B. J. Am. Chem. Soc. 1970, 92, 6333

Non-Patent Document 4: Givens, R. S. and Matuszewski, B. J. Am. Chem. Soc. 1984, 92, 6860.

DISCLOSURE OF THE INVENTION

Problems to be Solved by the Invention

An object of the present invention is to provide a photolabile protecting group that can be eliminated by light irradiation under mild conditions, and more specifically to provide a method of protecting reactive functional groups (e.g., hydroxyl groups, amino groups, carboxyl groups, carbonyl groups, phosphodiester groups, etc.) by the photolabile protecting groups, and then eliminating the photolabile protecting groups only by light irradiation under neutral conditions. Another object of the present invention is to provide a deprotection method that allows quantitative determination of the deprotection of the photolabile protecting groups with a high sensitivity.

Means for Solving the Problems

The present inventors conducted extensive research in view of the above-described objects, and found that when a compound having a thiochromone skeleton is used as a protecting group of a reactive functional group (e.g., a hydroxyl group, amino group, carboxyl group, carbonyl group, phosphodiester group, etc.), the protecting group can easily be removed only by light irradiation under neutral conditions. That is, the inventors found that a compound having a predetermined thiochromone skeleton is useful as a photolabile protecting group. The inventors also found that when the compound having a predetermined thiochromone skeleton is used as a protecting group, a polycyclic compound produced by deprotection has very high fluorescence quantum yield, and the deprotection can be quantified with a high sensitivity. For example, the quantification can be performed by measuring the fluorescence emitted by 365-nm light irradiation. The inventors further found that when the compound having a predetermined thiochromone skeleton is used as a protecting group, the protecting group can be collected with a high yield as a result of deprotection. The present invention was accomplished upon further studies based on these findings.

More specifically, the present invention provides a photolabile protecting group, a compound that can serve as the photolabile protecting group, a method of producing the compound, a method of protecting a functional group using the compound, and a method of removing the photolabile protecting group.

The present invention is described in detail below.

I. Protection and Deprotection of Amino Groups

According to the protection and deprotection method of amino groups of the present invention, an amino group is reacted with a compound represented by Formula (3):

[Chem. 2]

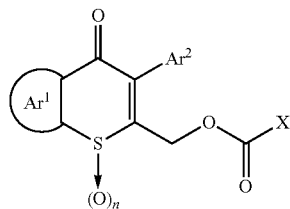

(3)

wherein $Ar^1$ is an optionally substituted aromatic or heteroaromatic ring, $Ar^2$ is an optionally substituted aryl or heteroaryl group, X is a leaving group, and n is an integer of 1 or 2, to be protected by a protecting group represented by Formula (3a):

[Chem. 3]

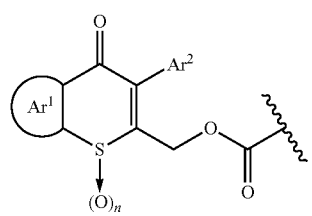

(3a)

wherein $Ar^1$, $Ar^2$, and n are as defined above. The protected amino group is then deprotected by light irradiation, thereby reproducing the amino group. The term "amino group" as used herein denotes a monovalent functional group of ammonia, primary amine, or secondary amine from which a hydrogen atom is removed.

The protection and deprotection method of amino groups of the present invention is specifically illustrated by the following reaction scheme.

[Chem. 4]

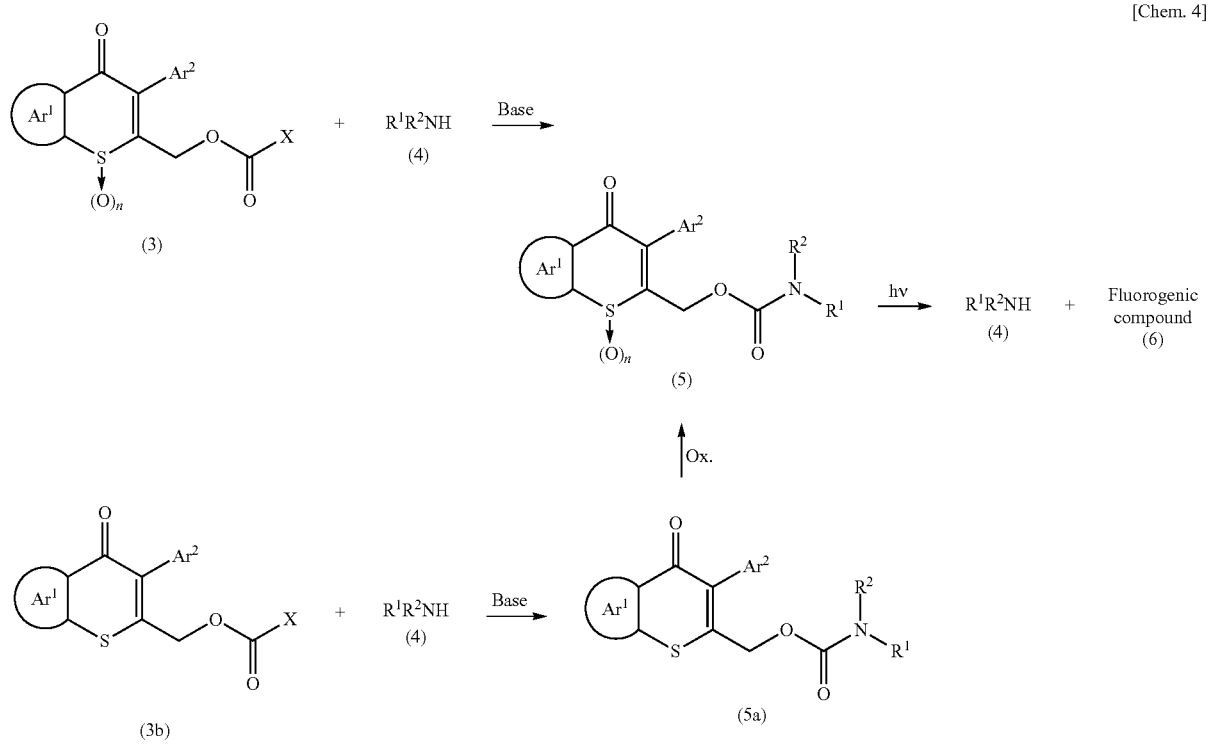

wherein $R^1$ and $R^2$ are the same or different, and each represent a hydrogen atom or an organic group; and $Ar^1$, $Ar^2$, X, and n are as defined above.

The "optionally substituted aromatic or heteroaromatic ring" expressed by $Ar^1$ may be a monocyclic or polycyclic (e.g., bicyclic or tricyclic) aromatic or heteroaromatic ring. Examples thereof include benzene rings, naphthalene rings, anthracene rings, phenanthrene rings, fluorene rings, dibenzo [b,d]furan rings, pyridine rings, pyrimidine rings, pyrazine rings, and the like. The substituent of the aromatic or heteroaromatic ring is not limited, as long as it has no adverse effect on the protection and deprotection reactions of reactive functional groups of the present invention. Examples thereof include alkyl groups (e.g., C1-3 alkyl groups), haloalkyl groups (e.g., C1-3 haloalkyl groups, particularly trifluoromethyl groups, etc.), alkoxy groups (e.g., C1-3 alkoxy groups, particularly methoxy groups, ethoxy groups, etc.), dialkylamino groups (e.g., di(C1-3 alkyl)amino groups), halogen atoms (e.g., fluorine atoms, chlorine atoms, etc.), cyano groups, nitro groups, and the like. The aromatic ring may have 1 to 3 substituents. Among these, benzene rings are preferred; in terms of longer absorption wavelength, polycyclic aromatic hydrocarbon rings, such as naphthalene rings and anthracene rings, are preferred.

n is an integer of 1 or 2, and preferably 2 because the reactivity of the photodissociation reaction is high. When n is 0, the photodissociation reaction does not proceed.

The "optionally substituted aryl or heteroaryl group" expressed by $Ar^2$ may be a monocyclic or polycyclic (e.g., bicyclic or tricyclic) aryl or heteroaryl group. Examples thereof include phenyl groups, naphthyl groups, anthryl groups, phenanthryl groups, fluorenyl groups, dibenzo[b,d] furanyl groups, pyridyl groups, pyrimidinyl groups, pyrazinyl groups, and the like. The substituent of the aryl or heteroaryl group is not limited, as long as it has no adverse effect on the protection and deprotection reactions of reactive functional groups of the present invention. Examples thereof include alkyl groups (e.g., C1-3 alkyl groups, particularly methyl groups, etc.), haloalkyl groups (e.g., C1-3 haloalkyl groups, particularly trifluoromethyl groups, etc.), alkoxy groups (e.g., C1-3 alkoxy groups, particularly methoxy groups, ethoxy groups, etc.), dialkylamino groups (e.g., di(C1-3 alkyl)amino groups), halogen atoms (e.g., fluorine atoms, chlorine atoms, etc.), cyano groups, nitro groups, and the like. The aryl group may have 1 to 3 substituents. Specific examples thereof include phenyl groups, 3,5-dimethoxyphenyl groups, 3,5-ditrifluoromethyl phenyl groups, 4-methoxyphenyl groups, 4-dimethylamino phenyl groups, 1- or 2-naphthyl groups, and the like. Among these, phenyl groups and 3,5-dimethoxyphenyl groups are preferred in terms of photodissociation reaction efficiency (reaction rate).

The leaving group expressed by X is not limited, as long as it can undergo substitution reaction with amino groups. Examples thereof include halogen atoms (e.g., chlorine, bromine, etc.), imidazolyl groups, pentafluorophenyl groups, and the like. Chlorine atoms are preferred.

The organic groups expressed by $R^1$ and $R^2$ are not limited, as long as they have no adverse effect on the protection and deprotection reactions of the present invention. Examples thereof include saturated and unsaturated, linear, branched, and cyclic aliphatic hydrocarbon groups, aromatic hydrocarbon groups, and heteroaromatic hydrocarbon groups, and groups derived therefrom. $R^1$ and $R^2$ may be bonded together to form a ring. These groups may have various substituents. That is, the compound represented by Formula (4) includes various compounds, as long as they have an amino group that can be protected. Such compounds may have not only one amino group, but also two or more amino groups. For example, a wide range of compounds having an —NH— group, such as amino acids, peptides, amino sugars, DNA, proteins, enzymes, and bioactive compounds having amino groups, are exemplified. When any of these compounds are used, the desired protection and deprotection reactions can be achieved.

The following shows a typical example of the process of protecting and deprotecting amino groups.

The compound represented by Formula (4) is reacted with the compound represented by Formula (3) in a solvent generally in the presence of a base. The amount of the compound represented by Formula (3) used is generally 1 mol or more, preferably 1 to 20 mol, and more preferably 1 to 5 mol, based on 1 mol of the compound represented by Formula (4).

Examples of solvents include methylene chloride, chloroform, tetrachloroethane, and other halogen (particularly chlorine)-based solvents; acetonitrile, dimethyl sulfoxide, dimethyl formamide, dimethyl acetamide, acetone, and other aprotic polar solvents; benzene, toluene, xylene, and other hydrocarbon-based solvents; and diethyl ether, tetrahydrofuran, dioxane, dimethoxyethane, and other ether-based solvents. Chlorine-based solvents, as typified by methylene chloride, are preferred.

Examples of bases include organic bases such as pyridine, triethylamine, and diisopropylethylamine; pyridine is preferred. The amount of base used is generally 1 mol or more, preferably 10 to 200 mol, and more preferably 50 to 150 mol, based on 1 mol of the compound represented by Formula (4).

Although the concentration of the compound represented by Formula (4) is not limited in the reaction, it may generally be about 0.05 to 0.2 mol/L. The reaction is preferably carried out in an inert gas (e.g., nitrogen) atmosphere. The reaction temperature is generally 0 to 50° C., and preferably 10 to 30° C. The reaction time is generally about 0.5 to 1 hour.

After the termination of the reaction, working-up is carried out by any known method, followed by purification by a conventional method (e.g., column chromatography) to obtain a urethane compound represented by Formula (5) (a compound having a protected amino group).

The compound represented by Formula (5) can alternatively be produced by reacting a compound represented by Formula (3b) with the compound represented by Formula (4) in the presence of a base, as described above, to obtain a compound represented by Formula (5a), and oxidizing the sulfur atom of the resulting compound with an oxidizing agent, such as m-CPBA.

Subsequently, the urethane compound represented by Formula (5) is irradiated with light in the presence of a solvent to reproduce the compound represented by Formula (4). Examples of solvents include methanol, ethanol, isopropyl alcohol, and other alcohol-based solvents; dioxane, acetonitrile, dimethyl sulfoxide, water, and the like. Methanol is preferred. The concentration of the compound represented by Formula (5) may generally be about $1 \times 10^{-2}$ to $1 \times 10^{-5}$ mol/L.

The light source used for the light irradiation is not limited, as long as the absorption wavelength (250 to 400 nm) of the protecting group represented by Formula (3a) is included. For example, a high-pressure mercury lamp, an ultra high-pressure mercury lamp, a xenon lamp, and the like can be used. If necessary, the wavelength of 280 nm or less may be cut using, for example, a Pyrex® filter. The photoreaction is preferably carried out in an inert gas (e.g., nitrogen) atmosphere. The reaction temperature is generally 0 to 40° C., and preferably 10 to 30° C. The reaction time is generally about 0.5 to 1 hour.

After the termination of the reaction, the reaction mixture is concentrated, followed by purification by a conventional method (e.g., column chromatography) to collect the amine compound represented by Formula (4).

In the present invention, the compound represented by Formula (5) is irradiated with light, so that the protecting group on the nitrogen is released, thereby producing a polycyclic compound (6). This compound has a high fluorescence quantum yield (Φ=0.85), and exhibits intense fluorescence in the visible light region. Accordingly, the release of the amine compound represented by Formula (4) as a result of the deprotection reaction can be detected with a high sensitivity.

For example, the following is an example where a benzyl ester of L-phenylalanine, i.e., the compound represented by Formula (4), is protected by a compound represented by Formula (3d) to obtain a compound (5d), which is then irradiated with light.

[Chem. 5]

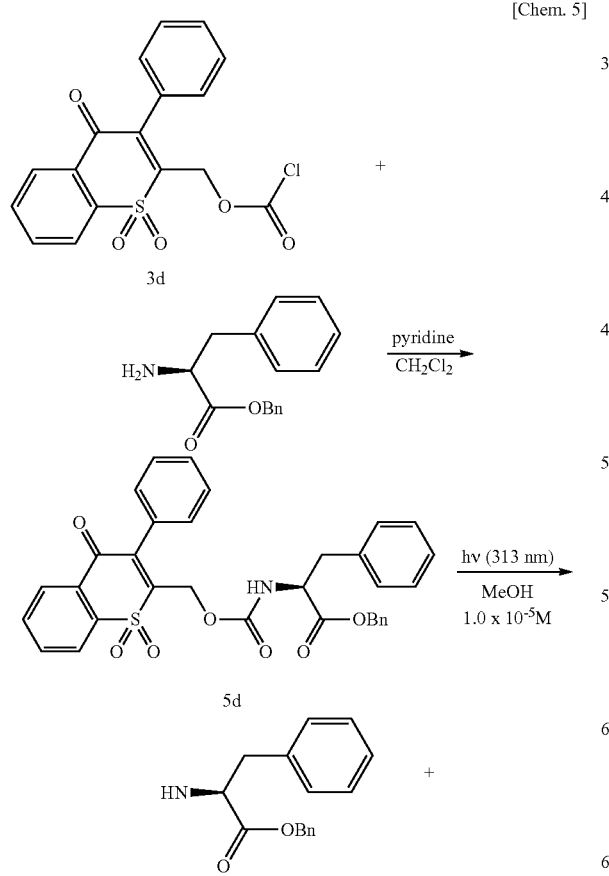

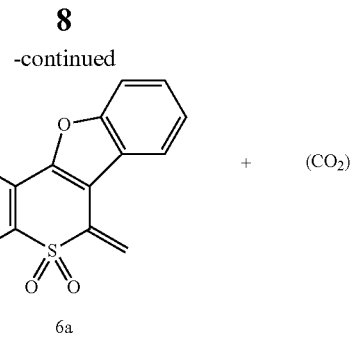

6a

As a result of this reaction, the benzyl ester of L-phenylalanine is almost quantitatively collected, and a tetracyclic compound (6a) produced by this reaction exhibits intense fluorescence in the visible light region (peak: 450 nm).

II. Protection and Deprotection of Hydroxyl Groups

The protection and deprotection method of hydroxyl groups of the present invention can be performed in the same manner as that of amino groups described in Section I above. More specifically, a hydroxyl group is reacted with a compound represented by Formula (3):

[Chem. 6]

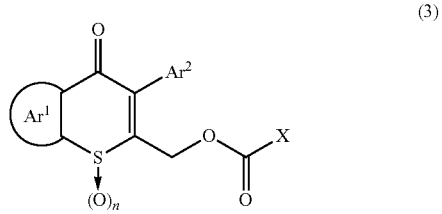

wherein $Ar^1$, $Ar^2$, X, and n are as defined above, to be protected by a protecting group represented by Formula (3a):

[Chem. 7]

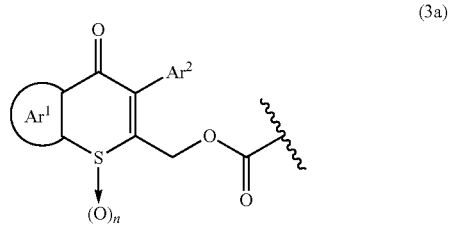

wherein $Ar^1$, $Ar^2$, and n are as defined above, to obtain a carbonate. The protected hydroxyl group is then deprotected by light irradiation, thereby reproducing the hydroxyl group.

The protection and deprotection method of hydroxyl groups of the present invention is specifically illustrated by the following reaction scheme.

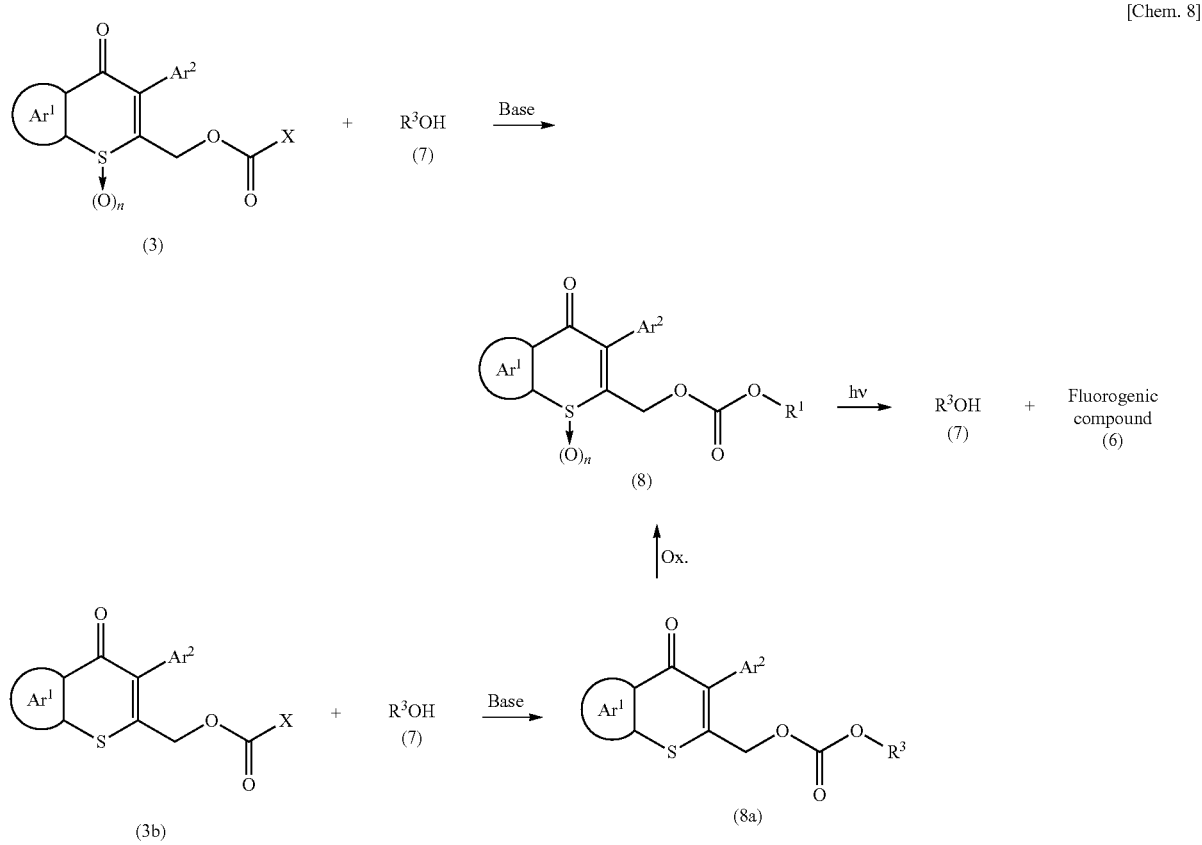

[Chem. 8]

wherein $R^3$ is an organic group, and $Ar^1$, $Ar^2$, n, and X are as defined above. $Ar^1$, $Ar^2$, n, and X are as described above.

The organic group expressed by $R^3$ is not limited, as long as it has no adverse effect on the protection and deprotection reactions of the present invention. Examples thereof include saturated and unsaturated, linear, branched, and cyclic aliphatic hydrocarbon groups, aromatic hydrocarbon groups, and heteroaromatic hydrocarbon groups, and groups derived therefrom. These groups may have various substituents. That is, the compound represented by Formula (7) includes various compounds, as long as they have a hydroxyl group that can be protected. Such compounds may have not only one hydroxyl group, but also two or more hydroxyl groups. For example, a wide range of compounds, such as alcohols, polyols, saccharides, and bioactive compounds having a hydroxyl group, are exemplified. When any of these compounds are used, the desired protection and deprotection reactions can be achieved.

The following shows a typical example of the process of protecting and deprotecting hydroxyl groups.

The compound represented by Formula (7) is reacted with the compound represented by Formula (3) in a solvent generally in the presence of a base. The amount of the compound represented by Formula (3) used is generally 1 mol or more, preferably 1 to 20 mol, and more preferably 1.5 to 5 mol, based on 1 mol of the compound represented by Formula (7).

Examples of solvents include methylene chloride, chloroform, tetrachloroethane, and other halogen (particularly chlorine)-based solvents; acetonitrile, dimethyl sulfoxide, dimethyl formamide, dimethyl acetamide, acetone, and other aprotic polar solvents; benzene, toluene, xylene, and other hydrocarbon-based solvents; diethyl ether, tetrahydrofuran, dioxane, dimethoxyethane, and other ether-based solvents; and the like. Chlorine-based solvents, as typified by methylene chloride, are preferred.

Examples of bases include organic bases such as pyridine, triethylamine, and diisopropylethylamine; pyridine is preferred. The amount of base used is generally 1 mol or more, preferably 10 to 200 mol, and more preferably 50 to 150 mol, based on 1 mol of the compound represented by Formula (7).

In the reaction, the concentration of the compound represented by Formula (7) may generally be about 0.05 to 0.2 mol/L. The reaction is preferably carried out in an inert gas (e.g., nitrogen) atmosphere. The reaction temperature is generally 0 to 50° C., and preferably 10 to 30° C. The reaction time is generally about 0.5 to 1 hour.

After the termination of the reaction, working-up is carried out by any known method, followed by purification by a conventional method (e.g., column chromatography) to obtain a urethane compound represented by Formula (8) (a compound having a protected amino group).

The compound represented by Formula (8) can alternatively be produced by reacting a compound represented by Formula (3b) with the compound represented by Formula (7) in the presence of a base, as described above, to obtain a compound represented by Formula (8a), and oxidizing the sulfur atom of the resulting compound with an oxidizing agent, such as m-CPBA.

The deprotection reaction can be performed in the same or a similar manner as that of amino groups described above. In the present invention, the compound represented by Formula (8) is irradiated with light, allowing the protecting group on the oxygen to be released, and thereby producing a polycyclic compound (6). This compound has a high fluorescence quantum yield (Φ=0.85), and exhibits intense fluorescence in the visible light region. Accordingly, the release of the alcohol represented by Formula (7) as a result of the deprotection reaction can be detected with a high sensitivity.

III. Protection and Deprotection of Carboxyl Groups

According to the protection and deprotection method of carboxyl groups of the present invention, a carboxyl group is esterified by reaction with a compound represented by Formula (1):

[Chem. 9]

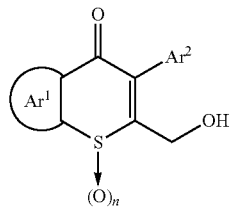

(1)

wherein $Ar^1$, $Ar^2$, and n are as defined above, to be protected by a protecting group represented by Formula (1a):

[Chem. 10]

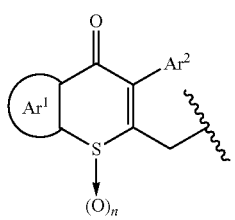

(1a)

wherein $Ar^1$, $Ar^2$, and n are as defined above. The protected carboxyl group is then deprotected by light irradiation, thereby reproducing the carboxyl group.

The protection and deprotection method of carboxyl groups of the present invention is specifically illustrated by the following reaction scheme.

[Chem. 11]

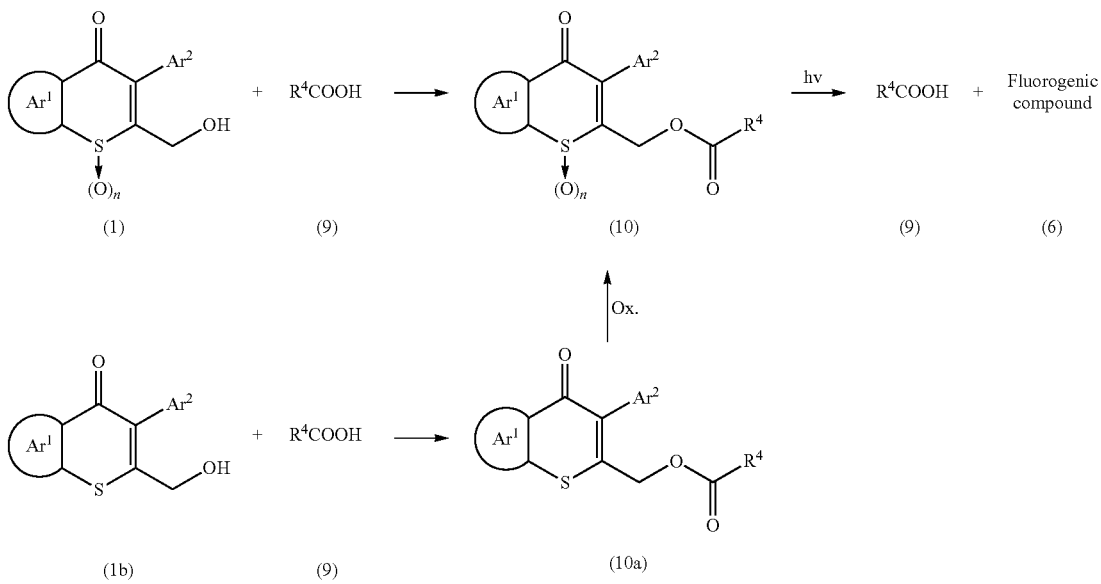

wherein $R^4$ is a hydrogen atom or an organic group, and $Ar^1$, $Ar^2$, and n are as defined above. $Ar^1$, $Ar^2$, and n are as described above.

The organic group expressed by $R^4$ is not limited, as long as it has no adverse effect on the protection and deprotection reactions of the present invention. Examples thereof include saturated and unsaturated, linear, branched, and cyclic aliphatic hydrocarbon groups, aromatic hydrocarbon groups, and heteroaromatic hydrocarbon groups, and groups derived therefrom. These groups may have various substituents. That is, the compound represented by Formula (9) includes various compounds, as long as they have a carboxyl group that can be protected, as described above. Such compounds may have not only one carboxyl group, but also two or more carboxyl groups. For example, a wide range of compounds, such as monocarboxylic acids, polycarboxylic acids, and bioactive compounds having a carboxyl group, are exemplified. When any of these compounds are used, the desired protection and deprotection reactions can be achieved.

The following shows a typical example of the process of protecting and deprotecting carboxyl groups.

The compound represented by Formula (9) or a reactive equivalent thereof is reacted with the compound represented by Formula (1) in a solvent. Examples of solvents include methylene chloride, chloroform, tetrachloroethane, and other halogen (particularly chlorine)-based solvents; acetonitrile, dimethyl sulfoxide, dimethyl formamide, dimethyl acetamide, acetone, and other aprotic polar solvents; benzene, toluene, xylene, and other hydrocarbon-based solvents; diethyl ether, tetrahydrofuran, dioxane, dimethoxyethane, and other ether-based solvents; and the like. Chlorine-based solvents, as typified by methylene chloride, are preferred.

When the compound represented by Formula (9) is a carboxylic acid compound, for example, a dehydration condensation agent, such as dicyclohexylcarbodiimide (DCC), diisopropylcarbodiimide (DIPC), and 1-ethyl-3-(3-dimethylaminopropyl)carbodiimide (EDC), is used. If necessary, an activator, such as dimethylaminopyridine (DMAP), may be added. The amount of the compound represented by Formula (1) is generally 1 mol or more, preferably 1 to 10 mol, and more preferably 1 to 2 mol, based on 1 mol of the compound represented by Formula (9). The amount of dehydration condensation agent used is generally 1 to 1.5 mol, and preferably 1.1 to 1.2 mol, based on 1 mol of the compound represented by Formula (9). The amount of activator may be a catalytic amount.

When the compound represented with Formula (9) is a reactive equivalent of the carboxylic acid compound, the reactive equivalent may be an acid halide (particularly an acid chloride), mixed acid anhydride, imidazolide, or the like. The carboxylic acid can be converted to these reactive equivalents by any known method. In the reaction, pyridine, triethylamine, diisopropylethylamine, and other bases are generally used; pyridine is preferred. The amount of the compound represented by Formula (1) used is generally 1 mol or more, preferably 1 to 10 mol, and more preferably 1 to 2 mol, based on 1 mol of the reactive equivalent of the compound represented by Formula (9). The amount of base used is generally about 1 mol or more, preferably 10 to 200 mol, and more preferably 50 to 150 mol, based on 1 mol of the reactive equivalent of the compound represented by Formula (9).

In the reaction, the concentration of the compound represented by Formula (9) or a reactive equivalent thereof may generally be about 0.05 to 0.2 mol/L. The reaction is preferably carried out in an inert gas (e.g., nitrogen) atmosphere. The reaction temperature is generally 0 to 50° C., and preferably 10 to 30° C. The reaction time is generally 3 to 6 hours.

After the termination of the reaction, concentration is performed, followed by purification by a conventional method (e.g., column chromatography) to collect an ester compound represented by Formula (10).

The compound represented by Formula (10) can alternatively be produced by reacting a compound represented by Formula (1b) with the compound represented by Formula (9) or a reactive equivalent thereof in the same manner as described above to obtain a compound represented by Formula (10a), and oxidizing the sulfur atom of the resulting compound with an oxidizing agent, such as m-CPBA.

The deprotection reaction can be performed in the same or a similar manner as that of amino groups described above. In the present invention, the compound represented by Formula (10) is irradiated with light, allowing the protecting group on the oxygen to be released, and thereby producing a polycyclic compound (6). This compound has a high fluorescence quantum yield ($\Phi=0.85$), and exhibits intense fluorescence in the visible light region. Accordingly, the release of the carboxylic acid represented by Formula (9) as a result of the deprotection reaction can be detected with a high sensitivity.

IV. Protection and Deprotection of Carbonyl Groups

According to the protection and deprotection method of carbonyl groups of the present invention, a carbonyl group is acetalized by reaction with a diol compound represented by Formula (11):

[Chem. 12]

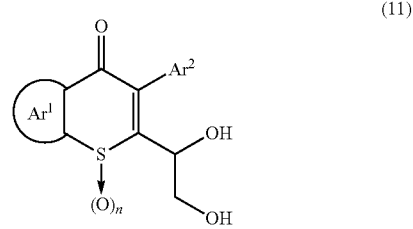

(11)

wherein $Ar^1$, $Ar^2$, and n are as defined above, to be protected by a protecting group represented by Formula (11a):

[Chem. 13]

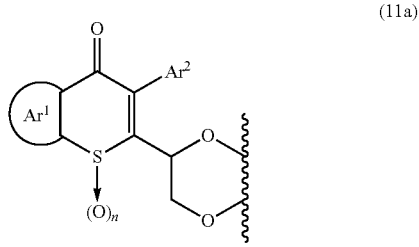

(11a)

wherein $Ar^1$, $Ar^2$, and n are as defined above. The protected carbonyl group is then deprotected by light irradiation, thereby reproducing the carbonyl group.

The method is specifically illustrated by the following reaction scheme.

[Chem. 14]

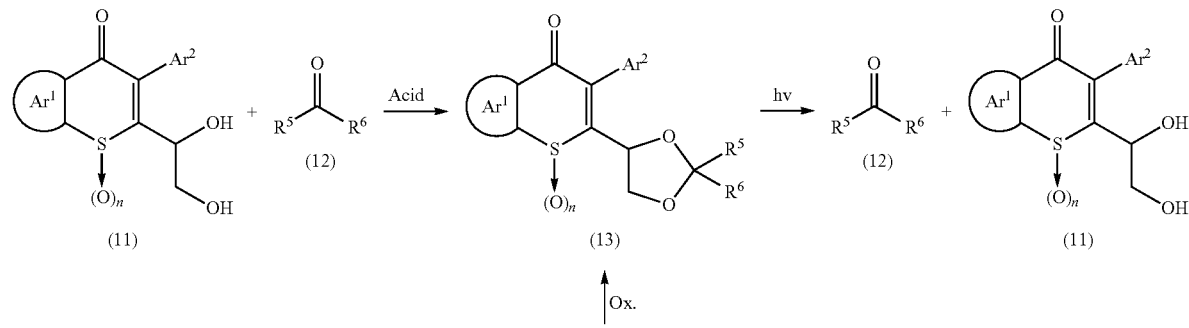

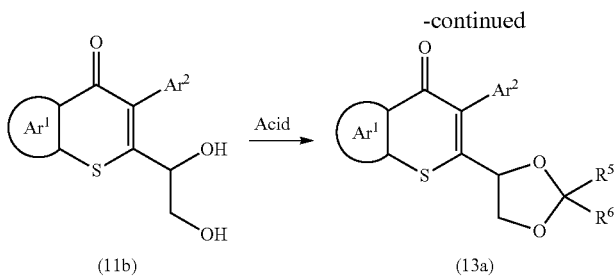

(11b) → (13a)

wherein $R^5$ and $R^6$ are hydrogen atoms or organic groups, and $Ar^1$, $Ar^2$, and n are as defined above. $Ar^1$, $Ar^2$, and n are as described above.

The organic groups expressed by $R^5$ and $R^6$ are not limited, as long as they have no adverse effect on the protection and deprotection reactions of the present invention. Examples thereof include saturated and unsaturated, linear, branched, and cyclic aliphatic hydrocarbon groups, aromatic hydrocarbon groups, and heteroaromatic hydrocarbon groups, and groups derived therefrom. $R^5$ and $R^6$ may be bonded together to form a ring. These groups may have various substituents. That is, the compound represented by Formula (12) includes various compounds, as long as they have a carbonyl group that can be protected. Such compounds may have not only one carbonyl group, but also two or more carbonyl groups. For example, a wide range of ketone compounds or aldehyde compounds, such as monocarbonyl compounds, polycarbonyl compounds, and bioactive compounds having a carbonyl group, are exemplified. When any of these compounds is used, the desired protection and deprotection reactions can be achieved.

The following shows a typical example of the process of protecting and deprotecting carbonyl groups.

The compound represented by Formula (12) is reacted with the compound represented by Formula (11) in a solvent in the presence of an acid catalyst. Examples of solvents include methylene chloride, chloroform, tetrachloroethane, and other halogen (particularly chlorine)-based solvents; acetonitrile, dimethyl formamide, dimethyl acetamide, and other aprotic polar solvents; benzene, toluene, xylene, and other hydrocarbon-based solvents; diethyl ether, tetrahydrofuran, dioxane, dimethoxyethane, and other ether-based solvents; and the like. Methylene chloride is preferred.

The amount of the compound represented by Formula (11) used is generally 1 mol or more, preferably 1 to 20 mol, and more preferably 1 to 5 mol, based on 1 mol of the compound represented by Formula (12). Additionally, a dehydrating agent may be added. The amount of dehydrating agent (e.g., copper sulfate) used is generally 0.5 to 2 mol, and preferably 0.7 to 1.5 mol, based on 1 mol of the compound represented by Formula (12).

A preferred acid catalyst is an organic acid, and examples thereof include p-toluenesulfonic acid (PTSA), pyridinium p-toluenesulfonate (PPTS), camphorsulfonic acid (CSA), and the like. The amount of acid catalyst used is generally about 0.01 to 0.3 mol, based on 1 mol of the compound represented by Formula (12).

In the reaction, the concentration of the compound represented by Formula (12) may generally be about 0.05 to 0.2 mol/L. The reaction temperature is generally 0 to 50° C., and preferably 10 to 30° C. The reaction time is generally 1 to 50 hours, and particularly 5 to 15 hours.

After the termination of the reaction, concentration is performed, followed by purification by a conventional method (e.g., column chromatography) to collect an acetal compound represented by Formula (13).

The compound represented by Formula (13) can alternatively be produced by reacting a compound represented by Formula (11b) with the compound represented by Formula (12) in the presence of the above acid catalyst, as described above, to obtain a compound represented by Formula (13a), and oxidizing the sulfur atom of the resulting compound with an oxidizing agent, such as m-CPBA.

The deprotection reaction can be performed in the same or a similar manner as that of amino groups described above. It is preferable that the solvent further contains water. The protecting group is released from the compound represented by Formula (13) by light irradiation, and the compound represented by Formula (11) and the compound represented by Formula (12), which are starting materials, are nearly quantitatively collected. This photodissociation reaction does not result in a fluorogenic compound represented by Formula (6), as described above. However, the collected compound represented by Formula (12) can be reused as a protecting group, and thus is useful in terms of saving resources.

V. Protection and Deprotection of Phosphodiesters

According to the protection and deprotection method of phosphodiesters of the present invention, a halophosphodiester, which is an equivalent of a phosphodiester, is esterified by reaction with a compound represented by Formula (1):

[Chem.15]

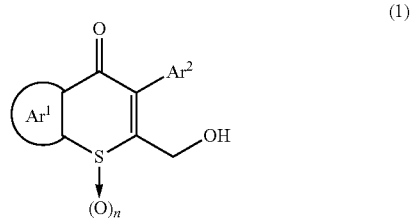

(1)

wherein $Ar^1$, $Ar^2$, and n are as defined above, to protect a phosphodiester by a protecting group represented by Formula (1a):

[Chem.16]

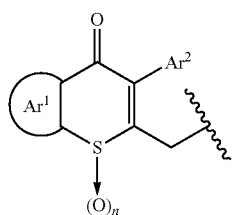
(1a)

wherein $Ar^1$, $Ar^2$, and n are as defined above. The protected phosphodiester is then deprotected by light irradiation, thereby reproducing the phosphodiester.

The protection and deprotection method of phosphodiesters of the present invention is specifically illustrated by the following reaction scheme.

phodiester (i.e., an equivalent of a phosphodiester) that can be protected, as described above. Such compounds may have one halophosphodiester, but also two or more halophosphodiesters. For example, a wide range of compounds, such as monohalophosphate diester compounds, polyhalophosphate diester compounds, and bioactive compounds having a halophosphodiester, are exemplified. When any of these compounds is used, the desired protection and deprotection reactions can be achieved.

The following shows a typical example of the process of protecting and deprotecting phosphodiesters.

The compound represented by Formula (29) is reacted with the compound represented by Formula (1) in a solvent. Examples of solvents include methylene chloride, chloroform, tetrachloroethane, and other halogen (particularly chlorine)-based solvents; acetonitrile, dimethyl sulfoxide, dimethyl formamide, dimethyl acetamide, acetone, N-methylimidazole, and other aprotic polar solvents; ben-

[Chem. 17]

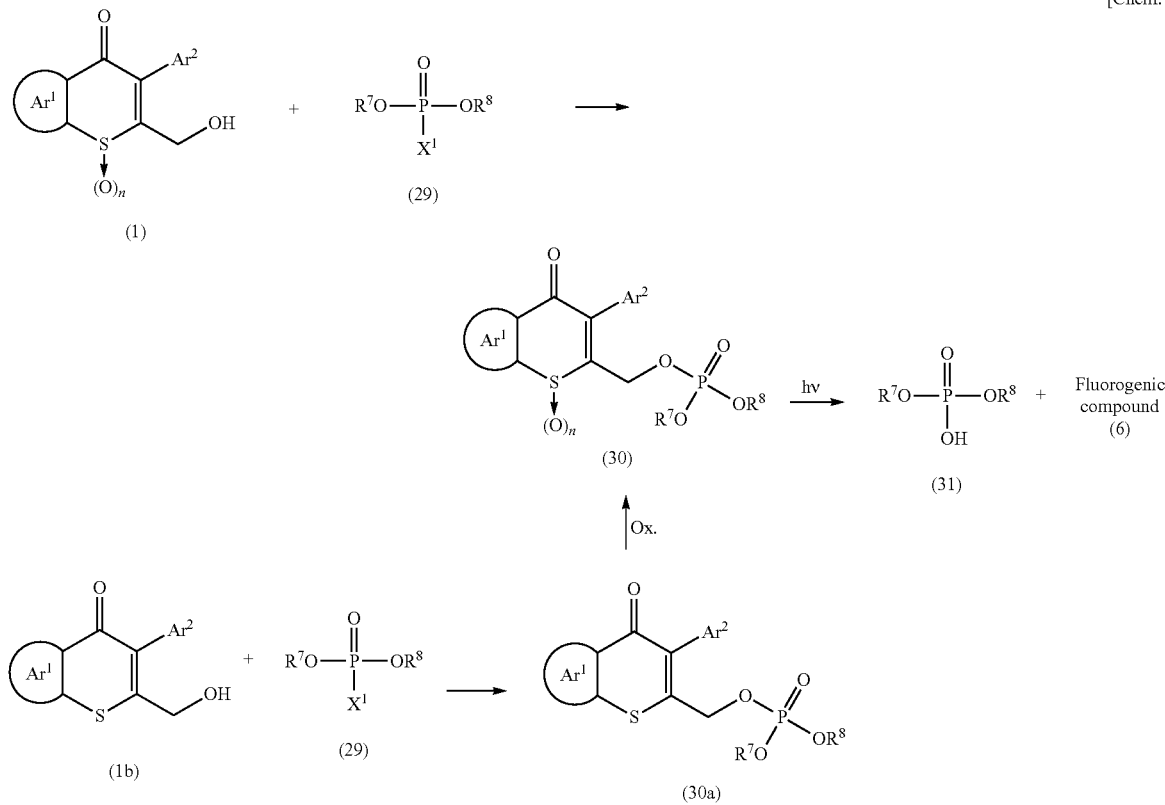

wherein $Ar^1$, $Ar^2$, and n are as described above.

$R^7$ and $R^8$ are the same or different, and each represent an organic group. The organic groups expressed by $R^7$ and $R^8$ are not limited, as long as they have no adverse effect on the protection and deprotection reactions of the present invention. Examples thereof include saturated cyclic aliphatic hydrocarbon groups and aromatic hydrocarbon groups, and groups derived therefrom. These groups may further have various substituents.

Moreover, $X^1$ is a halogen atom. Among halogen atoms, Cl, Br, and I are preferred; Cl is most preferred.

That is, the compound represented by Formula (29) includes various compounds, as long as they have a halophoszene, toluene, xylene, and other hydrocarbon-based solvents; diethyl ether, tetrahydrofuran, dioxane, dimethoxyethane, and other ether-based solvents; and the like. Chlorine-based solvent, as typified by methylene chloride, are preferred. These solvents may be used singly or in combination of two or more.

Additionally, for example, a dehydration condensation agent, such as dicyclohexylcarbodiimide (DCC), diisopropylcarbodiimide (DIPC), and 1-ethyl-3-(3-dimethylaminopropyl)carbodiimide (EDC), may be used. If necessary, an activator, such as dimethylaminopyridine (DMAP), may be added.

The amount of the compound represented by Formula (1) is generally 1 mol or more, preferably 1 to 10 mol, and more preferably 1 to 2 mol, based on 1 mol of the compound represented by Formula (29). When a dehydration condensation agent is used, the amount thereof is generally 1 to 1.5 mol, and preferably 1.1 to 1.2 mol, based on 1 mol of the compound represented by Formula (29). The amount of activator, if used, may be a catalytic amount.

In this reaction, the concentration of the compound represented by Formula (29) may generally be about 0.05 to 0.2 mol/L. The reaction is preferably carried out in an inert gas (e.g., nitrogen) atmosphere. The reaction temperature is generally 0 to 50° C., and preferably 10 to 30° C. The reaction time is generally 3 to 6 hours.

After the termination of the reaction, concentration is performed, followed by purification by a conventional method (e.g., column chromatography) to collect a phosphodiester compound represented by Formula (31).

The compound represented by Formula (31) can alternatively be produced by reacting a compound represented by Formula (1b) with the compound represented by Formula (29) in the same manner as described above to obtain a compound represented by Formula (30a), and oxidizing the sulfur atom of the resulting compound with an oxidizing agent, such as m-CPBA.

The deprotection reaction can be performed in the same or a similar manner as that of amino groups described above. In the present invention, the compound represented by Formula (30) is irradiated with light, allowing the protecting group on the oxygen to be released, and thereby producing a polycyclic compound (6). This compound has a high fluorescence quantum yield ($\Phi$=0.85), and exhibits intense fluorescence in the visible light region. Accordingly, the release of the phosphodiester compound represented by Formula (31) as a result of the deprotection reaction can be detected with a high sensitivity.

VI. Specific Application

The protection and deprotection method of reactive functional groups of the present invention can be used for the following applications.

The photolabile protecting group of the present invention has advantages in that it exhibits excellent photodissociation ability when applied to an amino acid, and allows the photodissociation reaction to be monitored by fluorescence analysis of a tetracyclic compound produced from the reaction. Because of these advantages, the protection and deprotection method of amino groups of the present invention can be used in solid phase peptide synthesis or DNA microarray synthesis.

The current standard method of solid phase peptide synthesis is the Fmoc synthesis method. This is a method of extending a peptide chain by repeating an operation, as shown below, in which an Fmoc-amino acid is condensed to the free N-terminus of a solid-phase peptide, the Fmoc is removed using piperidine as a base to activate the N-terminus, and an Fmoc-amino acid is further condensed thereto. The progress of the deprotection reaction in the solid phase can be measured by measuring absorption of N-(9-fluorenyl methyl) piperidine, which is generated from the Fmoc group and piperidine, at 301 nm.

[Chem. 18]

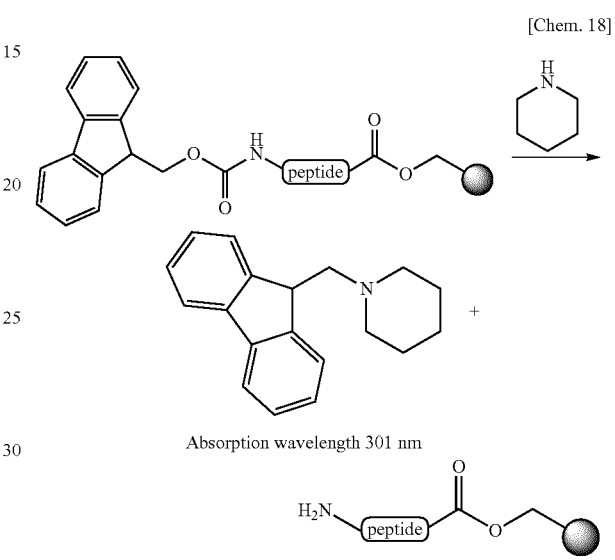

Absorption wavelength 301 nm

When solid phase peptide synthesis is performed using the photolabile protecting group represented by the Formula (3a) of the present invention in place of an Fmoc group, there are presumably the following advantages compared to the above-described Fmoc synthesis method. First, a deprotection reaction can be performed simply by light irradiation under neutral conditions to activate the N-terminus without using a basic reaction reagent, such as piperidine. Moreover, the progress of deprotection on the solid phase can be confirmed using fluorescence of a polycyclic compound represented by Formula (6) generated by deprotection. In addition, the polycyclic compound can be detected with a high sensitivity because of its high fluorescence quantum yield.

[Chem. 19]

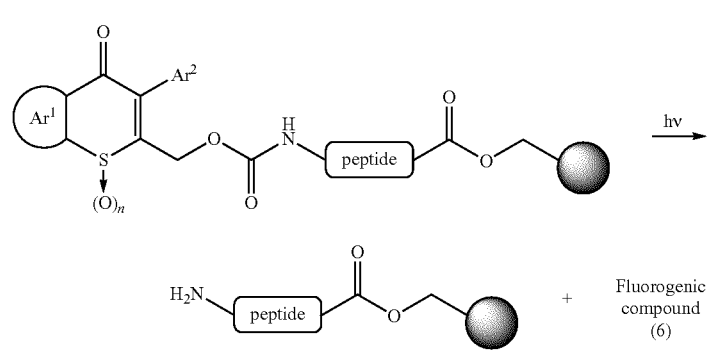

wherein $Ar^1$, $Ar^2$, and n are as defined above.

This can easily be understood from the fact that the following peptide synthesis has been confirmed to be possible, as shown, for example, in Example I-5.

[Chem. 20]

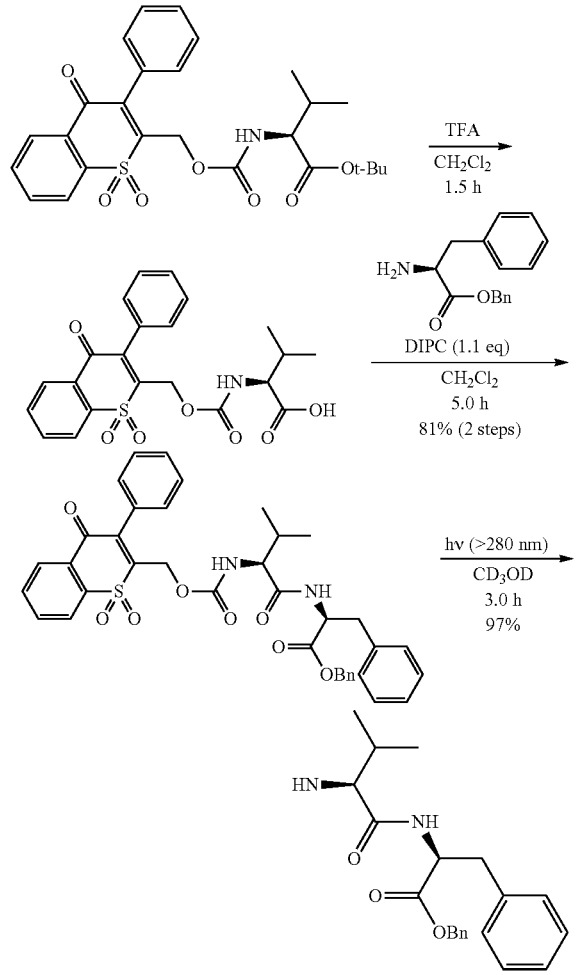

In the photolabile protecting group of the present invention, the oxidation state of the sulfur in the thiochromone skeleton has a great impact on the reactivity of the photodissociation reaction. When the sulfur atom is divalent (n=0), the photodissociation reaction does not proceed; whereas when the oxidation number of the sulfur atom is as large as a tetravalent or hexavalent (n=1 or 2), the photodissociation reaction proceeds immediately. Taking advantage of these properties, on and off of the photodissociation reaction can be controlled by the oxidation state of the sulfur in the protecting group.

For example, a compound having two or more amino groups or hydroxyl groups in one molecule is protected by a protecting group represented by Formula (3a):

[Chem. 21]

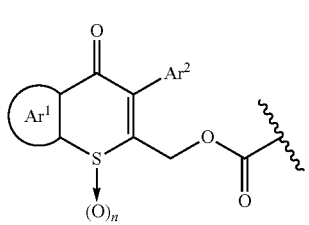

(3a)

wherein $Ar^1$, $Ar^2$, and n are as defined above, and a protecting group represented by Formula (3c):

[Chem. 22]

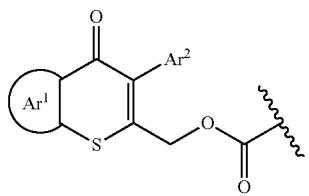

(3c)

wherein $Ar^1$ and $Ar^2$ are as defined above. The compound is irradiated with light to once remove the protecting group represented by Formula (3a). Subsequently, the remaining protecting group represented by Formula (3d) is oxidized with an oxidizing agent (e.g., m-CPBA) to convert it to a protecting group represented by Formula (3a), which is then removed by light irradiation. That is, by taking advantage of the difference in reactivity of the photodissociation reaction between the groups represented by Formulae (3a) and (3c), the protecting groups can be removed according to the desired protocol.

For example, in a compound having two hydroxyl groups, as shown below, the two hydroxyl groups can be distinguishingly deprotected (see Example II-3).

[Chem. 23]

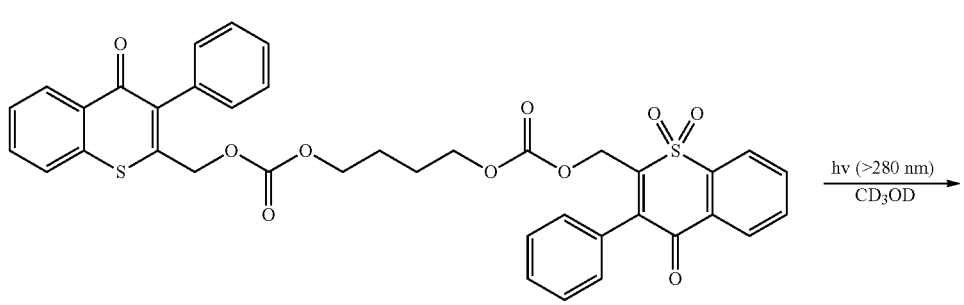

-continued

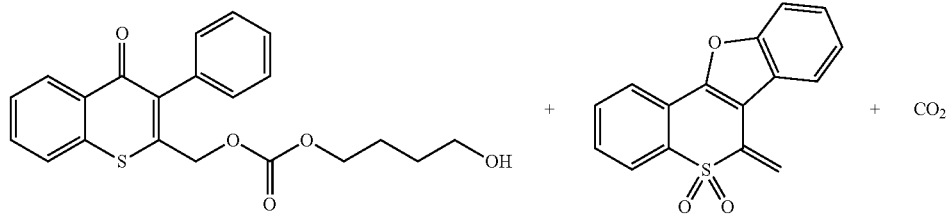

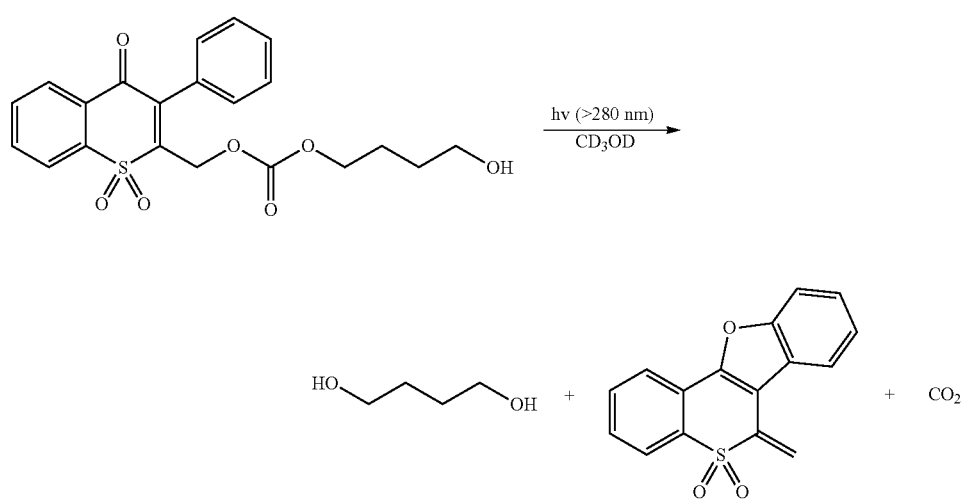

The compound is protected by a protecting group represented by the formula:

[Chem.24]

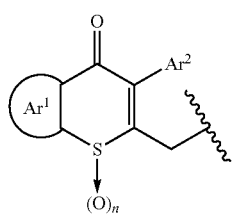
(1a)

wherein $Ar^1$, $Ar^2$, and n are as defined above, and a protecting group represented by Formula (1c):

[Chem.25]

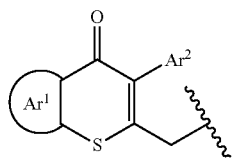
(1c)

wherein $Ar^1$ and $Ar^2$ are as defined above. The compound is irradiated with light to once remove the protecting group represented by Formula (1a). Subsequently, the remaining protecting group represented by Formula (1c) is oxidized with an oxidizing agent (e.g., m-CPBA) to convert it to a protecting group represented by Formula (1a), which is then removed by light irradiation. That is, taking advantage of the difference in reactivity of the photodissociation reaction between the groups represented by Formulae (1a) and (1c), the protecting groups can be removed according to the desired protocol.

Similarly, a compound having two or more carbonyl groups in one molecule (ketone or aldehyde) is protected by a protecting group represented by Formula (11a):

[Chem.26]

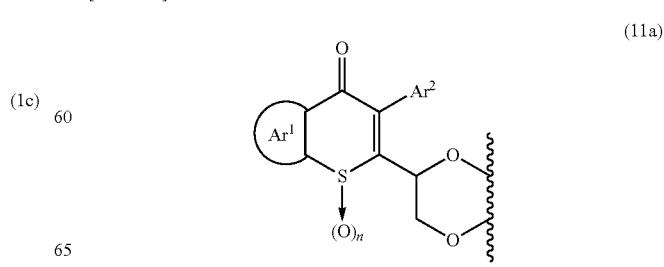
(11a)

wherein $Ar^1$, $Ar^2$, and n are as defined above, and a protecting group represented by Formula (11c):

[Chem.27]

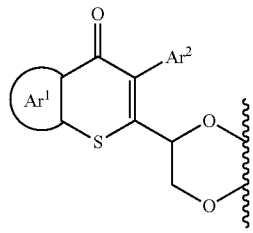

(11c)

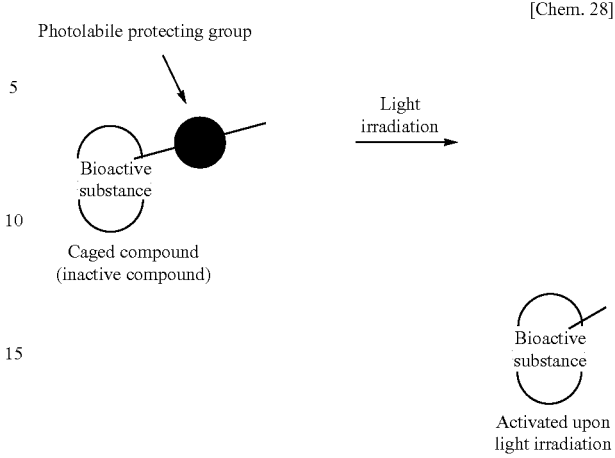

[Chem. 28]

wherein $Ar^1$ and $Ar^2$ are as defined above. The compound is irradiated with light to once remove the protecting group represented by Formula (11a). Subsequently, the remaining protecting group represented by Formula (11c) is oxidized with an oxidizing agent (e.g., m-CPBA) to convert it to a protecting group represented by Formula (11a), which is then removed by light irradiation. That is, taking advantage of the difference in reactivity of the photodissociation reaction between the groups represented by Formulae (11a) and (11c), the protecting groups can be removed according to the desired protocol.

Furthermore, the protecting group of the present invention can also be used as a protecting group of a caged compound. Caged compounds are used to clarify when, where and how signaling-related molecules work, in order to clarify in detail the ordered exchange of information in vivo. More specifically, a caged compound is a bioactive molecule, as shown below, that temporarily loses its activity as a result of being protected by a photodegradable protecting group, which can be removed upon light irradiation, thereby instantly reproducing the original bioactive molecule.

A compound whose functional group, which is necessary for bioactivity, is protected by the photolabile protecting group of the present invention is introduced into a cell. Although this compound does not exhibit bioactivity in its regular state, upon irradiating the compound in the cell with light, the compound is deprotected to be a bioactive substance, expressing its activity. The use of this technique allows the control of the time and place of functional expression of signal molecules by the time and place of light irradiation, as well as the control of the expression level by the amount of irradiation light. Therefore, the technique serves as a powerful method of real-time control of the space-time kinetics of molecules involved in signaling.

VII. Production of Starting Compounds

The compounds represented by Formulae (1), (3), and (3c) used in the present invention can be produced, for example, as follows.

[Chem. 29]
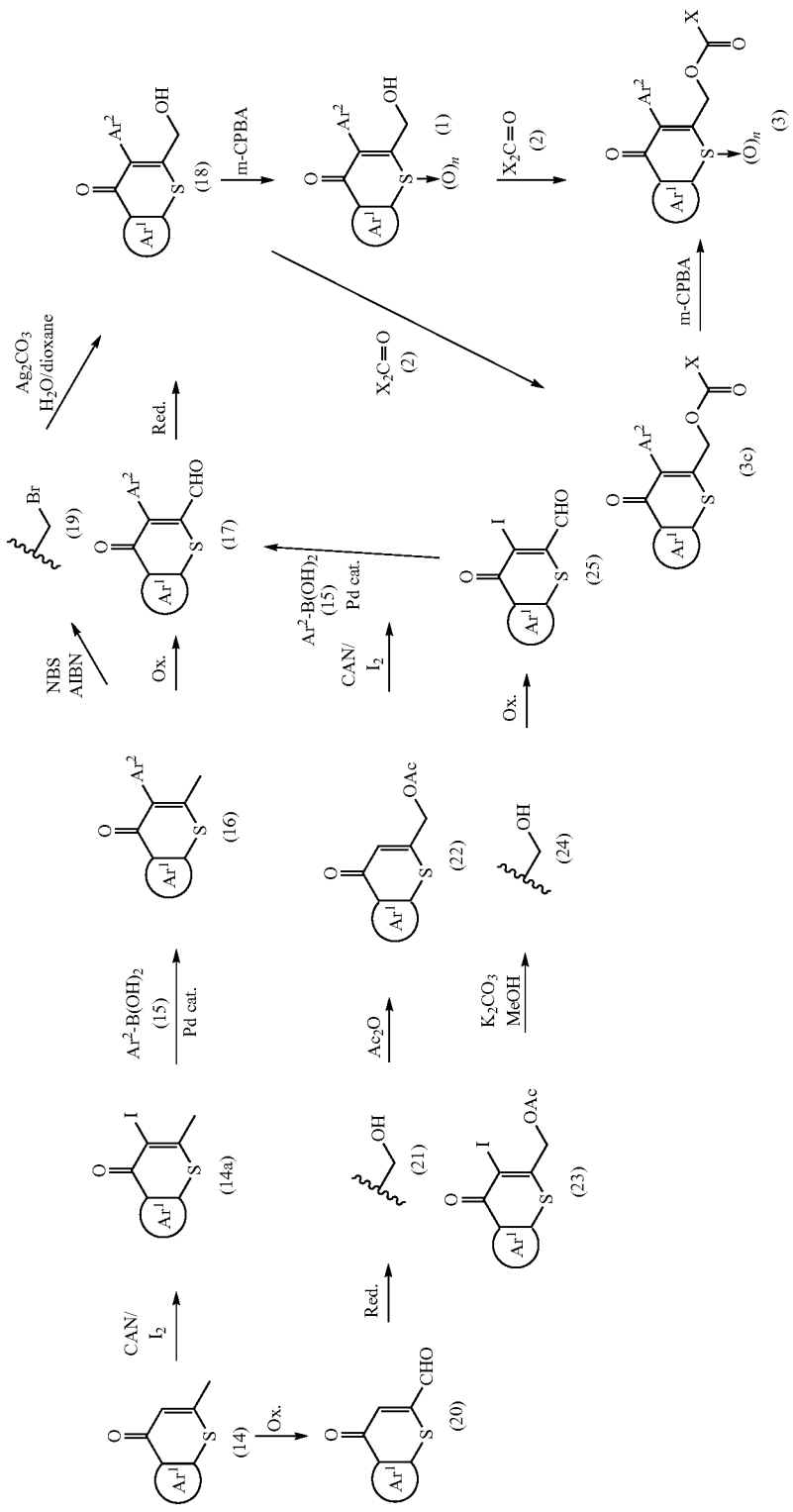

wherein Ar¹, Ar², X, and n are as defined above.

A compound represented by Formula (14), which is a starting material, can be produced by, for example, dehydration condensation of a compound represented by Formula (28):

[Chem. 30]

(28)

wherein Ar¹ is as defined above, and an acetoacetic acid ester (e.g., ethyl acetoacetate) using an acid, such as polyphosphoric acid. This can be performed according to a known method.

The compound represented by Formula (14) is iodinated by reaction with iodine and ceric ammonium nitrate (CAN) to obtain an iodine compound represented by Formula (14a).

The iodine compound represented by Formula (14a) is reacted with an arylboronic acid represented by Formula (15) in the presence of a palladium catalyst (e.g., dichlorobis(triphenylphosphine)palladium) and a base (e.g., potassium carbonate) to obtain a compound represented by Formula (16).

The carbon at the allylic position of the compound represented by Formula (16) is oxidized with an oxidizing agent, such as selenium dioxide, to obtain aldehyde represented by Formula (17). The aldehyde is then converted to an alcohol compound represented by Formula (18) by treatment with a reducing agent, such as sodium borohydride. The alcohol compound represented by Formula (18) can alternatively be produced by reacting the compound represented by Formula (16) with a brominating agent, such as NBS and bromine, in the presence of a radical initiator, such as azobisisobutyronitrile (AIBN), to obtain a bromine compound represented by Formula (19), which is then reacted with silver carbonate in a water-containing solvent.

The compound represented by Formula (18) is oxidized with an oxidizing agent, such as m-CPBA, to obtain a compound represented by Formula (1), i.e., sulfone (n=2) or sulfoxide (n=1).

The compound represented by Formula (1) is reacted with a compound represented by Formula (2) or an equivalent thereof to obtain a compound represented by Formula (3). Two Xs of the compound represented by Formula (2) are as described above, and may be the same or different. Examples of the compound represented by Formula (2) include phosgene (X=Cl), carbonyldiimidazole (CDI), 4-nitrophenyl chloroformate, and the like. As for equivalents thereof, triphosgene is exemplified as an equivalent of phosgene. In the reaction, it is preferable that phosgene is prepared from triphosgene and Aliquat, and then reacted with the compound represented by Formula (1).

The compound represented by Formula (18) can be reacted with the compound represented by Formula (2) or an equivalent thereof to obtain a compound represented by Formula (3c). The reaction is as described above.

The compound represented by Formula (3c) is oxidized with an oxidizing agent, such as m-CPBA, as described above, to obtain a compound represented by Formula (1), i.e., sulfone (n=2) or sulfoxide (n=1).

The carbon at the allylic position of the compound represented by Formula (14) is oxidized with an oxidizing agent, such as selenium dioxide, to obtain aldehyde represented by Formula (20). The aldehyde is then converted to an alcohol compound represented by Formula (21) by treatment with a reducing agent, such as sodium borohydride.

The alcohol compound represented by Formula (21) is acetylated with acetic anhydride to obtain a compound represented by Formula (22). This compound is then iodinated by reaction with iodine and ceric ammonium nitrate (CAN) to obtain an iodine compound represented by Formula (23).

The compound represented by Formula (23) is deacetylated with calcium carbonate/methanol to obtain an alcohol compound represented by Formula (24). The alcohol compound is then oxidized with an oxidizing agent, such as 2-iodoxybenzoic acid (IBX), to obtain a compound represented by Formula (25). This compound is reacted with the arylboronic acid represented by Formula (15) in the presence of a palladium catalyst (e.g., dichlorobis(triphenylphosphine)palladium) and a base (e.g., potassium carbonate) to obtain a compound represented by Formula (17).

The compounds represented by Formulae (11) and (11b) used in the present invention can be produced, for example, as follows.

[Chem. 31]

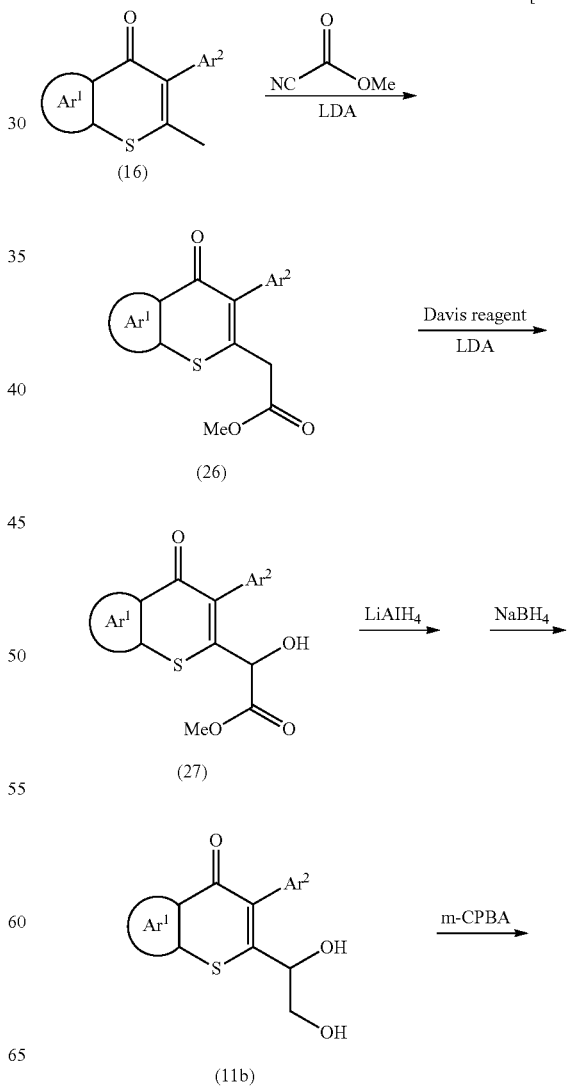

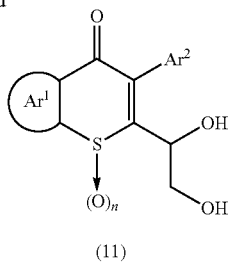

(11)

wherein $Ar^1$, $Ar^2$, X, and n are as defined above.

At a low temperature (about −78° C.), a compound represented by Formula (16) is reacted with a base, such as lithium diisopropylamide (LDA) and lithium hexamethyldisilazide, in a solvent, such as tetrahydrofuran (THF). Then, cyanomethyl formate is added for reaction to obtain a compound represented by Formula (26).

At a low temperature (about −78° C.), the compound represented by Formula (16) is reacted with a base, such as lithium diisopropylamide (LDA) and lithium hexamethyldisilazide, in a solvent, such as tetrahydrofuran (THF). Then, a Davis reagent is reacted to obtain a compound represented by Formula (27).

The compound represented by Formula (27) is reacted with lithium aluminum hydride ($LiAlH_4$) in THF to obtain an aldehyde product. The aldehyde product is further reacted with sodium borohydride ($NaBH_4$) in an alcohol (e.g., methanol) to obtain a compound represented by Formula (28).

The compound represented by Formula (28) is oxidized with an oxidizing agent, such as m-CPBA, to obtain a compound represented by Formula (11), i.e., sulfone (n=2) or sulfoxide (n=1). This compound is novel and useful as a photolabile protecting group for carbonyl compounds, such as ketones and aldehydes.

Effect of the Invention

The photolabile protecting group of the present invention can protect a reactive functional group (e.g., a hydroxyl group, amino group, carboxyl group, carbonyl group, etc.), and then can be efficiently removed only by light irradiation under neutral conditions. Therefore, the photolabile protecting group is a very effective tool in organic synthesis.

Conventionally, the quantitative determination of a deprotection reaction (photodissociation reaction) necessitates the use of a nuclear magnetic resonance spectrum or other analytical instrument. However, when a predetermined protecting group is used, a compound resulting from photodissociation has high luminescence, and therefore, the deprotection reaction (photodissociation reaction) can quantitatively be confirmed by the fluorescence spectra of the luminescence. Moreover, when such a protecting group is adapted for solid phase synthesis of a peptide etc., the frequency of a photodissociation reaction on the surface can be quantified with a high sensitivity.

Furthermore, the protecting group having a thiochromone skeleton of the present invention has a sulfur atom, and the progress of the deprotection reaction (photodissociation reaction) can be controlled by the oxidation state of the sulfur atom. Accordingly, only desired reactive functional groups can be selectively deprotected.

BEST MODE FOR CARRYING OUT THE INVENTION

Examples

The present invention is described in further detail with reference to the Examples; however, the present invention is not limited thereto.

Measurement Device

The following measurement devices were used in the Examples.

NMR: JEOL JMN-ECP500;

MS: JOEL JMS-700;

IR: JASCO FT/IR 400, for $CHCl_3$, a product for absorbance, produced by Wako Pure Chemical Industries, Ltd., was used;

Thin-layer chromatography: Merck 60 F254 plates were used;

UV lamp (254 nm, 365 nm) irradiation: detected using a phosphomolybdic acid ethanol color reagent;

Super-high pressure mercury lamp: SX-UI 500H0 light source, USHIO;

Ultraviolet visible spectrum: SHIMADZU UV-1600;

Fluorescence spectrum: FP-6500DS; and

Monochromator: SPG-120UV

Synthesis of Starting Material

Production Example 1

(1) Synthesis of 3-iodo-2-methyl-4H-thiochromen-4-one

[Chem. 32]

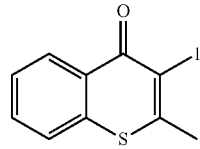

2-Methyl-4H-thiochromen-4-one (1.0 mmol, 176 mg), iodine (1.2 mmol, 305 mg) and ceric ammonium nitrate (1.1 mmol, 603 mg) were dissolved in acetonitrile (4.0 mL), and the solution was stirred under a nitrogen atmosphere at 60° C. for 4 hours. After the disappearance of the starting materials was confirmed by thin-layer chromatography, the reaction solution was poured into a solution of a 10% saturated aqueous sodium thiosulfate solution under ice-cooling to terminate the reaction. The organic substances were extracted with methylene chloride, the obtained organic layer was dried over magnesium sulfate, and the solvents were evaporated under reduced pressure. The residue was purified by silica gel column chromatography, and the title compound (0.79 mmol, 238 mg) was obtained in a 79% yield.

Yellow Solid $^1$H-NMR ($CDCl_3$/TMS) δ: 8.52 (1H, J=7.9 Hz, d), 7.60 (1H, J=7.6, 3.8 Hz, dd), 7.54-7.52 (2H, m), 2.62 (3H, s).

$^{13}$C-NMR (CDCl$_3$) δ: 175.46, 151.12, 136.32, 131.59, 129.77, 128.12, 126.90, 124.86, 103.70, 32.44.

(2) 2-Methyl-3-phenyl-4H-thiochromen-4-one

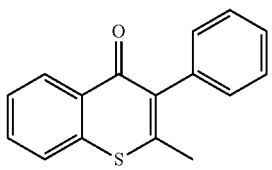

[Chem. 33]

The compound (1.0 mmol, 302 mg) obtained in (1) above, dichlorobis(triphenylphosphine)palladium (0.03 mmol, 21 mg), phenylboronic acid (1.3 mmol, 159 mg) and potassium carbonate (4.0 mmol, 552 mg) were dissolved in degassed dimethylformamide (3.2 mL) and water (0.8 mL), and the solution was stirred under a nitrogen atmosphere at 80° C. for 4 hours. After the disappearance of the starting materials was confirmed by thin-layer chromatography, water was poured into the reaction solution to terminate the reaction. The organic substances were extracted with ethyl acetate, the obtained organic layer was dried over magnesium sulfate, and the solvents were evaporated under reduced pressure. The residue was purified by silica gel column chromatography, and the title compound (0.93 mmol, 237 mg) was obtained in a 93% yield.
White Solid
$^1$H-NMR (CDCl$_3$/TMS) δ: 8.51 (1H, J=8.6 Hz, d), 7.60-7.57 (2H, m), 7.52-7.49 (1H, m), 7.45 (2H, J=7.6, 7.6 Hz, dd), 7.37 (1H, J=7.6, 7.6 Hz, dd), 7.21 (2H, J=7.6 Hz, d), 2.26 (3H, s). $^{13}$C-NMR (CDCl$_3$) δ: 179.14, 147.18, 136.63, 136.40, 136.00, 131.16, 131.09, 129.77, 129.38, 128.45, 127.55, 127.35, 125.52, 22.52.

(3) 2-(Hydroxymethyl)-3-phenyl-4H-thiochromen-4-one

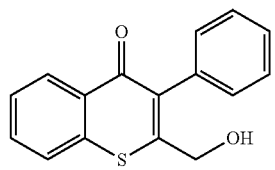

[Chem. 34]

The compound (1.0 mmol, 252 mg) obtained in (2) above and selenium dioxide (1.2 mmol, 133 mg) were dissolved in 5 mL of chlorobenzene, and the solution was refluxed under a nitrogen atmosphere for 12 hours. After the disappearance of the starting materials was confirmed by NMR, the temperature of the solution was returned to room temperature, and a saturated aqueous sodium hydrogen carbonate solution was poured thereinto to terminate the reaction. Then, the organic layer extracted with methylene chloride was dried over magnesium sulfate, and the solvents were distilled off under reduced pressure. The residue was passed through a silica gel column, and directly used in the subsequent reaction. The obtained mixture was dissolved in 2 mL of methanol, to which sodium borohydride (1.0 mmol, 38 mg) was added; and under a nitrogen atmosphere, the resulting product was stirred at 0° C. for 2 hours. Then, a saturated aqueous ammonium chloride solution was added thereto to terminate the reaction. Afterward, the organic substances were extracted with ethyl acetate, the obtained organic layer was dried over magnesium sulfate, and the solvents were evaporated under reduced pressure. The residue was purified by silica gel column chromatography, and recrystallized with hexane/ethyl acetate. Thereby, the title compound (0.38 mmol, 104 mg) was obtained in a two-step yield of 38%.
White Solid
$^1$H-NMR (CDCl$_3$/TMS) (ppm) δ: 8.50 (1H, J=8.0 Hz, d), 7.60 (1H, J=8.0 Hz, d), 7.62 (1H, J=8.0, 8.0 Hz, dd), 7.53 (1H, J=8.0, 8.0 Hz, dd), 7.46-7.37 (3H, m), 7.09 (1H, J=6.7 Hz, d), 4.54 (2H, s). $^{13}$C-NMR (CDCl$_3$) δ: 179.29, 152.34, 136.85, 135.30, 134.65, 131.32, 131.13, 129.43, 129.26, 128.74, 128.07, 127.62, 126.63, 63.49. IR (CHCl$_3$) 1619, 1591, 1498, 1342, 1220, 1208, 1083, 790, 776, 733, 729, 700, 599.
HRMS (EI) calcd for C$_{16}$H$_{12}$O$_2$S 268.0558; found: 268.0554.

(4) 2-(Hydroxymethyl)-3-phenyl-4H-sulfonyl-chromen-4-one

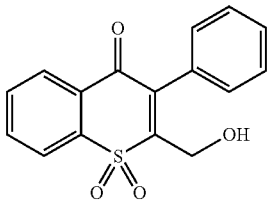

[Chem. 35]

The compound (1.0 mmol, 252 mg) obtained in (3) above and m-chloroperbenzoic acid (70%) (2.1 mmol, 515 mg) were dissolved in methylene chloride (2.0 mL), and the solution was stirred at room temperature for 8 hours. A saturated aqueous sodium thiosulfate solution was poured thereinto to terminate the reaction, and extraction was performed with methylene chloride. The organic layer obtained thereby was washed with saturated sodium bicarbonate water, and dried over magnesium sulfate. Then, the solvents were evaporated under reduced pressure. The residue was purified by silica gel column chromatography, and the title compound (0.85 mmol and 255 mg) was obtained in an 85% yield.
White Solid
$^1$H-NMR (CDCl$_3$/TMS) (ppm) δ: 8.23 (1H, J=8.0, d), 8.12 (1H, J=7.0, d), 7.92 (1H, J=8.0 Hz, 7.5 Hz, dd), 7.53 (1H, J=7.5 Hz, 7.0 Hz, dd), 7.51-7.27 (5H, m), 4.62 (2H, s). $^{13}$C-NMR (CDCl$_3$) δ: 178.60, 147.77, 142.68, 140.01, 134.66, 133.42, 130.59, 129.65, 129.43, 129.14, 129.08, 128.40, 123.07, 57.01. IR (CHCl$_3$) 1720, 1665, 1587, 1574, 1442, 1303, 1217, 1156, 1131, 1065, 1030, 846, 803, 743, 699, 674, 599, 544.
HRMS (EI) calcd for C$_{16}$H$_{12}$O$_2$S 300.0456; found: 300.0457.

(5) (4-oxo-3-phenyl-4H-sulfonylchromen-2-yl)methyl chloroformate

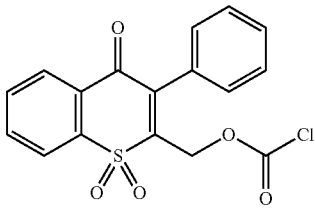
[Chem. 36]

In a two-necked pear-shaped flask, the compound (0.5 mmol, 150 mg) obtained in (3) above and Aliquat (0.05 mmol, 22 mg) were dissolved in tetrahydrofuran (1.5 mL) and toluene (4 mL). Triphosgene (2.5 mmol, 757 mg) and Aliquat (50 mg) were introduced into a reaction tube, and the reaction tube was heated at 80° C. The produced phosgene was used for bubbling through the reaction solution prepared above in the two-necked pear-shaped flask, whose temperature had been adjusted to 0° C. Then, the temperature of the solution was returned to room temperature, and the solution was stirred for 24 hours. After completion of the reaction, nitrogen bubbling was performed to trap the dissolved phosgene in a saturated aqueous sodium hydroxide solution. The obtained solution of the crude reaction product was purified by silica gel column chromatography, and the title compound was obtained in a 97% yield.
White Solid $^1$H-NMR (CDCl$_3$/TMS) (ppm) δ: 8.17 (1H, J=7.9, d), 8.09 (1H, J=7.9, d), 7.89 (1H, J=7.9 Hz, 7.5 Hz, dd), 7.77 (1H, J=7.5 Hz, 7.0 Hz, dd), 7.50-7.47 (3H, m), 7.27-7.25 (2H, m), 5.20 (2H, s). $^{13}$C-NMR (CDCl$_3$) δ: 178.00, 150.02, 145.97, 142.08, 139.66, 134.89, 130.15, 129.97, 128.95, 128.87, 128.78, 128.76, 128.56, 123.15, 63.03.

Production Example 2

(1) 3-(4-Methoxyphenyl)-2-methyl-4H-thiochromen-4-one

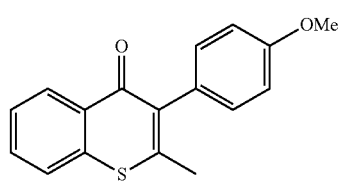
[Chem. 37]

The compound (1.0 mmol, 302 mg) obtained in Production Example 1(1) and dichlorobis(triphenylphosphine)palladium (0.03 mmol, 21 mg), phenylboronic acid (1.3 mmol, 198 mg) and potassium carbonate (4.0 mmol, 552 mg) were dissolved in degassed dimethylformamide (3.2 mL) and water (0.8 mL), and the solution was stirred under a nitrogen atmosphere at 80° C. for 4 hours. After the disappearance of the starting materials was confirmed by thin-layer chromatography, water was poured into the reaction solution to terminate the reaction. The organic substances were extracted with ethyl acetate, the obtained organic layer was dried over magnesium sulfate, and the solvents were evaporated under reduced pressure. The residue was purified by silica gel column chromatography, and the title compound (0.95 mmol, 268 mg) was obtained in a 93% yield.
White Solid $^1$H-NMR (CDCl$_3$) δ: 8.49 (1H, d, J=9.2 Hz), 7.55-7.52 (2H, m), 7.49-7.46 (1H, m), 7.13 (2H, d, J=8.6 Hz), 6.97 (2H, d, J=8.6 Hz), 3.83 (3H, s), 2.25 (3H, s). $^{13}$C-NMR (CDCl$_3$) δ 179.21, 158.82, 147.03, 136.50, 135.84, 131.01, 130.96, 130.87, 129.25, 127.90, 127.18, 125.42, 55.12, 22.49.

(2) 2-(Hydroxymethyl)-3-(4-methoxyphenyl)-4H-thiochromen-4-one

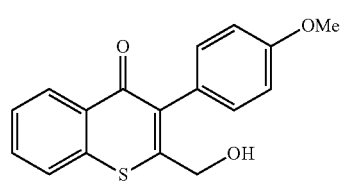
[Chem. 38]

The compound (1.0 mmol, 282 mg) obtained in (1) above and SeO$_2$ (1.2 mmol, 133 mg) were dissolved in 5 mL of chlorobenzene, and the solution was refluxed for 12 hours under a nitrogen atmosphere. After the disappearance of the starting materials was confirmed by NMR, the temperature of the solution was returned to room temperature, and saturated NaHCO$_3$ was poured thereinto to terminate the reaction. The organic substances were extracted with methylene chloride, the obtained organic layer was dried over magnesium sulfate, and the solvents were evaporated under reduced pressure. The residue was passed through a silica-gel column, and directly used in the subsequent reaction. The obtained mixture was dissolved in 2 mL of methanol, to which NaBH$_4$ (1.0 mmol, 38 mg) was added; and under a nitrogen atmosphere, the resulting product was stirred at 0° C. for 2 hours. A saturated ammonium chloride solution was added thereto to terminate the reaction. Then, the organic layer extracted with ethyl acetate was dried over magnesium sulfate, and the solvents were evaporated under reduced pressure. The residue was purified by silica gel column chromatography and recrystallized with hexane/ethyl acetate. Thereby, the title compound (0.41 mmol, 122 mg) was obtained in a two-step yield of 41%.
White Solid $^1$H-NMR (DMSO-d$_6$) δ: 8.30 (1H, d, J=7.9 Hz), 7.91 (1H, d, J=7.9 Hz), 7.72 (1H, dd, J=7.9, 7.9 Hz), 7.58 (1H, dd, J=7.9, 7.9 Hz), 7.10 (2H, d, J=8.6 Hz), 6.97 (2H, d, J=8.6 Hz), 6.03 (1H, t, J=5.8 Hz), 4.36 (2H, d, J=5.8 Hz), 3.78 (3H, s). $^{13}$C-NMR (DMSO-d$_6$) δ: 178.07, 158.62, 155.96, 136.86, 132.39, 131.53, 130.82, 10.39, 128.16, 127.63, 127.55, 127.28, 113.67, 61.81, 55.10. IR (CHCl$_3$) 1590, 1545, 1509, 1438, 1343, 1291, 1247, 1223, 1220, 1208, 1176, 1083, 1034, 822, 790, 781, 773, 762, 790, 739, 725, 669.

HRMS (EI) calcd for C$_{17}$H$_{14}$O$_3$S; 298.0664 found: 298.0666.

(3) 2-(Hydroxymethyl)-3-(4-methoxyphenyl)-4H-sulfonylchromen-4-one

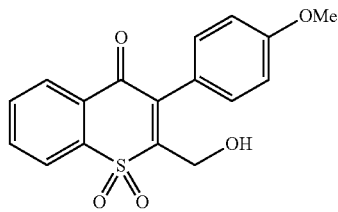

[Chem. 39]

The compound (1.0 mmol, 252 mg) obtained in (2) above and m-chloroperbenzoic acid (70%) (2.1 mmol, 515 mg) were dissolved in methylene chloride (2.0 mL), and the solution was stirred at room temperature for 8 hours. A saturated aqueous sodium thiosulfate solution was poured thereinto to terminate the reaction, and the organic substances were extracted with methylene chloride. The obtained organic layer was washed with saturated sodium bicarbonate water, dried over magnesium sulfate, and the solvents were evaporated under reduced pressure. The residue was purified by silica gel column chromatography, and the title compound (0.85 mmol, 280 mg) was obtained in an 85% yield.
White Solid $^1$H-NMR (CDCl$_3$) δ: 8.21 (1H, d, J=7.9 Hz), 8.09 (1H, d, J=7.9 Hz), 7.89 (1H, dd, J=7.9, 7.9 Hz), 7.78 (1H, dd, J=7.9, 7.9 Hz), 7.35 (2H, d, J=9.2 Hz), 7.00 (2H, d, J=9.2 Hz), 4.63 (2H, s), 3.86 (3H, s). $^{13}$C-NMR (CDCl$_3$) δ: 178.94, 160.63, 147.08, 142.50, 139.96, 134.54, 133.33, 131.18, 129.22, 129.03, 122.99, 122.66, 113.80, 57.01, 55.32. IR (CHCl$_3$) 1667, 1607, 1511, 1442, 1297, 1253, 1208, 1180, 1155, 1128, 1055, 1031, 909, 857, 791, 774, 764, 750, 736, 730, 727, 669, 543.
HRMS (EI) calcd for C$_{17}$H$_{14}$O$_5$S; 330.0562 found: 330.0557.

Production Example 3

(1) 3-(3,5-bis(Trifluoromethyl)phenyl)-2-(hydroxymethyl)-4H-thiochromen-4-one

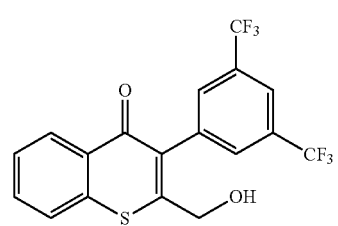

[Chem. 40]

The title compound was obtained as in Production Examples 2(1) and 2(2), except that 3,5-bis(trifluoromethyl)phenylboronic acid was used in place of the phenylboronic acid. The two-step yield of the obtained title compound was 43%.
White Solid $^1$H-NMR (CDCl$_3$) δ: 8.51 (1H, d, J=7.9 Hz), 7.92 (1H, s), 7.72-7.67 (4H, m), 7.60-7.58 (1H, m), 4.55 (2H, s). $^{13}$C-NMR (DMSO-d$_6$) δ: 177.61, 158.03, 138.38, 136.86, 131.98, 131.00, 130.37, 130.18, 130.11, 129.67, 128.10, 128.02, 127.42, 124.48, 122.32, 61.64. IR (CHCl$_3$) 1619, 1591, 1438, 1382, 1279, 1223, 1221, 1213, 1208, 1182, 1141, 904, 790, 774, 766, 753, 733, 706, 669.
HRMS (EI) calcd for C$_{18}$H$_{10}$F$_6$O$_2$S; 404.0306 found: 404.0312.

(2) 3-(3,5-bis(Trifluoromethyl)phenyl)-2-(hydroxymethyl)-4H-sulfonylchromen-4-one

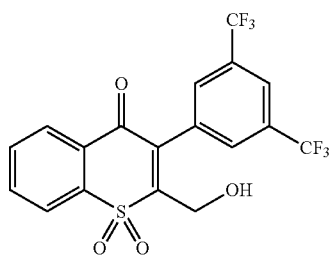

[Chem. 41]

The title compound was obtained as in Production Example 2(3), by using the compound obtained in (1) above.
White Solid $^1$H-NMR (CDCl$_3$) δ: 8.25 (1H, d, J=7.9 Hz), 8.13 (1H, d, J=7.9 Hz), 8.02 (1H, s), 7.96 (1H, dd, J=7.9, 7.9 Hz), 7.92 (2H, s), 7.85 (1H, dd, J=7.9, 7.9 Hz), 4.55 (2H, s). $^{13}$C-NMR (CDCl$_3$) δ: 177.79, 149.68, 139.85, 139.81, 135.22, 133.74, 132.58, 132.00, 131.73, 131.46, 130.20, 129.23, 128.56, 124.04, 123.39, 121.87, 56.54. IR (CHCl$_3$) 2253, 1465, 1379, 1280, 1223, 1208, 1145, 918, 790, 750.
HRMS (EI) calcd for C$_{18}$H$_{10}$F$_6$O$_4$S; 436.0204 found: 436.0204.

Production Example 4

(1) (3-Iodo-4-oxo-4H-thiochromen-2-yl)methyl acetate

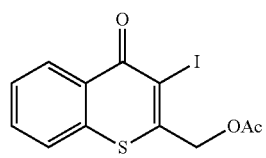

[Chem. 42]

Under a nitrogen atmosphere, 2-(hydroxymethyl)-4H-thiochromen-4-one (10.9 mmol, 2.1 g) was dissolved in 5.0 mL of methylene chloride and 5.0 mL of pyridine, to which acetic anhydride (16.4 mmol, 1.7 g) was added dropwise at 0° C. After the disappearance of the starting materials was confirmed by thin-layer chromatography, the reaction was terminated by the addition of saturated ammonium chloride, and the organic substances were extracted with methylene chloride. The obtained organic layer was dried over magnesium sulfate, and the solvent was evaporated under reduced pressure. The residue was purified by silica gel column chromatography, and then used in the subsequent reaction. The compound (3.2 mmol, 750 mg) obtained earlier, iodine (3.9 mmol, 970 mg) and ceric ammonium nitrate (1.94 g, 3.5 mmol) were dissolved in acetonitrile (30 ml), and the solution was stirred at 60° C. for 5 hours. After the disappearance of the starting materials was confirmed by thin-layer chromatography, the reaction solution was poured into a 10% saturated aqueous sodium thiosulfate solution under ice-cooling to terminate the reaction. The organic substances were extracted with methylene chloride, the obtained organic layer was dried over magnesium sulfate, and the solvent was evaporated under reduced pressure. The residue was purified by silica gel column chromatography, and the title compound (2.7 mmol, 964 mg) was obtained in an 84% yield.
Yellow Solid
$^1$H-NMR (CDCl$_3$) δ: 8.57 (1H, d, J=8.6 Hz), 7.66-7.58 (3H, m), 5.26 (2H, s), 2.26 (3H, s). $^{13}$C-NMR (CDCl$_3$) δ: 175.11, 169.63, 149.93, 136.21, 131.88, 129.90, 128.58, 127.61, 125.74, 100.34, 71.60, 20.58. IR (CHCl$_3$) 1755, 7625, 1592, 1525, 1437, 1375, 1224, 1221, 1213, 1207, 1089, 790, 763, 754, 748, 744, 670.
HRMS (FAB) calcd for C$_{12}$H$_9$IO$_3$S (M$^+$+H); 360.9395 found: 360.9399.

(2) 2-Hydroxymethyl-3-iodo-4H-thiochromen-4-one

[Chem. 43]

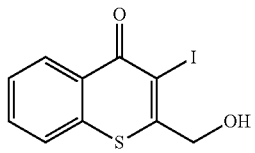

The compound (0.027 mmol, 10 mg) obtained in (1) above was dissolved in methanol, to which potassium carbonate (0.015 mmol, 2.05 mg) was added at 0° C., and the resulting solution was stirred for 1 hour. After the disappearance of the starting materials was confirmed by thin-layer chromatography, a saturated aqueous ammonium chloride solution was added to the reaction solution to terminate the reaction. Then, extraction was performed with methylene chloride, the obtained organic layer was dried over sodium sulfate, and the solvents were evaporated under reduced pressure. The residue was purified by silica gel column chromatography, and the title compound (0.019 mmol, 6.2 mg) was obtained in a 72% yield.
White Solid
$^1$H-NMR (CDCl$_3$) δ: 8.57 (0H, d, J=9.2 Hz), 7.68-7.65 (2H, m), 7.60-7.58 (1H, m), 4.83 (2H, s). $^{13}$C-NMR (DMSO-d$_6$) δ: 174.36, 160.18, 137.08, 131.96, 128.54, 128.53, 127.37, 126.88, 96.49, 70.75. IR (CHCl$_3$) 1620, 1591, 1522, 1436, 1303, 1234, 1220, 1202, 1086, 956, 919, 851, 798, 790, 763, 749, 740, 734, 723, 670.
HRMS (FAB) calcd for C$_{10}$H$_8$IO$_2$S (M$^+$+H); 318.9290 found: 318.9293.

(3) 3-Iodo-4-oxo-4H-thiochromene-2-carbaldehyde

[Chem. 44]

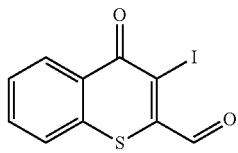

2-Iodoxybenzoic acid (0.56 mmol, 156 mg) was dissolved in 4.0 mL of dimethyl sulfoxide, to which the compound (0.28 mmol, 100 mg) obtained in (2) above was added, and the resulting solution was stirred at room temperature for 1 hour. After the disappearance of the starting materials was confirmed by thin-layer chromatography, water was poured into the reaction solution. Then, the precipitated 2-iodoxybenzoic acid was filtered through a glass filter, and the residue was subjected to extraction with ethyl acetate. The obtained organic layer was dried over sodium sulfate, and the solvents were evaporated under reduced pressure. The resulting product was purified by column chromatography, and the title compound (0.24 mmol, 76 mg) was obtained in an 86% yield.
Yellow Solid
$^1$H-NMR (CDCl$_3$) δ: 10.23 (1H, s), 8.56 (1H, d, J=7.3 Hz), 7.73-7.72 (2H, m), 7.64-7.63 (1H, m). $^{13}$C-NMR (CDCl$_3$) δ: 193.94, 175.35, 142.64, 135.06, 131.52, 128.86, 127.68, 127.03, 125.36, 109.72. IR (CHCl$_3$) 1693, 1633, 1223, 1216, 1210, 1208, 1081, 1023, 791, 789, 781, 770, 759, 750, 745, 740, 730, 722, 629.
HRMS (FAB) calcd for C$_{10}$H$_8$IO$_2$S; 315.9055 found: 315.9058.

(4) Suzuki-Miyaura Coupling

[Chem. 45]

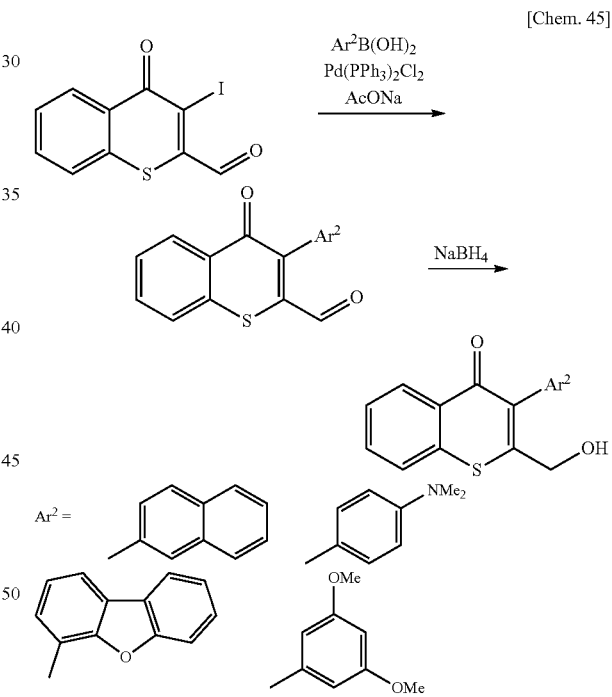

The compound (1.0 mmol) obtained in (3) above, dichlorobis triphenylphosphine palladium (0.03 mmol), various boronic acids (1.5 mmol) and sodium acetate (4.0 mmol) were dissolved in degassed dimethylformamide (3.2 mL) and water (0.8 mL), and the solution was stirred under a nitrogen atmosphere at 50° C. for 2 hours. After the disappearance of the starting materials was confirmed by thin-layer chromatography, water was poured into the reaction solution to terminate the reaction. The organic substances were extracted with ethyl acetate, the obtained organic layer was dried over magnesium sulfate, and the solvents were evaporated under reduced pressure. The residue was purified by silica gel column chromatography and then used in the subsequent reaction. The obtained mixture was dissolved in 2 mL of methanol, to which sodium borohydride (1.0 mmol, 38 mg) was added, and the resulting solution was stirred under a nitrogen atmosphere at 0° C. for 2 hours. A saturated aqueous ammonium chloride solution was added thereto to terminate the reaction, after which the organic substances were extracted with ethyl acetate. The obtained organic layer was dried over magnesium sulfate, and the solvents were evaporated under reduced pressure. The residue was purified by silica gel column chromatography, and the title compound was obtained.

2-(Hydroxymethyl)-3-(naphthalen-2-yl)-4H-thiochromen-4-one

[Chem. 46]

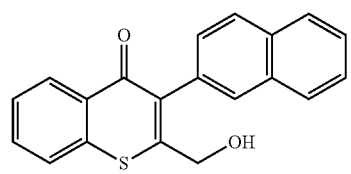

White Solid $^1$H-NMR (CDCl$_3$) δ: 8.49 (1H, d, J=7.3 Hz), 7.83 (2H, t, J=8.9 Hz), 7.75 (1H, d, J=7.9 Hz), 7.62-7.60 (2H, m), 7.62-7.60 (3H, m), 7.52-7.44 (3H, m), 7.22 (1H, dd, J=8.6, 1.8 Hz), 4.47 (2H, s). $^{13}$C-NMR (CDCl$_3$) δ: 179.46, 153.77, 137.06, 134.14, 133.34, 132.86, 132.84, 131.29, 131.03, 129.13, 128.45, 128.29, 127.99, 127.71, 127.58, 127.25, 126.65, 126.29, 126.14, 63.33.

HRMS (EI) calcd for C$_{20}$H$_{14}$O$_2$S; 318.0715 found: 318.0715.

3-(4-(Dimethylamino)phenyl)-2-(hydroxymethyl)-4H-thiochromen-4-one

[Chem. 47]

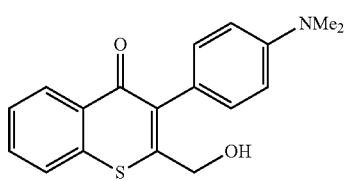

Yellow Solid $^1$H-NMR (CDCl$_3$) δ: 8.51 (1H, d, J=7.9 Hz), 7.64 (1H, d, J=6.7 Hz), 7.60-7.58 (1H, m), 7.52-7.49 (1H, m), 7.06 (2H, d, J=8.6 Hz), 6.79 (2H, d, J=8.6 Hz), 4.59 (2H, s), 2.98 (6H, s). $^{13}$C-NMR (CDCl$_3$) δ: 179.72, 151.56, 150.10, 136.87, 134.87, 131.20, 131.09, 130.26, 129.30, 127.39, 126.53, 112.61, 63.72, 40.57. IR (CHCl$_3$) 1668, 1465, 1381, 1305, 1222, 1208, 1156, 1128, 1097, 913, 790, 766, 739, 726, 722, 669, 650, 544.

HRMS (FAB) calcd for C$_{18}$H$_{17}$NO$_2$S; 311.0980 found: 311.0982.

3-(Dibenzo[b,d]furan-4-yl)-2-(hydroxymethyl)-4H-thiochromen-4-one

[Chem. 48]

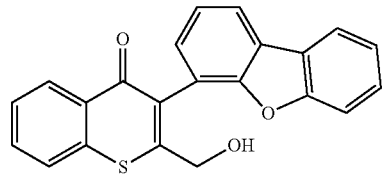

White Solid $^1$H-NMR (CDCl$_3$) δ: 8.49 (1H, d, J=7.3 Hz), 7.92 (2H, d, J=6.7 Hz), 7.63-7.60 (2H, m), 7.52-7.50 (1H, m), 7.43-7.30 (4H, m), 7.24 (1H, t, J=8.2 Hz), 4.49 (2H, d, J=15.3 Hz), 4.42 (2H, d, J=15.3 Hz). $^{13}$C-NMR (CDCl$_3$) δ: 178.80, 155.90, 153.54, 137.05, 131.34, 130.94, 129.21, 128.66, 127.64, 127.25, 126.66, 124.64, 124.21, 123.02, 122.90, 120.73, 120.69, 119.25, 111.73, 63.35. IR (CHCl$_3$) 1450, 1412, 1349, 1222, 12089, 1190, 1092, 909, 834, 788, 775, 764, 752, 741, 735, 733, 723.

HRMS (EI) calcd for C$_{22}$H$_{14}$O$_2$S; 358.0664 found: 358.0665.

3-(3,5-Dimethoxyphenyl)-2-(hydroxymethyl)-4H-thiochromen-4-one

[Chem. 49]

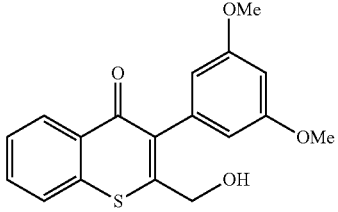

White Solid $^1$H-NMR (DMSO-d$_6$) δ: 8.32 (1H, d, J=7.9 Hz), 7.94 (1H, d, J=7.9 Hz), 7.75 (1H, dd, J=7.9, 7.9 Hz), 7.61 (1H, dd, J=7.9, 7.9 Hz), 6.51 (1H, dd, J=2.4, 2.4 Hz), 6.34 (2H, d, J=2.4 Hz), 6.06 (1H, t, J=5.5 Hz), 4.39 (2H, d, J=5.5 Hz), 3.75 (6H, s). $^{13}$C-NMR (DMSO-d$_6$) δ: 177.68, 160.43, 156.18, 137.74, 136.84, 132.67, 131.61, 130.40, 128.11, 127.70, 127.32, 107.41, 99.52, 61.60, 55.25. IR (CHCl$_3$) 1592, 1456, 1438, 1422, 1328, 1292, 1224, 1221, 1207, 1156, 1085, 1064, 835, 790, 746, 735, 727, 669.

HRMS (FAB) calcd for C$_{18}$H$_{16}$O$_4$S; 328.0769 found: 328.0768.

(5) Oxidation Reaction

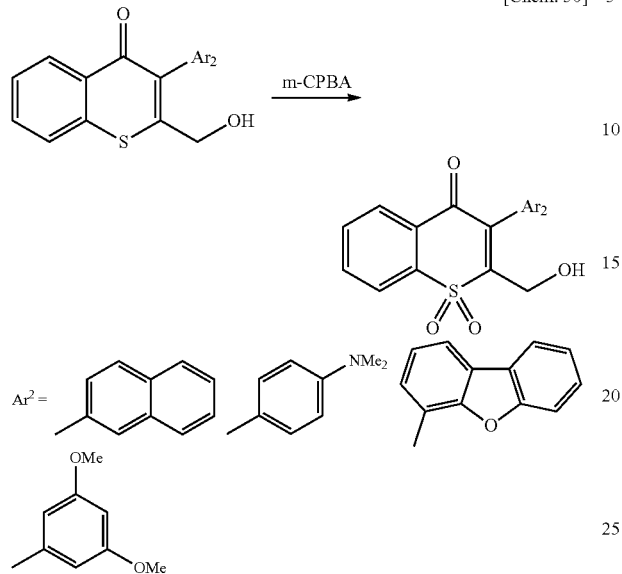

[Chem. 50]

The compound (1.0 mmol) obtained in (4) above and m-chloroperbenzoic acid (70%) (2.1 mmol) were dissolved in chloroform (2.0 mL), and the solution was stirred at room temperature for 8 hours. A saturated aqueous sodium thiosulfate solution was poured thereto to terminate the reaction, and the organic substances were extracted with methylene chloride. The obtained organic layer was washed with saturated sodium bicarbonate water, dried over magnesium sulfate, and the solvents were evaporated under reduced pressure. The residue was purified by silica gel column chromatography, and the title compound was obtained.

2-(Hydroxymethyl)-3-(naphthalen-2-yl)-4H-sulfonylchromen-4-one

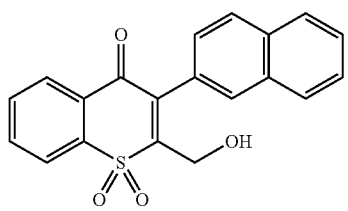

[Chem. 51]

White Solid $^1$H-NMR (CDCl$_3$) δ: 8.23 (1H, d, J=7.9 Hz), 8.13 (1H, d, J=7.9 Hz), 7.95-7.89 (5H, m), 7.80 (1H, dd, J=7.9, 7.9 Hz), 7.59-7.54 (2H, m), 7.43 (1H, dd, J=8.6, 1.2 Hz), 4.65 (2H, s). $^{13}$C-NMR (CDCl$_3$) δ: 178.77, 148.03, 142.75, 140.06, 134.68, 133.47, 133.42, 132.65, 129.33, 129.16, 129.09, 128.51, 128.15, 128.03, 127.77, 127.30, 126.74, 126.48, 123.11, 57.07. IR (CHCl$_3$) 1668, 1465, 1381, 1305, 1222, 1208, 1156, 1128, 1097, 913, 790, 766, 739, 726, 722, 669, 650, 544.

3-(Dibenzo[b,d]furan-4-yl)-2-(hydroxymethyl)-4H-sulfonylchromen-4-one

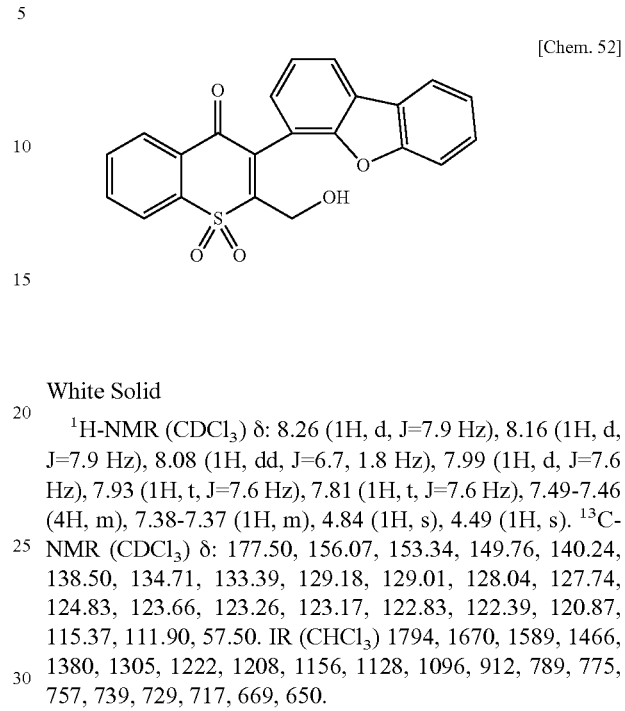

[Chem. 52]

White Solid $^1$H-NMR (CDCl$_3$) δ: 8.26 (1H, d, J=7.9 Hz), 8.16 (1H, d, J=7.9 Hz), 8.08 (1H, dd, J=6.7, 1.8 Hz), 7.99 (1H, d, J=7.6 Hz), 7.93 (1H, t, J=7.6 Hz), 7.81 (1H, t, J=7.6 Hz), 7.49-7.46 (4H, m), 7.38-7.37 (1H, m), 4.84 (1H, s), 4.49 (1H, s). $^{13}$C-NMR (CDCl$_3$) δ: 177.50, 156.07, 153.34, 149.76, 140.24, 138.50, 134.71, 133.39, 129.18, 129.01, 128.04, 127.74, 124.83, 123.66, 123.26, 123.17, 122.83, 122.39, 120.87, 115.37, 111.90, 57.50. IR (CHCl$_3$) 1794, 1670, 1589, 1466, 1380, 1305, 1222, 1208, 1156, 1128, 1096, 912, 789, 775, 757, 739, 729, 717, 669, 650.

HRMS (EI) calcd for C$_{22}$H$_{14}$O$_5$S; 390.0562 found: 390.0561.

3-(3,5-Dimethoxyphenyl)-2-(hydroxymethyl)-4H-sulfonylchromen-4-one

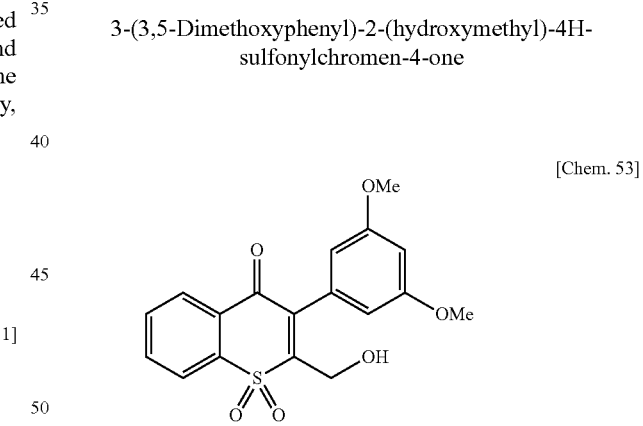

[Chem. 53]

White Solid $^1$H-NMR (CDCl$_3$) δ: 8.22 (1H, d, J=7.9 Hz), 8.10 (1H, d, J=7.9 Hz), 7.90 (1H, dd, J=7.9, 7.9 Hz), 7.80 (1H, dd, J=7.9, 7.9 Hz), 6.56 (1H, t, J=2.1 Hz), 6.49 (2H, d, J=2.1 Hz), 4.63 (2H, s), 3.81 (6H, s). $^{13}$C-NMR (CDCl$_3$) δ: 178.41, 160.71, 148.01, 142.63, 140.06, 134.67, 133.42, 132.34, 129.16, 129.09, 123.11, 107.39, 101.74, 57.02, 55.50. IR (CHCl$_3$) 1670, 1591, 1456, 1425, 1298, 1223, 1214, 1208, 1157, 1129+, 1065, 1013, 840, 789, 755, 729, 690, 541.

HRMS (FAB) calcd for C$_{18}$H$_{16}$O$_6$S; 360.0668 found: 360.0665

Production Example 5

(1) 2-Iodo-3-methyl-1H-benzo[f]thiochromen-1-one

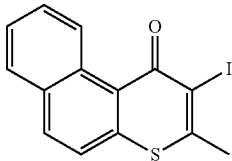

[Chem. 54]

3-Methyl-1H-benzo[f]thiochromen-1-one (1.0 mmol, 176 mg), iodine (1.2 mmol, 305 mg) and ceric ammonium nitrate (1.1 mmol, 603 mg) were dissolved in acetonitrile (4.0 mL), and the solution was stirred under a nitrogen atmosphere at 60° C. for 4 hours. After the disappearance of the starting materials was confirmed by thin-layer chromatography, the reaction solution was poured into a solution of a 10% saturated aqueous sodium thiosulfate solution under ice-cooling to terminate the reaction. The organic substances were extracted with methylene chloride, the obtained organic layer was dried over magnesium sulfate, and the solvents were evaporated under reduced pressure. The residue was purified by silica gel column chromatography, and the title compound (0.74 mmol, 260 mg) was obtained in a 74% yield.
Yellow Solid
$^1$H-NMR (CDCl$_3$) δ: 10.01 (1H, d, J=8.6 Hz), 7.86 (1H, d, J=9.2 Hz), 7.80 (1H, d, J=7.9 Hz), 7.69 (1H, dd, J=7.9, 7.9 Hz), 7.58 (1H, dd, J=8.6, 7.9 Hz), 7.36 (1H, d, J=9.2 Hz), 2.56 (3H, s). $^{13}$C-NMR (CDCl$_3$) δ: 176.92, 147.69, 139.08, 132.95, 132.66, 131.70, 129.03, 128.35, 127.32, 127.17, 121.96, 121.83, 108.60, 31.73. IR (CHCl$_3$) 1607, 1561, 1505, 1212, 1117, 909, 814, 787, 781, 766, 755, 748, 742, 730, 727, 670, 668, 650.
HRMS (EI) calcd for C$_{14}$H$_9$IOS; 351.9419 found: 351.9419

(2) 3-Methyl-2-phenyl-1H-benzo[f]thiochromen-1-one

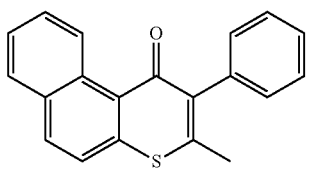

[Chem. 55]

The compound (1.0 mmol, 352 mg) obtained in (1) above, dichloro triphenylphosphine palladium (0.03 mmol, 21 mg), phenylboronic acid (1.3 mmol, 159 mg) and potassium carbonate (4.0 mmol, 552 mg) were dissolved in degassed dimethylformamide (3.2 mL) and water (0.8 mL), and the resulting solution was stirred under a nitrogen atmosphere at 80° C. for 4 hours. After the disappearance of the starting materials was confirmed by thin-layer chromatography, water was poured into the reaction solution to terminate the reaction. The organic substances were extracted with ethyl acetate, the obtained organic layer was dried over magnesium sulfate, and the solvents were evaporated under reduced pressure. The residue was purified by silica gel column chromatography, and the title compound (0.98 mmol, 296 mg) was obtained in a 93% yield.
Yellow Solid
$^1$H-NMR (CDCl$_3$) δ: 10.03 (1H, d, J=8.6 Hz), 7.88 (1H, d, J=8.6 Hz), 7.81 (1H, d, J=7.9 Hz), 7.63-7.61 (1H, m), 7.55-7.54 (1H, m), 7.45-7.38 (4H, m), 7.24 (2H, d, J=6.7 Hz), 2.20 (3H, s). $^{13}$C-NMR (CDCl$_3$) δ: 181.34, 143.10, 139.08, 136.58, 132.58, 132.48, 132.35, 132.15, 132.07, 129.67, 128.63, 128.39, 128.24, 127.45, 127.06, 126.81, 125.97, 122.94, 21.67. IR (CHCl$_3$) 1710, 1617, 1580, 1505, 1439, 1424, 1378, 1360, 1339, 1294, 1222, 1209, 1197, 1162, 1116, 908, 814, 787, 771, 757, 739, 727, 721, 700, 649.
HRMS (EI) calcd for C$_{20}$H$_{14}$OS; 302.0765 found: 302.0765.

(3) 3-(Hydroxymethyl)-2-phenyl-1H-benzo[f]thiochromen-1-one

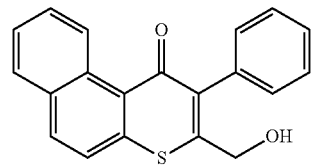

[Chem. 56]

Under a nitrogen atmosphere, the compound (0.33 mmol, 100 mg) obtained in (2) above, NBS (58 mg, 0.39 mmol) and azobisisobutyronitrile (5.0 mg) were dissolved in carbon tetrachloride (3.0 mL), and the resulting solution was refluxed overnight. A nuclear magnetic resonance spectrum confirmed the presence of a compound (corresponding to the compound (19) in this specification) in which the allylic position was brominated; the compound was directly used in the subsequent reaction. This compound and silver carbonate (0.55 mmol, 150 mg) were dissolved in dioxane (5.0 mL) and water (2.0 mL), and the resulting solution was refluxed for three days.
Upon confirmation of the formation of a compound by NMR, the silver carbonate was removed by filtration, and the solvents were concentrated under reduced pressure. The residue was purified by silica gel column chromatography, and the title compound (0.31 mmol, 9.8 mg) was obtained in a two-step yield of 11%.
Yellow Solid
$^1$H-NMR (CDCl$_3$) δ: 10.00 (1H, d, J=9.2 Hz), 7.96 (1H, d, J=8.6 Hz), 7.86 (1H, d, J=7.9 Hz), 7.65-7.56 (3H, m), 7.46 (2H, dd, J=7.9, 7.9 Hz), 7.40-7.39 (1H, m), 7.22-7.21 (2H, m), 4.51 (2H, s). $^{13}$C-NMR (CDCl$_3$) δ: 181.42, 148.87, 139.77, 137.14, 135.83, 132.73, 132.32, 129.40, 128.83, 128.71, 128.37, 128.00, 127.14, 127.10, 126.12, 123.94, 62.97. IR (CHCl$_3$) 1593, 1506, 1424, 1339, 1295, 1223, 1221, 1211, 1208, 1196, 1115, 967, 899, 814, 787, 780, 770, 760, 747, 740, 701, 669, 593.
HRMS (EI) calcd for C$_{20}$H$_{14}$O$_2$S; 318.0715 found: 318.0718.

(4) 3-(Hydroxymethyl)-2-phenyl-1H-benzo[f]sulfonylchromen-1-one

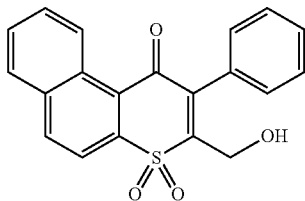
[Chem. 57]

The compound (0.1 mmol, 32 mg) obtained in (2) above and m-chloroperbenzoic acid (70%) (0.21 mmol, 72 mg) were dissolved in methylene chloride (2.0 mL), and the resulting solution was stirred at room temperature for 8 hours. A saturated aqueous sodium thiosulfate solution was poured thereinto to terminate the reaction, and extraction was performed with methylene chloride. The obtained organic layer was washed with saturated sodium bicarbonate water, dried over magnesium sulfate, and the solvents were evaporated under reduced pressure. The residue was purified by silica gel column chromatography, and the title compound (0.081 mmol, 28 mg) was obtained in an 81% yield.
Yellow Solid
$^1$H-NMR (CDCl$_3$) δ: 9.00 (1H, d, J=8.6 Hz), 8.34 (1H, d, J=8.6 Hz), 8.12 (1H, d, J=8.6 Hz), 7.98 (1H, d, J=8.6 Hz), 7.75-7.71 (2H, m), 7.52-7.47 (5H, m), 4.63 (2H, s). $^{13}$C-NMR (CDCl$_3$) d: 182.30, 145.07, 145.02, 140.20, 136.02, 135.43, 131.12, 130.85, 129.72, 129.55, 129.48, 129.24, 129.02, 128.50, 127.42, 126.90, 118.52, 117.68, 56.98. IR (CHCl$_3$) 1794, 1465, 1380, 1301, 1222, 1209, 1128, 1096, 904, 788, 768, 756, 744, 730, 719, 669, 650, 543.
HRMS (EI) calcd for $C_{20}H_{14}O_4S$; 350.0613 found: 350.0617.

Production Example 6

Synthesis of Diol Protecting Group

(1) Methyl 2-(4-oxo-3-phenyl-4H-thiochromen-2-yl)acetate

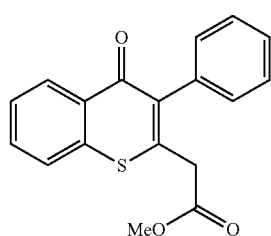
[Chem. 58]

Under a nitrogen atmosphere, diisopropylamine (0.14 mL) was dissolved in tetrahydrofuran (1.0 mL), to which 0.65 mL of n-butyllithium (a 1.6 M hexane solution) was added dropwise at 0° C. To the resulting solution, which was cooled to −78° C., the compound (2-methyl-3-phenyl-4H-thiochromen-4-one) (0.5 mmol, 126 mg) obtained in Production Example 1(2), which had been dissolved in hexamethylphosphoramide (1.0 mL), was added dropwise, and the resulting solution was stirred for 5 min. Additionally, cyanomethyl formate (44 μL), which had been dissolved in tetrahydrofuran (0.5 mL), was further added thereto dropwise, and the resulting solution was stirred for another 30 min. The reaction was terminated by the addition of saturated ammonium chloride. The organic substances were extracted with ethyl acetate, and the obtained organic layer was dried over magnesium sulfate. The solvents were evaporated under reduced pressure, the residue was purified by silica gel column chromatography, and the title compound (0.34 mmol, 107 mg) was obtained.
White Solid
$^1$H-NMR (CDCl$_3$) δ: 8.51 (1H, d, J=7.9 Hz), 7.61-7.59 (2H, m), 7.54-7.53 (1H, m), 7.44-7.43 (2H, m), 7.40-7.38 (1H, m), 7.20 (2H, d, J=6.7 Hz), 3.66 (3H, s), 3.55 (2H, s). $^{13}$C-NMR (CDCl$_3$) δ: 179.43, 169.12, 142.64, 138.31, 136.40, 135.33, 131.50, 131.03, 129.64, 129.48, 128.59, 128.06, 127.66, 125.86, 52.55, 40.87. IR (CHCl$_3$) 2253, 1793, 1740, 1618, 1592, 1463, 1437, 1380, 1344, 1266, 1222, 1209, 1173, 1096, 911, 791, 753, 729, 709, 650, 619, 543.
HRMS (EI) calcd for $C_{18}H_{14}O_3S$ 310.0664; found: 310.0675

(2) Methyl-2-hydroxy-2-(4-oxo-3-phenyl-4H-thiochromen-2-yl)acetate

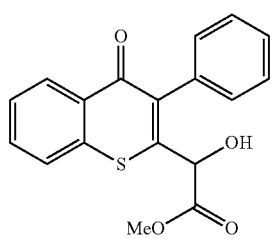
[Chem. 59]

Under a nitrogen atmosphere, the compound obtained in (1) above (0.16 mmol, 50 mg) was dissolved in tetrahydrofuran (3.0 mL), and the solution was cooled to −78° C. Then, 0.24 mL of lithium hexamethyldisilazide (a 1.0 M solution) was added thereto dropwise, and stirred for 10 min. A Davis reagent (0.32 mmol, 84 mg) was added to the resulting solution, and stirred for 30 min. After the disappearance of the starting materials was confirmed by thin-layer chromatography, the reaction was terminated by adding a saturated aqueous ammonium solution to the reaction solution. Then, the organic substances were extracted with ethyl acetate, and the obtained organic layer was dried over magnesium sulfate. The solvents were evaporated under reduced pressure, the residue was purified by silica gel column chromatography, and the title compound (0.15 mmol, 50 mg) was obtained in a 95% yield.
White Solid
$^1$H-NMR (CDCl$_3$) δ: 8.49 (1H, d, J=7.9 Hz), 7.63-7.61 (2H, m), 7.54-7.52 (1H, m), 7.46-7.45 (3H, m), 7.42-7.40 (2H, m), 7.31-7.29 (4H, m), 5.24 (1H, d, J=3.7 Hz), 3.80 (3H, s), 3.64 (1H, d, J=4.3 Hz). $^{13}$C-NMR (CDCl$_3$) δ: 179.70, 171.85, 147.74, 137.85, 136.02, 135.02, 131.66, 130.89, 129.36, 128.12, 127.66, 126.57, 71.47, 53.76. IR (CHCl$_3$) 2990, 2904, 2610, 2253, 1793, 1738, 1622, 1594, 1465, 1380, 1223, 1208, 1165, 1096, 920, 790, 758, 748, 739, 729, 726, 651, 620, 641.
HRMS (EI) calcd for, $C_{18}H_{14}O_2S$; 326.0613; found: 326.0619.

(3) 2-(1,2-Dihydroxyethyl)-3-phenyl-4H-thio-chromen-4-one

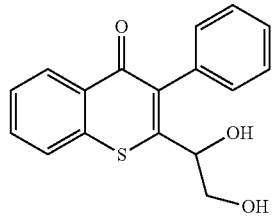
[Chem. 60]

Under a nitrogen atmosphere, lithium aluminium hydride (1.7 mg, 0.045 mg) was dissolved in tetrahydrofuran (0.5 mL), to which the compound (0.06 mmol, 20 mg) obtained in (2) above, which had been dissolved in tetrahydrofuran (1.0 mL), was added dropwise at −78° C. After the disappearance of the starting materials was confirmed by thin-layer chromatography, the reaction was terminated by the addition of 1 N hydrochloric acid, and the organic substances were extracted with ethyl acetate. The obtained organic layer was dried over magnesium sulfate, the solvents were evaporated under reduced pressure, the residue was purified by silica gel column chromatography, and an aldehyde product was obtained. The obtained aldehyde product was dissolved in methanol (1.0 mL), and the resulting solution was stirred with sodium borohydride (0.06 mmol, 2.3 mg) at 0° C. for 1 hour. The reaction was terminated by the addition of a saturated aqueous ammonium chloride solution. Thereafter, the organic substances were extracted with ethyl acetate, and the obtained organic layer was dried over magnesium sulfate. The solvents were evaporated under reduced pressure, the residue was purified by silica gel column chromatography, and the title compound (0.02 mmol, 5.3 mg) was obtained in a 30% yield.
White Solid
$^1$H-NMR (CDCl$_3$) δ: 8.48 (1H, d, J=7.9 Hz), 7.67 (1H, d, J=7.9 Hz), 7.63 (1H, dd, J=7.9, 7.9 Hz), 7.53 (1H, dd, J=7.9, 7.9 Hz), 7.46-7.38 (3H, m), 7.20-7.18 (2H, m), 4.89-4.88 (1H, m), 3.71-3.66 (2H, m), 2.94 (1H, d, J=3.7 Hz, OH), 1.90 (1H, dd, J=6.4, 6.4 Hz, OH). $^{13}$C-NMR (CDCl$_3$) δ: 179.72, 154.33, 137.25, 135.50, 135.11, 131.47, 130.71, 129.00, 128.78, 127.98, 127.65, 126.71, 72.45, 65.72. IR (CHCl$_3$) 2990, 2904, 2627, 2421, 2253, 1793, 1644, 1562, 1465, 1380, 1222, 1209, 1096, 841, 787, 742, 727, 650, 620, 542.
HRMS (EI) calcd for C17H14O3S, 298.0664; found: 198.0669.

(4) 2-(1,2-Dihydroxyethyl)-3-phenyl-4H-sulfonyl-chromen-4-one

[Chem. 61]

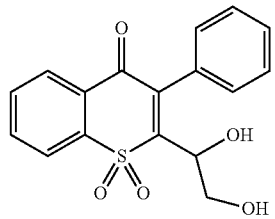

The compound (1.0 mmol, 298 mg) obtained in (3) above and m-chloroperbenzoic acid (70%) (2.1 mmol, 516 mg) were dissolved in methylene chloride (2.0 mL), and the solution was stirred at room temperature for 8 hours. A saturated aqueous sodium thiosulfate solution was poured thereinto to terminate the reaction, and the organic substances were extracted with ethyl acetate. The obtained organic layer was washed with saturated sodium bicarbonate water, dried over magnesium sulfate, and the solvents were evaporated under reduced pressure. The residue was purified by silica gel column chromatography, and the title compound (0.85 mmol, 280 mg) was obtained.
White Solid
$^1$H-NMR (CDCl$_3$) δ: 8.13 (1H, d, J=7.9 Hz), 8.09 (1H, d, J=7.9 Hz), 7.88 (1H, dd, J=7.9, 7.9 Hz), 7.78 (1H, dd, J=7.9, 7.9 Hz), 7.47 (3H, m), 7.26 (2H, m), 4.78 (1H, m), 4.06 (1H, m), 3.96 (1H, m), 3.39 (1H, m, OH), 2.63 (1H, m, OH).
$^{13}$C-NMR (CDCl$_3$) δ: 178.63, 148.66, 143.92, 140.61, 134.69, 133.47, 131.15, 129.53, 129.06, 129.04, 128.92, 128.61, 122.83, 72.58, 64.46. IR (CHCl$_3$) 2253, 1794, 1731, 1668, 1466, 1380, 1307, 1222, 1208, 1155, 1128, 1096, 906, 790, 727, 719, 650, 541.
HRMS (FAB) calcd for C$_{17}$H$_{14}$O$_5$S (M$^+$+Na), 353.0460; found: 353.0468.

I. Protection and Deprotection of Amino Group

Example I-1

Synthesis of Protected Amine

Under a nitrogen atmosphere, various amines (0.1 mmol) were dissolved in methylene chloride (1.0 mL) and pyridine (1.0 mL), to which the compound (1.5 mmol) obtained in Production Example 1(5), which had been dissolved in 0.5 mL of methylene chloride, was added dropwise at 0° C., and the solution was stirred at room temperature for 1 hour. After the reaction product was confirmed by thin-layer chromatography, water was added thereto to terminate the reaction. Then, the organic substances were extracted with methylene chloride, the obtained organic layer was dried over magnesium sulfate, and the solvents were evaporated under reduced pressure. The residue was purified by silica gel column chromatography, and the compounds shown below were obtained.

(4-Oxo-3-phenyl-4H-sulfonylchromen-2-yl)methyl butyl carbamate

[Chem. 62]

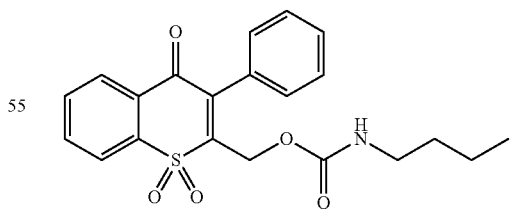

Yield: 96%
Yellow Solid
$^1$H-NMR (CDCl$_3$) δ: 8.18 (1H, d, J=7.9 Hz), 8.11 (1H, d, J=7.3 Hz), 7.88 (1H, dd, J=7.9, 7.3 Hz), 7.77 (1H, dd, J=7.9, 7.3 Hz), 7.47-7.46 (3H, m), 7.28-7.26 (2H, m), 5.05 (2H, s), 4.84 (1H, s), 3.17 (2H, dd, J=7.3, 6.7 Hz), 1.47 (2H, m), 1.32 (2H, m), 0.91 (3H, t, J=7.3 Hz).

$^{13}$C-NMR (CDCl$_3$) δ: 178.63, 154.96, 145.66, 143.82, 140.89, 134.68, 133.18, 131.04, 129.64, 129.10, 129.04, 128.88, 128.48, 123.11, 58.71, 40.99, 31.84, 19.82, 13.70.

IR (CHCl$_3$) 1732, 1669, 1589, 1516, 1428, 1312, 1224, 1161, 1077, 699, 600, 535

HRMS (FAB) calcd for C$_{21}$H$_{21}$NO$_5$S (M$^+$+Na) 422.1038; found: 422.1042

(4-Oxo-3-phenyl-4H-sulfonylchromen-2-yl)methyl diethylcarbamate

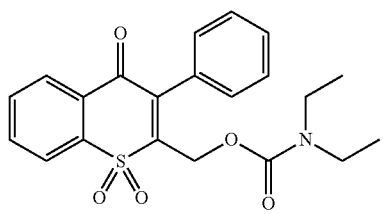

Yield: 91%
Yellow Solid $^1$H-NMR (CDCl$_3$) δ: 8.18 (1H, d, J=7.9 Hz), 8.11 (1H, d, J=7.9 Hz), 7.88 (1H, dd, J=7.9, 7.9 Hz), 7.76 (1H, dd, J=7.9, 7.9 Hz), 7.47-7.46 (3H, m), 7.28-7.26 (2H, m), 5.06 (2H, s), 3.29 (4H, m), 1.15 (3H, t, J=6.7 Hz), 1.12 (3H, t, J=4.5 Hz).

$^{13}$C-NMR (CDCl$_3$) δ: 178.59, 154.44, 146.00, 143.48, 141.11, 134.62, 133.06, 131.12, 129.58, 129.04, 128.98, 128.81, 128.47, 123.04, 59.24, 41.99, 41.36, 13.93, 13.31.

IR (CHCl$_3$) 1738, 1701, 1669, 1590, 1476, 1428, 1381, 1313, 1271, 1169, 1077, 906, 856, 541, 524.

HRMS (FAB) calcd for C$_{21}$H$_{21}$NO$_5$S (M$^+$+Na) 422.1038; found: 422.1036

Benzyl(((4-oxo-3-phenyl-4H-sulfonylchromen-2-yl)methoxy)carbonylamino)-3-phenyl propanoate

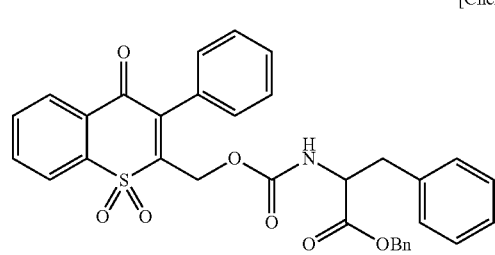

Yield: 95%
Yellow Solid $^1$H-NMR (CDCl$_3$) δ: 8.15 (1H, d, J=7.3 Hz), 8.08 (1H, d, J=7.3 Hz), 7.84 (1H, dd, J=7.9, 7.3 Hz), 7.72 (1H, dd, J=7.3, 7.9 Hz), 7.44 (3H, m), 7.42-7.41 (3H, m), 7.34-7.32 (3H, m), 7.27-7.20 (7H, m), 7.04-7.02 (2H, m), 5.45 (1H, d, J=7.9 Hz), 5.11 (1H, d, J=12.8 Hz), 5.11 (2H, s), 4.97 (1H, d, J=12.8 Hz), 4.64 (1H, m), 3.08 (2H, m, J=5.5 Hz).

$^{13}$C-NMR (CDCl$_3$) δ: 178.45, 170.76, 154.03, 144.95, 144.12, 140.59, 135.29, 134.89, 134.59, 133.07, 130.79, 129.52, 129.30, 128.96, 128.90, 128.74, 128.47, 128.40, 128.31, 126.97, 123.01, 67.12, 58.53, 54.89

IR (CHCl$_3$) 1731, 1668, 1589, 1507, 1443, 1389, 1313, 1233, 1223, 1208, 1162, 1139, 1078, 853, 699, 666, 543, 524.

HRMS (FAB) calcd for C$_{33}$H$_{27}$NO$_7$S (M$^+$+Na) 604.1406; found: 604.1399 tert-Butyl 3-methyl-2-(((4-oxo-3-phenyl-4H-sulfonylchromen-2-yl)methoxy)carbonylamino)butanoate

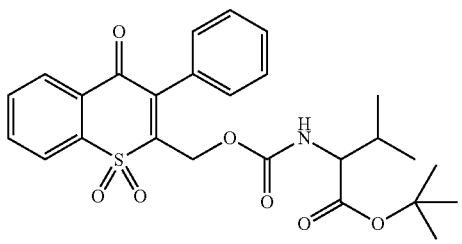

Yield: 94%
Yellow Solid $^1$H-NMR (CDCl$_3$) δ: 8.16 (1H, d, J=7.3 Hz), 8.10 (1H, d, J=7.9 Hz), 7.87 (1H, dd, J=7.9, 7.3 Hz), 7.76 (1H, dd, J=7.3, 7.3 Hz), 7.45-7.44 (3H, m), 7.28-7.26 (2H, m), 5.46 (1H, d, J=8.5 Hz), 5.15 (1H, d, J=13.4 Hz), 4.96 (1H, d, J=12.8 Hz), 4.13-4.09 (1H, m), 2.17 (1H, m), 1.46 (9H, s), 0.95 (3H, d, J=6.7 Hz), 0.89 (3H, d, J=7.3 Hz).

$^{13}$C-NMR (CDCl$_3$) δ: 178.59, 170.55, 154.61, 145.21, 143.96, 140.64, 134.55, 133.03, 129.45, 128.94, 128.90, 128.69, 128.29, 123.00, 81.83, 59.37, 58.35, 31.34, 18.64, 17.27

HRMS (FAB) calcd for C$_{26}$H$_{29}$NO$_7$S (M$^+$+Na) 522.1562; found: 522.1560

(S)-Benzyl 2-((S)-3-methyl-2(((4-oxo-3-phenyl-4H-sulfonylchromen-2-yl)methoxy)carbonylamino)butaneamide)-3-phenyl propanoate

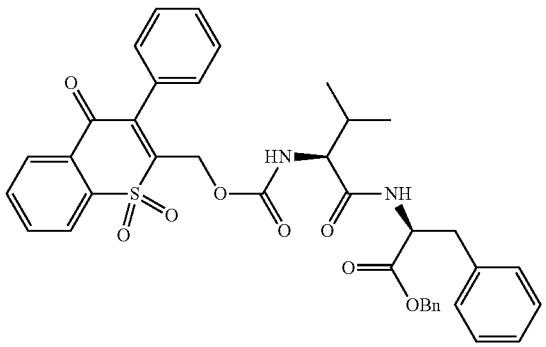

Yield: 81%
White Solid $^1$H-NMR (CDCl$_3$) δ: 8.16 (1H, d, J=7.9 Hz), 8.07 (1H, d, J=7.3 Hz), 7.85 (1H, dd, J=7.9, 7.3 Hz), 7.74 (1H, dd, J=7.9, 7.3 Hz), 7.45 (3H, m), 7.33-7.17 (10H, m), 7.01 (2H, m), 6.57 (1H, d, J=7.3 Hz), 5.40 (1H, d, J=8.6 Hz), 5.11 (1H, d, J=13.4 Hz), 5.06 (2H, s), 5.03 (1H, d, J=12.2 Hz), 4.89 (1H, m), 3.96 (1H, dd, J=8.6, 5.5 Hz), 3.04 (2H, m), 2.12 (1H, m), 0.87 (3H, d, J=6.7 Hz), 0.74 (3H, d, J=6.7 Hz).

13C-NMR (CDCl₃) δ: 178.29, 170.94, 170.38, 154.71, 145.02, 143.71, 140.75, 135.64, 135.01, 134.57, 133.09, 130.93, 129.53, 129.18, 128.99, 128.92, 128.74, 128.47, 128.36, 128.34, 126.94, 67.03, 60.35, 59.08, 53.02, 37.65, 30.40, 19.01, 17.15.

HRMS (FAB) calcd for $C_{38}H_{36}N_2O_8S$ (M⁺+Na) 703.2090; found: 703.2092

Example I-2

Photodissociation Reaction of Protected Amine

The protected amine obtained in Example 1 was irradiated with light. To monitor the reaction by ¹H-NMR, deuterated methanol was added to the solution to adjust the concentration thereof to $2\times10^{-2}$ M. Subsequently, the resulting solution was freeze-deaerated, and transferred to an NMR tube. A super-high pressure mercury lamp was used with a Pyrex® filter to filter out wavelengths of 280 nm or less, and light irradiation was performed at room temperature. The table below shows the results.

[Chem. 67]

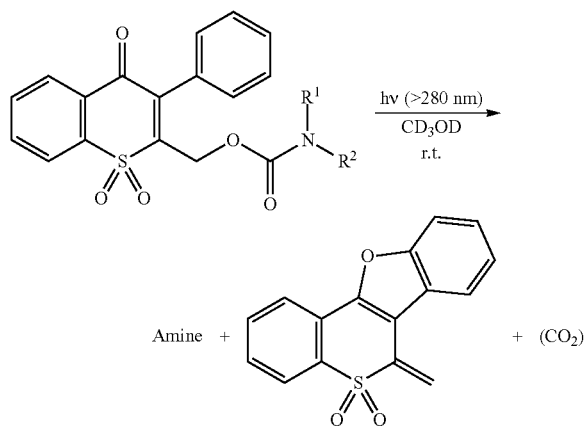

TABLE 1

| Entry | Substrate —NR¹R² | Irradiation Time (h) | Amine | Yield (%)ᵃ |
|---|---|---|---|---|
| 1 | —NHCH₂CH₂CH₂CH₃ | 1.0 | (n-butyl)NH₂ | 97 |
| 2 | —N(CH₂CH₃)₂ | 0.5 | Et₂NH | 98 |
| 3 | —NH[(L)—CH(Bn)COOBn] | 1.0 | BnO-CO-CH(NH₂)-CH₂-Ph | 97 |

ᵃdetermined by ¹H-NMR

With respect to Entry 3, ¹H-NMR (CD₃OD) was measured at the irradiation time of 0 min and after 60-min irradiation, and the progress of the photodissociation reaction was monitored. FIG. 1 shows the results. At the light irradiation time of 0 min, the 2H peak of allylic position derived from the protecting group was observed near 4.6 ppm. However, the peak near 4.6 ppm disappeared after 60-min light irradiation, and along therewith, the 2H peak of olefin derived from a tetracyclic compound was observed. Further, 1H of the triplet near 4.2 ppm shifted to 3.6 ppm, i.e., to the higher magnetic field side; therefore, it was confirmed that the benzyl ester of phenylalanine was prepared in the photodissociation reaction.

Example I-3

Photodissociation Reaction of Protected Amine

The concentration of the solution of the protected product (0.02 mmol, 12 mg) of Entry 3 was adjusted to $2\times10^{-2}$ M with methanol. Subsequently, the resulting solution was freeze-deaerated, and then transferred to a nitrogen-purged reaction tube made of Pyrex®. Using a super-high pressure mercury lamp, light irradiation was performed for 90 min. After the light irradiation, methanol was evaporated under reduced pressure. The residue was purified by silica gel column chromatography, and phenylalanine benzyl ester (0.018 mmol, 4 mg) was obtained in 94%.

Example I-4

Monitoring Reaction using Ultraviolet Visible Spectrum and Fluorescence Spectrum The concentration of the solution of the protected product (0.008 mmol, 5 mg) of Entry 3 was adjusted to $1\times10^{-5}$ M with methanol. Subsequently, the resulting solution was freeze-deaerated, and then transferred to a nitrogen-purged quartz cell (cell length: 1 cm). Using a super-high pressure mercury lamp, only light with a wavelength of 313 nm was irradiated through a monochromator.

The reaction was monitored by ultraviolet-visible spectrum (FIG. 2) and fluorescence spectrum (FIG. 3) at the light irradiation times of 0, 2, 4, 6, 10, 14, 20, 28, and 40 min.

With reference to FIG. 2, the ultraviolet-visible absorption spectra were measured, and the following were confirmed: the absorbance near 350 nm was 0.02 at the light irradiation time of 0 min; the absorbance was 0.04 after 2-min light irradiation; the absorbance was 0.06 after 4-min light irradiation; the absorbance was 0.08 after 6-min light irradiation; the absorbance was 0.09 after 10-min light irradiation; the absorbance was 0.10 after 14-min light irradiation; the absorbance was 0.11 after 20-min light irradiation; the absorbance was 0.115 after 28-min light irradiation; and the absorbance was 0.12 after 40-min light irradiation. As is clear from the above, the absorption near 350 nm is increased as the light irradiation time increases. This increase is derived from a tetracyclic compound, and the above spectra almost corresponded to the ultraviolet-visible spectra of a tetracyclic compound, which was separately prepared to contain the same concentration as above, i.e., $1.0 \times 10^{-5}$ M.

With reference to FIG. 3, a fluorometric analysis was conducted at an excitation wavelength of 365 nm. Since no change was observed in fluorescence intensity between the light irradiation time of 40 min and 60 min, the measurement was finished after 40-min light irradiation. The fluorescence intensity at 444 nm was 4.4 at the light irradiation time of 0 min, and 751 after 40-min irradiation time. The fluorescence emitted after the photodissociation reaction was about 187 times that of the fluorescence emitted before initiation of the reaction. This proves that the release of amine induced by the photodissociation reaction of protected amine can be detected with high sensitivity.

Example I-5

Peptide Synthesis using Photolabile Protecting Group (1) A compound (0.24 mmol, 121 mg) that is prepared by reacting the compound obtained in Production Example 1(5) with t-butyl ester of L-valine was dissolved in trifluoroacetic acid (7 mL) and methylene chloride (10 mL), and the resulting solution was stirred for 10 min at 0° C. The temperature of the solution was returned to room temperature, and the solution was stirred for another 2 hours. The solvents were evaporated under reduced pressure, and the disappearance of the tertiary butyl group was confirmed by $^1$H-NMR.

(2) Subsequently, benzyl ester (0.26 mmol, 68 mg) of phenylalanine was dissolved in methylene chloride (5 mL), to which diisopropylcarbodiimide (0.26 mmol, 41 mL) was added at 0° C. The resulting solution was stirred for 10 min, the temperature of the solution was returned to room temperature, and the solution was stirred for another 5 hours. Water was added thereto to terminate the reaction, and the organic substances were extracted with methylene chloride. The obtained organic layer was dried over magnesium sulfate, and the solvents were evaporated under reduced pressure. The residue was purified by silica gel column chromatography, and the dipeptide (valine-phenylalanine) compound (0.19 mmol, 133 mg) in which the N-terminal was protected was obtained in an 81% yield.

(3) The dipeptide compound in which the N-terminal was protected was subjected to a photodissociation reaction as in Example I-4 to remove the protecting group. Thereby, a dipeptide compound was obtained in a 97% yield.

[Chem. 68]

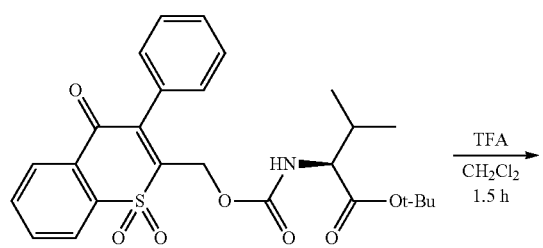

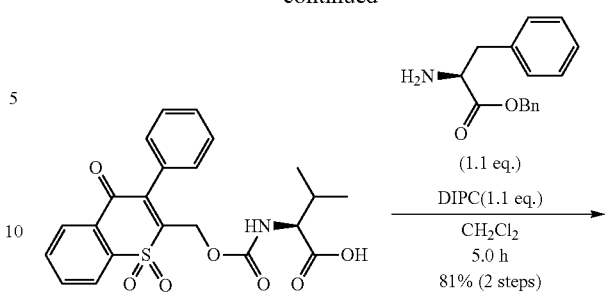

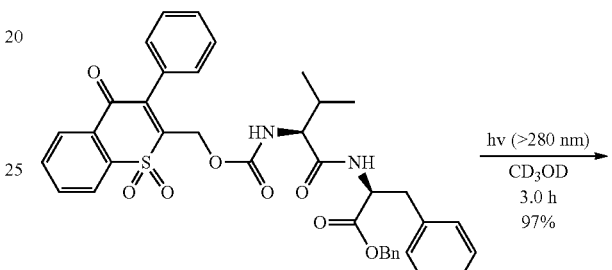

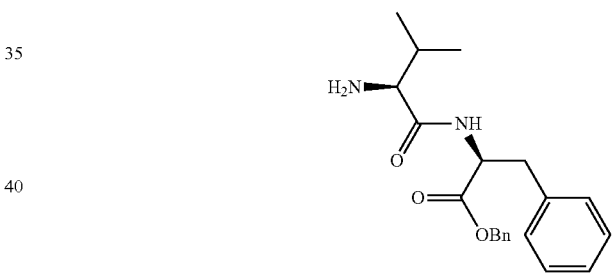

II. Protection and Deprotection of Hydroxyl Group

Example II-1

Under a nitrogen atmosphere, various alcohols (0.1 mmol) were dissolved in methylene chloride (1.0 mL) and pyridine (1.0 mL), to which the compound (1.5 mmol) obtained in Production Example 1(5), which had been dissolved in 0.5 mL of methylene chloride, was added dropwise at 0° C., and the resulting solution was stirred at room temperature for 3 hours. After the reaction product was confirmed by thin-layer chromatography, water was added thereto to terminate the reaction. Then, the organic substances were extracted with methylene chloride, the obtained organic layer was dried over magnesium sulfate, and the solvents were evaporated under reduced pressure. The residue was purified by silica gel column chromatography, and the carbonate compounds shown below were obtained.

57

Ethyl-(4-oxo-3-phenyl-4H-sulfonylchromen-2-yl)methyl carbonate

[Chem. 69]

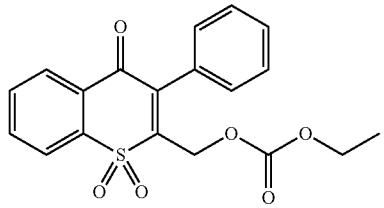

Yield: 98%

Yellow Solid $^1$H-NMR (CDCl$_3$/TMS) (ppm) δ: 8.11 (1H, J=8.0 Hz, d), 8.04 (1H, J=8.0 Hz, d), 7.83 (1H, J=8.0, 8.0 Hz, dd), 7.70 (1H, J=8.0, 8.0 Hz, dd), 7.41-7.19 (3H, m), 5.02 (2H, s), 4.12 (2H, J=7.3 Hz, q), 1.24 (3H, J=7.3 Hz). $^{13}$C-NMR (CDCl$_3$) δ: 178.45, 154.100, 144.768, 144.12, 140.53, 134.77, 133.26, 130.67, 129.74, 129.07, 128.94, 128.92, 128.48, 123.19, 64.87, 60.52, 14.18. IR (CHCl$_3$) 1798, 1751, 1669, 1589, 1465, 1378, 1314, 1285, 1222, 1209, 1164, 1140, 1095, 997, 919, 791, 759, 727, 650, 542.

HRMS (FAB) calcd for C$_{19}$H$_{16}$O$_6$S (M+Na)$^+$ 495.0565; found: 495.0571.

Octyl (4-oxo-3-phenyl-4H-sulfonylchromen-2-yl)methyl carbonate

[Chem. 70]

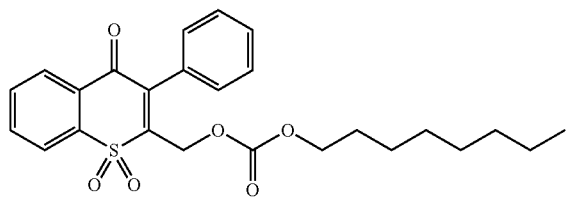

Yield: 76%

Yellow Solid $^1$H-NMR (CDCl$_3$/TMS) (ppm) δ: 8.18 (1H, J=8.0 Hz, d), 8.11 (1H, J=8.0 Hz, d), 7.89 (1H, J=8.0, 8.0 Hz, dd), 7.78 (1H, J=8.0, 8.0 Hz, dd), 7.49-7.48 (3H, m), 7.30-7.26 (2H, m), 5.10 (2H, s), 4.14 (2H, J=6.7 Hz, t), 1.68-1.63 (2H, m), 1.34-1.27 (m, 10H), 0.88 (3H, J=6.8 Hz, t). $^{13}$C-NMR (CDCl$_3$) δ: 178.49, 154.27, 144.79, 144.20, 140.58, 134.80, 133.28, 130.71, 120.65, 129.77, 129.11, 128.98, 128.95, 128.50, 123.24, 69.08, 31.75, 29.13, 28.55, 25.57, 22.62, 14.09. IR (CHCl$_3$) 2958, 2929, 2852, 1756, 1669, 1589, 1493, 1466, 1463, 1397, 1362, 1335, 1256, 1223, 1231, 1208, 1163, 1140, 1123, 1071, 1030, 949, 850, 790, 778, 770, 759, 743, 735, 727, 725, 699.

HRMS (FAB) calcd for C$_{25}$H$_{28}$O$_6$S (M$^+$+Na) 479.1507; found: 479.1502.

58

Benzyl (4-oxo-3-phenyl-4H-sulfonylchromen-2-yl)methyl carbonate

[Chem. 71]

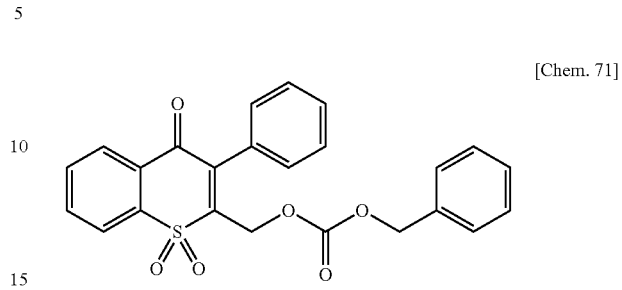

Yield: 58%

Yellow Solid $^1$H-NMR (CDCl$_3$/TMS) δ: 8.19 (1H, d, J=7.9 Hz), 8.12 (1H, d, J=7.9 Hz), 7.90 (1H, dd, J=7.9, 7.9 Hz), 7.78 (1H, dd, J=7.9, 7.9 Hz), 7.48-7.43 (3H, m), 7.37-7.34 (4H, m), 7.27-7.26 (3H, m), 5.17 (2H, s), 5.11 (2H, s). $^{13}$C-NMR (CDCl$_3$) δ: 178.48, 154.10, 145.00, 144.00, 140.53, 134.81, 133.31, 130.64, 129.79, 129.09, 128.97, 128.63, 128.58, 128.53, 128.50, 128.36, 126.99, 123.26, 70.33, 60.71. IR (CHCl$_3$) 2546, 2253, 1794, 1752, 1669, 1465, 1382, 1315, 1267, 1223, 1208, 1164, 1127, 1096, 903, 792, 781, 728, 716, 650, 620.

HRMS (FAB) calcd for C$_{24}$H$_{18}$O$_6$S (M$^+$+Na) 457.0724; found: 457.0719.

Isopropyl (4-oxo-3-phenyl-4H-sulfonylchromen-2-yl)methyl carbonate

[Chem. 72]

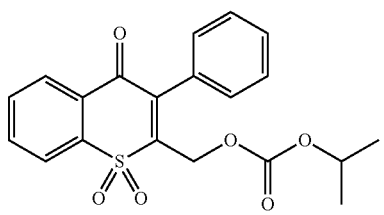

Yield: 67%

Yellow Solid $^1$H-NMR (CDCl$_3$/TMS) δ: 8.18 (1H, d, J=7.9 Hz), 8.11 (1H, d, J=7.9 Hz), 7.89 (1H, dd, J=7.9, 7.9 Hz), 7.78 (1H, dd, J=7.9, 7.9 Hz), 7.50-7.47 (3H, m), 7.30-7.29 (2H, m), 5.09 (2H, s), 4.88 (1H, sept. J=6.1 Hz), 1.30 (6H, d, J=6.1 Hz). $^{13}$C-NMR (CDCl$_3$) δ: 178.46, 153.62, 144.65, 144.29, 140.57, 134.76, 133.24, 130.70, 129.70, 129.07, 128.93, 128.90, 128.45, 123.20, 73.11, 60.27, 21.67. IR (CHCl$_3$) 1744, 1663, 1589, 1467, 1443, 1373, 1365, 1267, 1223, 1210, 1208, 1163, 1141, 1123, 1092, 942, 910, 853, 833, 799, 774, 757, 744, 739, 727, 699, 669.

HRMS (FAB) calcd for C$_{20}$H$_{18}$O$_6$S (M$^+$+Na) 409.0724; found: 409.0722.

Cyclohexyl (4-oxo-3-phenyl-4H-sulfonylchromen-2-yl)methyl carbonate

[Chem. 73]

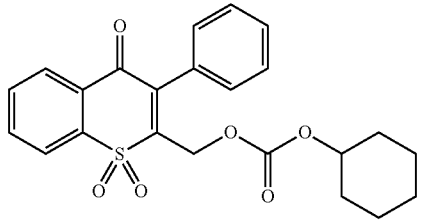

Yield: 53%
Yellow Solid $^1$H-NMR (CDCl$_3$/TMS) δ: 8.19 (1H, d, J=7.9 Hz), 8.12 (1H, d, J=7.9 Hz), 7.90 (1H, dd, J=7.6, 7.9 Hz), 7.78 (1H, dd, J=7.3, 7.9 Hz), 7.49-7.47 (3H, m), 7.31-7.30 (2H, m), 5.09 (2H, s), 4.62-4.60 (1H, m), 1.91-1.89 (2H, m), 1.75-1.73 (2H, m), 1.58-1.50 (3H, m), 1.33-1.28 (3H, m). $^{13}$C-NMR (CDCl$_3$) δ: 178.48, 153.67, 144.62, 144.38, 140.61, 134.78, 133.26, 130.75, 129.73, 129.10, 128.94, 128.92, 128.49, 123.23, 77.89, 60.34, 31.42, 25.15, 23.60. IR (CHCl$_3$) 1745, 1669, 1583, 1444, 1332, 1315, 1272, 1256, 1222, 1208, 1165, 1140, 1126, 1070, 1033, 1005, 981, 850, 789, 781, 757, 747, 727, 699, 669.

HRMS (FAB) calcd for C$_{23}$H$_{22}$O$_6$S (M$^+$+Na) 449.1035; found: 449.1026.

(1R,2S,5R)-2-Isopropyl-5-methylcyclohexyl-(4-oxo-3-phenyl-4H-sulfonylchromen-2-yl)methyl carbonate

[Chem. 74]

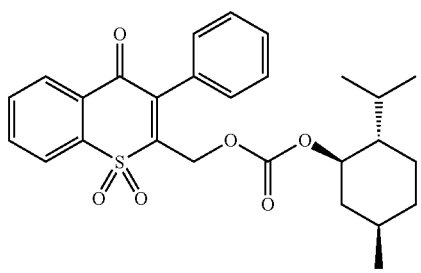

Yield: 30%
Yellow Solid $^1$H-NMR (CDCl$_3$/TMS) δ: 8.18 (1H, d, J=7.9 Hz), 8.11 (1H, d, J=7.9 Hz), 7.88 (1H, dd, J=7.9, 7.9 Hz), 7.77 (1H, dd, J=7.9, 7.9 Hz), 7.47-7.45 (3H, m), 7.30-7.30 (2H, m), 5.12 (1H, d, J=12.8 Hz), 5.04 (1H, d, J=12.8 Hz), 4.51 (1H, td, J=11.0, 4.3 Hz), 2.07-2.05 (1H, m), 1.97-1.96 (1H, m), 1.68-1.66 (2H, m), 1.44-1.42 (2H, m), 1.09-1.00 (2H, m), 0.92-0.88 (6H, m), 0.78 (3H, d, J=6.7 Hz). $^{13}$C-NMR (CDCl$_3$) δ: 178.43, 153.81, 144.60, 144.31, 140.56, 134.70, 133.17, 130.71, 129.64, 129.03, 128.89, 128.83, 128.39, 123.19, 79.46, 60.25, 46.77, 40.44, 33.97, 31.31, 25.88, 23.23, 21.88, 20.62, 16.19. IR (CHCl$_3$) 1745, 1668, 1589, 1444, 1372, 1314, 1265, 1222, 1212, 1208, 1163, 1140, 1071, 951, 913, 847, 787, 785, 781, 779, 777, 775, 769, 767, 763, 758, 747, 738, 731, 699.

HRMS (ESI) calcd for C$_{27}$H$_{30}$O$_6$S (M-H)$^-$481.1684; found: 481.1685.

(3S,9S,10R,13S,14S)-10,13-Dimethyl-17-oxo-2,3,4,7,8,9,10,11,12,13,14,15,16,17-tetradecahydro-1H-cyclopenta[a]phenanthren-3-yl-(4-oxo-3-phenyl-4H-sulfonylchromen-2-yl)methyl carbonate

[Chem. 75]

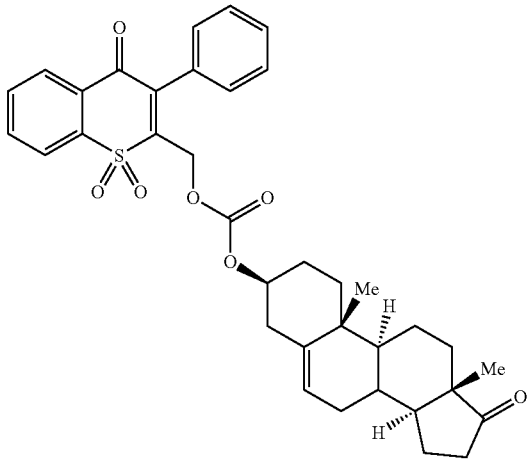

Yield: 23%
Yellow Solid $^1$H-NMR (CDCl$_3$/TMS) δ: 8.07 (1H, d, J=7.9 Hz), 8.00 (1H, d, J=7.9 Hz), 7.79 (1H, dd, J=7.9, 7.9 Hz), 7.68 (1H, dd, J=7.9, 7.9 Hz), 7.39-7.38 (3H, m), 7.22-7.20 (2H, m), 5.33 (1H, d, J=4.9 Hz), 5.00 (2H, s), 4.38 (1H, td, J=11.0, 5.5 Hz), 2.39-2.28 (3H, m), 2.03-1.95 (2H, m), 1.85-1.76 (4H, m), 1.61-1.55 (4H, m), 1.43-1.39 (2H, m), 1.20-1.18 (2H, m), 1.05-1.02 (1H, m), 0.92 (3H, s), 0.79 (3H, s). $^{13}$C-NMR (CDCl$_3$) δ: 178.22, 153.30, 144.39, 144.04, 140.35, 139.27, 134.63, 133.11, 130.57, 129.51, 128.93, 128.71, 128.69, 128.27, 122.96, 122.07, 78.38, 77.21, 60.30, 53.36, 51.43, 49.84, 47.27, 37.62, 36.53, 36.44, 35.60, 31.21, 31.18, 30.54, 27.29, 21.65, 20.11, 19.09, 13.34. IR (CHCl$_3$) 1736, 1669, 1589, 1467, 1443, 1375, 1314, 1267, 1252, 1221, 1219, 1210, 1164, 1140, 1070, 1020, 970, 943, 906, 850, 788, 769, 757, 751, 741, 732, 727, 669.

HRMS (ESI) calcd for C$_{36}$H$_{38}$O$_7$S (M-H)$^-$613.2259; found: 613.2260.

(2S,3R,4S,5R,6R)-2-Methoxy-6-((((4-oxo-3-phenyl-4H-sulfonylchromen-2-yl)methoxy)carbonyloxy)methyl)tetrahydro-2H-pyrane-3,4,5-triyl triacetate

[Chem. 76]

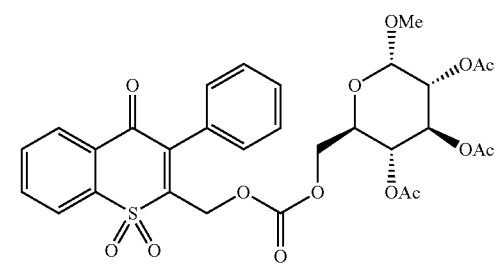

Yield: 46%
Yellow Solid $^1$H-NMR (CDCl$_3$/TMS) δ: 8.18 (1H, d, J=7.9 Hz), 8.07 (1H, d, J=7.9 Hz), 7.89 (1H, dd, J=7.9, 7.9 Hz), 7.78 (1H, dd, J=7.9, 7.9 Hz), 7.50-7.49 (3H, m), 7.29-7.28 (3H, m), 5.56 (1H, dd, J=9.8, 9.8 Hz), 5.20 (1H, d, J=12.8 Hz), 5.05 (1H, d, J=12.8 Hz), 4.97 (2H, d, J=10.4 Hz), 4.93 (2H, d, J=3.7 Hz), 4.88 (1H, dd, J=10.4, 3.7 Hz), 4.29 (1H, dd, J=12.5, 4.6 Hz), 4.19 (1H, dd, J=12.5, 2.4 Hz), 4.04-4.02 (1H, m), 3.40 (3H, s), 2.09 (3H, s), 2.07 (3H, s), 2.02 (3H, s). $^{13}$C-NMR (CDCl$_3$) δ: 178.35, 170.58, 170.15, 169.89, 153.31, 144.72, 143.54, 140.53, 134.78, 133.26, 130.51, 129.81, 129.16, 128.94, 128.91, 128.53, 123.13, 96.71, 73.15, 70.90, 69.39, 66.74, 61.84, 61.37, 55.46, 20.73, 20.70, 20.68. IR (CHCl$_3$) 1756, 1669, 1463, 1371, 1316, 1268, 1237, 1223, 1208, 1166, 1140, 1096, 1070, 1034, 902, 792, 769, 756, 742, 719, 669.

HRMS (FAB) calcd for $C_{30}H_{30}O_{14}S$ (M$^+$+Na) 669.1254; found: 669.1245.

Example II-2

(1) 4-Hydroxybutyl(4-oxo-3-phenyl-4H-thiochromen-2-yl)methyl carbonate

[Chem. 77]

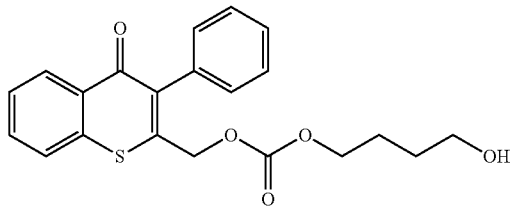

Under a nitrogen atmosphere, 1,4-butanediol (2.0 mmol, 180 mg) was dissolved in 2.0 mL of pyridine, to which the compound (0.2 mmol, 72 mg) obtained in Production Example 1(4), which had been dissolved in methylene chloride, was added dropwise at 0° C. The temperature of the solution was returned to room temperature, and the solution was stirred for 3 hours. After the disappearance of the starting materials was confirmed by thin-layer chromatography, the reaction was terminated by the addition of a saturated ammonium chloride solution. The organic substances were extracted with methylene chloride, the obtained organic layer was dried over magnesium sulfate, and the solvents were evaporated under reduced pressure. Then, the residue was purified by silica gel chromatography, and a monocarbonate compound (0.12 mmol and 46 mg) was obtained in a 58% yield.

Yellow Solid $^1$H-NMR (CDCl$_3$/TMS) δ: 8.51 (1H, d, J=7.3 Hz), 7.64-7.63 (2H, m), 7.56-7.53 (1H, m), 7.47-7.46 (2H, m), 7.41-7.40 (1H, m), 7.24-7.23 (2H, m), 5.01 (2H, s), 4.22 (2H, t, J=6.7 Hz), 3.69 (2H, J=6.4 Hz), 1.83-1.77 (1H, m), 1.69-1.63 (2H, m). $^{13}$C-NMR (CDCl$_3$) δ: 179.23, 154.43, 145.31, 136.59, 136.19, 134.70, 131.60, 131.03, 129.55, 129.39, 128.70, 128.32, 127.82, 126.43, 68.71, 66.82, 62.24, 28.78, 25.13. IR (CHCl$_3$) 1794, 1748, 1700, 1652, 1616, 1464, 1381, 1224, 1221, 1219, 1217, 1215, 1214, 1211, 1206, 1096, 916, 795, 791, 790, 788, 787, 785.

HRMS (FAB) calcd for $C_{21}H_{20}O_5S$ (M$^+$+H) 385.1110; found: 385.1108.

(2) Synthesis of Dicarbonate Compound

[Chem. 78]

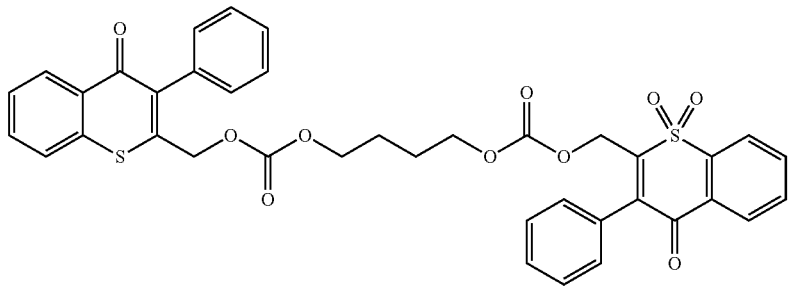

The monocarbonate compound (40 mg, 0.1 mmol) obtained in (1) above was dissolved in 1.0 mL of pyridine, to which the compound (0.5 mmol, 165 mg) obtained in Production Example 1(5), which had been dissolved in methylene chloride, was added dropwise at 0° C. The temperature of the solution was returned to room temperature, and the solution was stirred for 3 hours. The reaction was terminated by the addition of a saturated ammonium chloride solution, and the organic substances were extracted with methylene chloride. The obtained organic layer was dried over magnesium sulfate, and the solvents were evaporated under reduced pressure. The residue was purified by silica gel column chromatography, and the title compound (0.045 mmol, 32 mg) was obtained in a 45% yield.

Yellow Solid $^1$H-NMR (CDCl$_3$/TMS) δ: 8.50 (1H, d, J=7.3 Hz), 8.18 (1H, d, J=7.9 Hz), 8.10 (1H, d, J=7.9 Hz), 8.10 (1H, d, J=7.9 Hz), 7.89 (1H, dd, J=7.9, 7.9 Hz), 7.78 (1H, dd, J=7.9, 7.9 Hz), 7.65-7.61 (2H, m), 7.55-7.52 (1H, m), 7.49-7.44 (5H, m), 7.41-7.39 (1H, m), 7.30-7.28 (2H, m), 7.23-7.23 (2H, m), 5.10 (2H, s), 5.00 (2H, s), 4.20-4.19 (4H, m), 1.79-1.78 (4H, m). $^{13}$C-NMR (CDCl$_3$) δ: 179.17, 178.40, 154.32, 154.12, 145.26, 144.72, 144.03, 140.53, 136.53, 136.15, 134.79, 134.66, 133.28, 131.57, 130.98, 130.66, 129.77, 129.51, 129.32, 129.06, 128.93, 128.67, 128.49, 128.29, 127.77, 126.45, 123.17, 68.03, 66.81, 60.75, 31.55, 24.97, 24.94, 22.62. IR (CHCl$_3$) 1752, 1669, 1620, 1592, 1442, 1315, 1243, 1223, 1217, 1211, 1208, 1163, 1031, 791, 769, 761, 751, 737, 732, 700, 669.

HRMS (FAB) calcd for $C_{38}H_{30}O_{10}S_2$(M$^+$+H) 711.1359; found: 711.1367.

(3) 4-Hydroxybutyl(4-oxo-3-phenyl-4H-sulfonyl-chromen-2-yl)methyl carbonate

[Chem. 79]

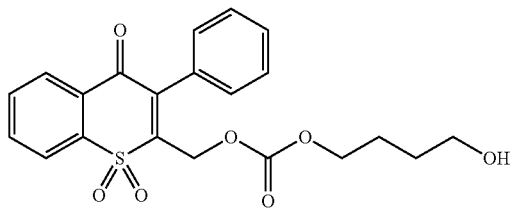

The compound (1.0 mmol) obtained in (1) above and m-chloroperbenzoic acid (70%) (2.1 mmol) were dissolved in methylene chloride (2.0 mL), and the solution was stirred at room temperature for 8 hours. A saturated aqueous sodium thiosulfate solution was poured thereinto to terminate the reaction, and extraction was performed with methylene chloride. Then, the obtained organic layer was washed with saturated sodium bicarbonate water, dried over magnesium sulfate, and the solvents were evaporated under reduced pressure. The residue was purified by silica gel column chromatography, and the title compound was obtained (in 85%). Yellow Solid $^1$H-NMR (CDCl$_3$/TMS) δ: 8.19 (1H, d, J=7.9 Hz), 8.11 (1H, d, J=7.9 Hz), 7.90 (1H, dd, J=7.9, 7.9 Hz), 7.78 (1H, dd, J=7.9, 7.9 Hz), 7.49-7.48 (3H, m), 7.30-7.29 (2H, m), 5.10 (2H, s), 4.20 (2H, t, J=6.4 Hz), 3.67 (2H, t, J=6.4 Hz), 1.81-1.75 (2H, m), 1.68-1.62 (2H, m). $^{13}$C-NMR (CDCl$_3$) δ: 178.40, 154.18, 144.71, 144.05, 140.49, 134.79, 133.28, 130.64, 129.75, 129.06, 128.92, 128.48, 123.17, 68.66, 62.16, 60.66, 28.73, 25.00. IR (CHCl$_3$) 1750, 1669, 1589, 1443, 1396, 1314, 1265, 1228, 1224, 1223, 1220, 1217, 1215, 1213, 1210, 1208, 1205, 1163, 1141, 1071, 1031, 851, 802, 800, 795, 793, 791, 790, 788, 783, 780, 777.

HRMS (FAB) calcd for C$_{21}$H$_{20}$O$_7$S (M$^+$+Na) 439.0827; found: 439.0828.

Example II-3

Using methanol as a solvent, the concentration of the solution of the dicarbonate compound (0.045 mmol) shown below was adjusted to $2.0 \times 10^{-2}$ M. The resulting solution was freeze-deaerated, and transferred to a reaction tube made of Pyrex®. After light irradiation was performed for one hour at room temperature using a super-high pressure mercury lamp, the reaction solution was concentrated under reduced pressure. The residue was purified by silica gel column chromatography, and the monocarbonate compound in which only sulfone was deprotected was isolated in 98%. Simultaneously, the tetracyclic compound was isolated in 88%. Further, by using the same process as employed in Example II-2(3), the sulfur atom was oxidized to sulfone. Subsequently, the obtained compound (0.037 mmol) was dissolved in deuterated methanol, and the concentration thereof was adjusted to $2.0 \times 10^{-2}$ M. The resulting solution was freeze-deaerated, and transferred to an NMR tube. After light irradiation was performed for one hour at room temperature using a super-high pressure mercury lamp, $^1$H-NMR confirmed that the target 1,4-butanediol was quantitatively obtained. Further, the reaction solution was concentrated under reduced pressure, and purification was performed to isolate a tetracyclic compound in 85%.

[Chem. 80]

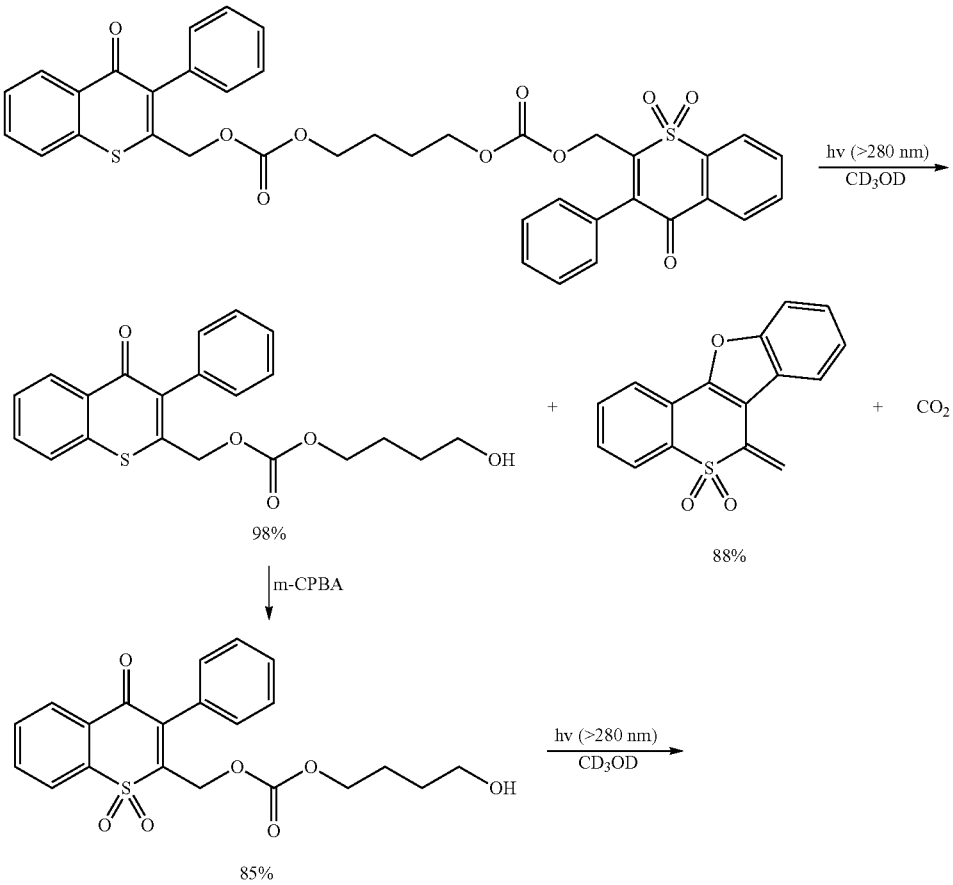

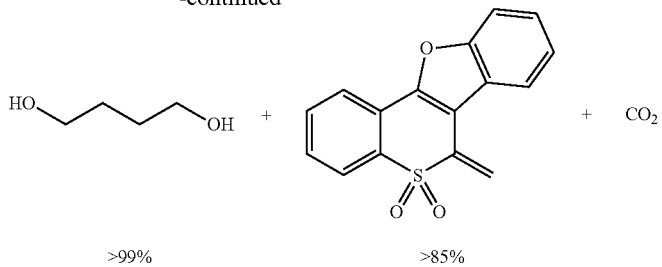

>99%    >85%

III. Protection and Deprotection of Carboxyl Group

Example III-1

Under a nitrogen atmosphere, the compound (1.0 mmol) obtained in Production Example 1(4) was dissolved in 1.0 mL of pyridine, to which various carboxylic acid chlorides (1.5 mmol), which had been dissolved in 1.0 mL of methylene chloride, were added dropwise at 0° C. After completion of the dropwise addition, the temperature of the solution was returned to room temperature, and the solution was stirred for 3 hours. After the disappearance of the starting materials was confirmed by thin-layer chromatography, water was poured thereinto to terminate the reaction. The organic substances were extracted with ethyl acetate, the obtained organic layer was dried over magnesium sulfate, and the solvents were concentrated under reduced pressure. The residue was purified by silica gel chromatography, and the ester compounds shown below were obtained.

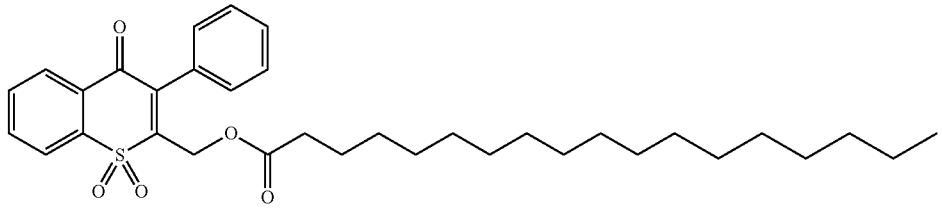

In place of carboxylic acid chloride, a carboxylic acid is used for a condensation reaction with diisopropylcarbodiimide (DIPC) and dimethylaminopyridine (DMAP) to produce an esterified product, similarly to the above. The yields are shown in parentheses.

(4-Oxo-3-phenyl-4H-sulfonylchromen-2-yl)methyl dodecanoate

[Chem. 81]

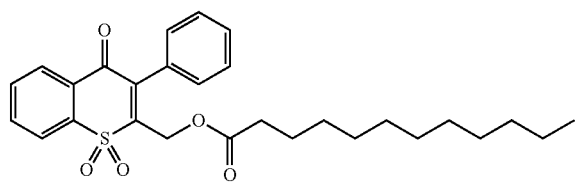

Yield: 87% (81%)

Yellow Solid $^1$H-NMR (CDCl$_3$/TMS) δ: 8.18 (1H, d, J=7.9 Hz), 8.10 (1H, d, J=7.9 Hz), 7.88 (1H, dd, J=7.9, 7.9 Hz), 7.77 (1H, dd, J=7.9, 7.9 Hz), 7.47-7.46 (3H, m), 7.28-7.27 (2H, m), 5.03 (2H, s), 2.34 (2H, t, J=7.3 Hz), 1.61-1.60 (2H, m), 1.28-1.25 (18H, m), 0.88 (3H, t, J=7.0 Hz). $^{13}$C-NMR (CDCl$_3$) δ: 178.44, 172.72, 145.05, 144.31, 140.68, 134.73, 133.24, 130.96, 129.67, 129.02, 129.00, 128.91, 128.45, 123.14, 57.68, 33.90, 31.90, 29.59, 29.43, 29.32, 29.22, 29.05, 24.65, 22.68, 14.13. IR (CHCl$_3$) 1797, 1731, 1669, 1600, 1591, 1460, 1375, 1270, 1221, 1211, 1159, 1140, 1129, 1101, 1072, 909, 865, 785, 770, 768, 755, 745, 730, 727, 669, 650.

HRMS (FAB) calcd for C$_{28}$H$_{35}$O$_4$S (M$^+$+Na) 505.2025; found: 505.2016

(4-Oxo-3-phenyl-4H-sulfonylchromen-2-yl)methyl stearate

[Chem. 82]

Yield: 85% (73%)

Yellow Solid $^1$H-NMR (CDCl$_3$/TMS) δ: 8.19 (1H, d, J=7.9 Hz), 8.11 (1H, d, J=7.9 Hz), 7.89 (1H, dd, J=7.9, 7.9 Hz), 7.78 (1H, dd, J=7.9, 7.9 Hz), 7.47-7.47 (3H, m), 7.28-7.26 (2H, m), 5.03 (2H, s), 2.34 (2H, t, J=7.6 Hz), 1.61-1.60 (2H, m), 1.28-1.25 (28H, m), 0.88 (3H, t, J=6.7 Hz). $^{13}$C-NMR (CDCl$_3$) δ: 178.42, 172.70, 145.04, 144.29, 140.68, 134.70, 133.21, 130.92, 129.65, 129.00, 128.98, 128.90, 128.43, 123.13, 57.66, 33.88, 31.89, 29.67, 29.64, 29.62, 29.57, 29.42, 29.33, 29.20, 29.03, 24.63, 22.66, 14.10. IR (CHCl$_3$) 1794, 1725, 1668, 1602, 1589, 1454, 1379, 1374, 1267, 1222, 1208, 1163, 1140, 1127, 1095, 1071, 911, 863, 787, 776, 765, 758, 745, 730, 726, 669, 650.

HRMS (FAB) calcd for C$_{28}$H$_{35}$O$_4$S (M$^+$+Na) 589.2964; found: 589.2962

(4-Oxo-3-phenyl-4H-sulfonylchromen-2-yl)methyl 2-phenyl acetate

[Chem. 83]

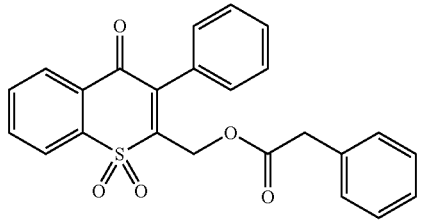

Yield: 80% (78%)
Yellow Solid
$^1$H-NMR (CDCl$_3$/TMS) δ: 8.18 (1H, d, J=7.9 Hz), 8.11 (1H, d, J=7.9 Hz), 7.88 (1H, dd, J=7.9, 7.9 Hz), 7.77 (1H, dd, J=7.9, 7.9 Hz), 7.43-7.41 (1H, m), 7.35-7.33 (4H, m), 7.29-7.25 (3H, m), 7.16-7.15 (2H, m), 5.02 (2H, s), 3.67 (2H, s). $^{13}$C-NMR (CDCl$_3$) 178.35, 170.41, 144.66, 144.52, 140.65, 134.71, 133.24, 133.22, 130.76, 129.62, 129.43, 128.96, 128.90, 128.58, 128.38, 127.24, 123.14, 58.11, 40.85. IR (CHCl$_3$) 1743, 1668, 1589, 1495, 1455, 1443, 1375, 1312, 1264, 1222, 1209, 1162, 1138, 1074, 1030, 1002, 909, 851, 788, 772, 759, 745, 732, 669, 650.
HRMS (FAB) calcd for C$_{24}$H$_{18}$O$_5$S (M$^+$+Na) 441.0773; found: 441.0770.

(4-Oxo-3-phenyl-4H-sulfonylchromen-2-yl)methyl benzoate

[Chem. 84]

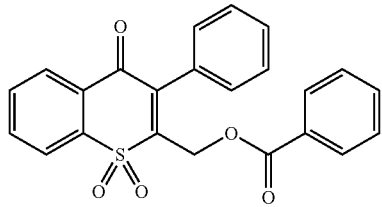

Yield: 92% (76%)
Yellow Solid
$^1$H-NMR (CDCl$_3$/TMS) δ: 8.20 (1H, d, J=7.9 Hz), 8.12 (1H, d, 7.9 Hz), 8.07 (2H, d, J=7.3 Hz), 7.89 (1H, dd, J=7.9, 7.9 Hz), 7.78 (1H, dd, J=7.9, 7.9 Hz), 7.58-7.57 (1H, m), 7.45-7.43 (5H, m), 7.30-7.30 (2H, m), 5.29 (2H, s). $^{13}$C-NMR (CDCl$_3$) δ: 178.50, 165.49, 144.96, 144.48, 140.76, 134.77, 133.44, 133.26, 130.91, 129.97, 129.77, 129.05, 129.03, 129.02, 128.95, 128.57, 128.48, 123.16, 58.59. IR (CHCl$_3$) 1742, 1668, 1589, 1465, 1380, 1313, 1222, 1209, 1162, 1097, 913, 788, 777, 761, 750, 737, 733, 669, 650.
HRMS (FAB) calcd for C$_{23}$H$_{16}$O$_5$S (M$^+$+Na), 427.0616; found: 427.0620.

Example III-2

Photodissociation Reaction of Protected Carboxylic Acid

The protected carboxylic acid obtained in Example III-1 was irradiated with light. To monitor the reaction by $^1$H-NMR, deuterated methanol was added to the solution to adjust the concentration thereof to 2×10$^{-2}$ M. Subsequently, the resulting solution was freeze-deaerated, and transferred to an NMR tube. A super-high pressure mercury lamp was used with a Pyrex® filter to filter out wavelengths of 280 nm or less, and light irradiation was performed at room temperature. The table below shows the results.

[Chem. 85]

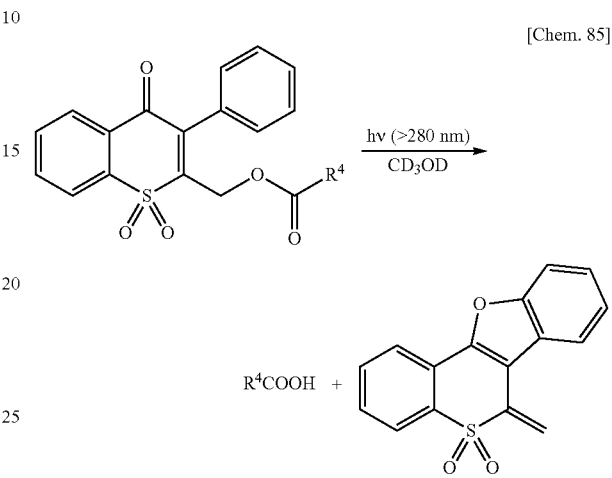

TABLE 2

| Entry | R$^4$COOH | Yield$^a$ |
|---|---|---|
| 1 | C$_{11}$H$_{23}$COOH | >99% |
| 2 | ⟨phenyl⟩—COOH | >99% |
| 3 | C$_{17}$H$_{35}$COOH | >99% |
| 4 | ⟨phenyl⟩—CH$_2$—COOH | >99% |

$^a$determined by $^1$H-NMR

In each reaction, deprotection proceeded in a nearly quantitative yield, giving corresponding carboxylic acids.

With respect to Entry 1, $^1$H-NMR was measured at the light irradiation time of 0 min and after 60-min light irradiation, and the progress of the photodissociation reaction was observed. FIG. 4 shows the results.

With reference to FIG. 4, 2H, S, which is H$_a$, was observed near 5.1 ppm at the light irradiation time of 0 min. However, when light irradiation was performed for 60 min, the reaction solution was concentrated, and NMR was measured, it was confirmed that the signal derived from the protecting group disappeared, and the signal of H$_b$(1H, d), H$_c$(1H, d) of olefin derived from a tetracyclic compound was observed. Further, the methylene proton (2H, dd) near 2.3 ppm derived from carboxylic acid shifted by 0.05 ppm from the starting material side to the higher magnetic field side. Accordingly, it was confirmed that regeneration of carboxylic acid occurred due to the light irradiation.

IV. Protection and Deprotection of Carbonyl Group

Example IV-1

Under a nitrogen atmosphere, the diol compound (0.07 mmol) obtained in Production Example 5(4), p-toluenesulfonic acid (0.007 mmol, 1.2 mg), copper sulfate (0.056 mmol, 8.9 mg) and various ketones (0.077 mmol) were dissolved in benzene, and the resulting solution was stirred at room temperature for 12 hours. After the disappearance of the starting materials was confirmed by thin-layer chromatography, saturated sodium bicarbonate water was added to the solution to terminate the reaction. Then, the organic substances were extracted with ethyl acetate, the obtained organic layer was dried over magnesium sulfate, and the solvents were evaporated under reduced pressure. The residue was purified by silica gel column chromatography, and the acetal compounds shown below were obtained.

2-(2,2-Dimethyl-1,3-dioxolan-4-yl)-3-phenyl-4H-sulfonylchromen-4-one

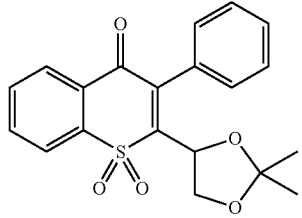

[Chem. 86]

Yield: 95%
White Solid
$^1$H-NMR (CDCl$_3$) δ: 8.13 (1H, d, J=7.9 Hz), 8.09 (1H, d, J=7.9 Hz), 7.88 (1H, dd, J=7.9, 7.9 Hz), 7.74 (1H, dd, J=7.9, 7.9 Hz), 7.48 (3H, m), 7.18 (2H, m), 4.85 (1H, dd, J=7.9, 7.9 Hz), 4.37 (1H, dd, J=7.9, 7.9 Hz), 4.08 (1H, dd, J=7.9, 7.9 Hz), 1.54 (3H, s), 1.32 (3H, s). $^{13}$C-NMR (CDCl$_3$) δ: 178.30, 148.06, 142.68, 142.20, 134.73, 132.89, 131.70, 129.39, 128.69, 128.60, 128.57, 122.95, 111.97, 25.54. IR (CHCl$_3$) 2611, 2253, 1794, 1665, 1466, 1382, 1317, 1223, 1213, 1208, 1154, 1130, 1096, 1064, 912, 789, 777, 764, 749, 732, 727, 718, 670, 668, 650, 620, 542.
HRMS (FAB) calcd for C$_{20}$H$_{18}$O$_5$S (M$^+$+Na), 393.0773; found: 393.0773.

2-(2,2-Diethyl-1,3-dioxolan-4-yl)-3-phenyl-4H-sulfonylchromen-4-one

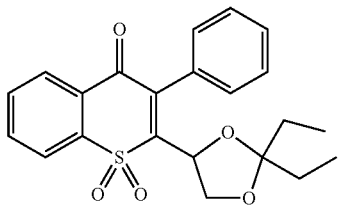

[Chem. 87]

Yield: 88%
White Solid
$^1$H-NMR (CDCl$_3$) δ: 8.13 (1H, d, J=7.9 Hz), 8.09 (1H, d, J=7.9 Hz), 7.87 (1H, t, J=7.9 Hz), 7.74 (1H, t, J=7.9 Hz), 7.48-7.47 (2H, m), 7.21-7.19 (2H, m), 4.76 (1H, dd, J=8.9, 6.4 Hz), 4.40 (1H, dd, J=8.9, 8.9 Hz), 4.05 (1H, dd, J=8.9, 6.4 Hz), 1.82 (2H, q, J=7.6 Hz), 1.58 (2H, q, J=7.6 Hz), 0.99 (3H, t, J=7.6 Hz), 0.78 (3H, t, J=7.6 Hz). $^{13}$C-NMR (CDCl$_3$) δ: 178.31, 147.36, 143.26, 142.26, 134.73, 132.89, 131.71, 129.42, 128.64, 128.58, 128.51, 122.94, 115.85, 74.93, 69.06, 29.01, 28.43, 8.44, 7.77. IR (CHCl$_3$) 2986, 2944, 2640, 2253, 1794, 1666, 1588, 1465, 1380, 1317, 1223, 1216, 1208, 1157, 1130, 1097, 911, 788, 781, 771, 760, 743, 728, 724, 650, 620, 541.

3-Phenyl-2-(1,4-dioxaspiro[4.5]decan-2-yl)-4H-sulfonylchromen-4-one

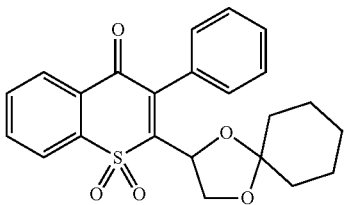

[Chem. 88]

Yield: 70%
White Solid
$^1$H-NMR (CDCl$_3$) δ: 8.14-8.12 (1H, m), 8.10-8.08 (1H, m), 7.88-7.86 (2H, m), 7.74-7.72 (2H, m), 7.48-7.46 (5H, m), 7.20-7.18 (3H, m), 4.85-4.83 (2H, m), 4.38-4.36 (2H, m), 4.09-4.07 (2H, m), 1.71-1.38 (9H, m), 1.71-1.38 (9H, m), 1.71-1.38 (9H, m), 1.71-1.38 (9H, m). $^{13}$C-NMR (CDCl$_3$) δ: 178.31, 148.13, 142.65, 142.25, 134.70, 132.85, 131.74, 129.33, 128.66, 128.58, 128.49, 122.91, 112.65, 74.09, 69.24, 34.98, 34.90, 24.95, 23.78. IR (CHCl$_3$) 1794, 1666, 1588, 1464, 1380, 1317, 1223, 1220, 1209, 1159, 1130, 1097, 905, 788, 778, 771, 758, 749, 741, 727, 721, 650, 620, 540.
HRMS (FAB) calcd for C$_{23}$H$_{22}$O$_5$S (M$^+$+Na), 433.1086; found: 433.1085.

2-(2,2-Diphenyl-1,3-dioxolan-4-yl)-3-phenyl-4H-sulfonylchromen-4-one

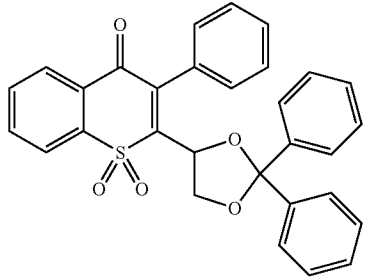

[Chem. 89]

Yield: 10%
White Solid
$^1$H-NMR (CDCl$_3$) δ: 8.11 (2H, dd, J=7.6, 7.6 Hz), 7.87 (1H, dd, J=7.6, 7.6 Hz), 7.74 (1H, dd, J=7.6, 7.6 Hz), 7.51-7.49 (2H, m), 7.43-7.42 (2H, m), 7.37-7.35 (3H, m), 7.29-7.27 (6H, m), 7.21-7.19 (2H, m), 4.88 (1H, dd, J=7.6, 7.6 Hz), 4.64 (1H, dd, J=7.6, 7.6 Hz), 4.05 (1H, dd, J=7.6, 7.6 Hz). $^{13}$C-NMR (CDCl$_3$) δ: 178.64, 147.12, 143.85, 141.87, 140.75, 140.40, 134.70, 133.01, 131.34, 129.37, 128.87, 128.80, 128.66, 128.39, 128.34, 128.28, 128.25, 127.91, 126.76, 126.20, 123.08, 111.74, 73.93, 68.96. IR (CHCl$_3$) 1794, 1667, 1465, 1381, 1317, 1223, 1208, 1159, 1129, 1096, 905, 788, 773, 758, 748, 733, 727, 718, 668, 650, 621, 565, 540, 512.

Example IV-2

The protected carbonyl group obtained in Example IV-1 was irradiated with light. To monitor the reaction by $^1$H-NMR, deuterated methanol was added to the solution to adjust the concentration thereof to $2\times10^{-2}$ M. Subsequently, the resulting solution was freeze-deaerated, and transferred to an NMR tube. A super-high pressure mercury lamp was used with a Pyrex® filter to filter out wavelengths of 280 nm or less, and light irradiation was performed at room temperature. The table below shows the results.

[Chem. 90]

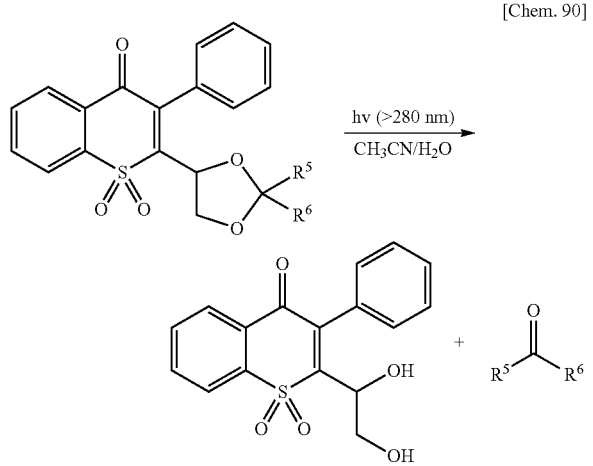

With reference to the table, the photoreaction with regard to the protected acetone (Entry 1) was analyzed. According to the results, $^1$H-NMR confirmed that acetone was obtained in 90%, and a diol product was also regenerated in 91%. With respect to the protected diethyl ketone (Entry 2), diethyl ketone was recovered in 99% and diol product in 94%. These photolabile protecting groups have advantages in that the diol products are regenerated after the reaction, and can be reused.

V. Protection and Deprotection of Aldehyde Group

Example V-1

Under a nitrogen atmosphere, the diol compound (0.3 mmol, 99.1 mg) obtained in Production Example 5(4), p-toluenesulfonic acid (0.03 mmol, 5.7 mg), copper sulfate (0.24 mmol, 38.3 mg) and pivalaldehyde (0.33 mmol, 28.4 mg) were dissolved in benzene (3 mL), and the resulting solution was stirred at room temperature. Three hours later, saturated sodium bicarbonate water was added to the solution to terminate the reaction. The reaction product was extracted with ethyl acetate, and dried over magnesium sulfate. The solvents were evaporated under reduced pressure, and the residue was purified by silica gel column chromatography to obtain the acetal compound shown below.

TABLE 3

| Entry | Substrate | Solvent | Time (h) | Diol | Ketone[a] |
|---|---|---|---|---|---|
| 1 | | CH$_3$CN (1.0 v % H$_2$O) | 3.0 | 91% | 90% |
| 2 | | CH$_3$CN (1.0 v % H$_2$O) | 3.0 | 94% | 99% |
| 3 | | CH$_3$CN (1.0 v % H$_2$O) | 3.0 | 93% | 69% |

[a] determined by $^1$H-NMR

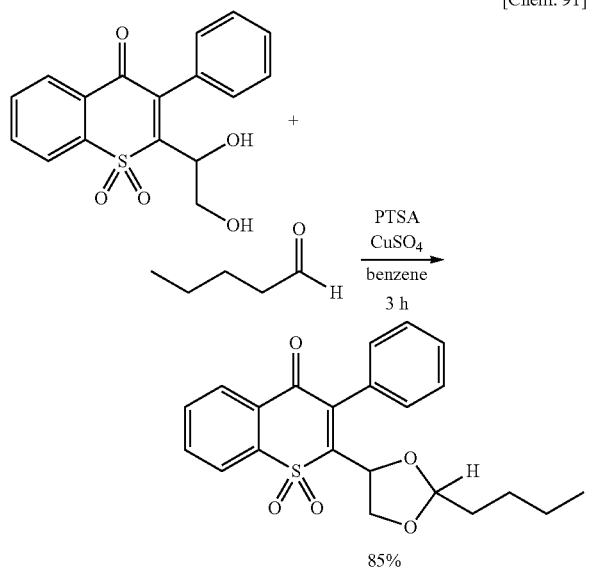

2-(2-Butyl-1,3-dioxolan-4-yl)-3-phenyl-4H-sulfonyl-chromen-4-one

[Chem. 92]

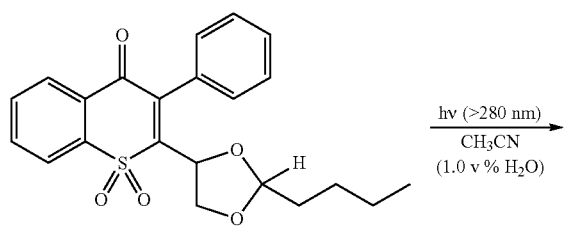

White Solid $^1$H-NMR (CDCl$_3$) δ: 8.10 (1H, J=7.9 Hz, d), 8.07 (1H, J=7.9 Hz, d), 7.85 (1H, J=7.9, 7.9 Hz, dd), 7.74-7.70 (1H, m), 7.47-7.45 (3H, m), 7.16 (2H, m), 5.19, 4.85 (1H, J=4.7, 4.7 Hz, dd), 4.88, 4.81 (1H, J=7.8, 7.8 Hz, dd), 4.33, 4.19, 4.13, 3.97 (1H, J=7.8, 7.8 Hz, dd), 1.75-1.61 (2H, m), 1.44-1.24 (4H, m), 0.92-0.86 (3H, m). $^{13}$C-NMR (CDCl$_3$) δ: 178.26, 178.07, 149.70, 148.44, 142.24, 142.19, 141.91, 141.85, 134.60, 134.57, 132.86, 132.80, 131.64, 131.51, 129.27, 129.18, 128.60, 128.58, 128.51, 128.49, 128.46, 128.41, 128.35, 122.81, 122.78, 106.85, 106.81, 74.14, 73.86, 71.01, 69.92, 33.09, 32.62, 26.22, 25.66, 22.38, 13.84.

HRMS (EI) calcd for C$_{22}$H$_{22}$O$_5$S (M$^+$) 398.1188;. found: 398.1189

Example V-2

Photodissociation Reaction of Protected Aldehyde Group

[Chem. 93]

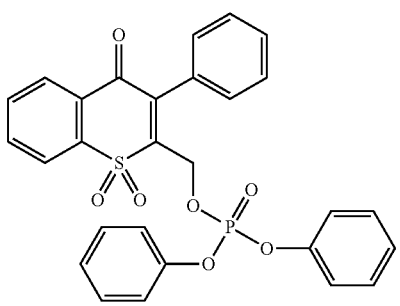

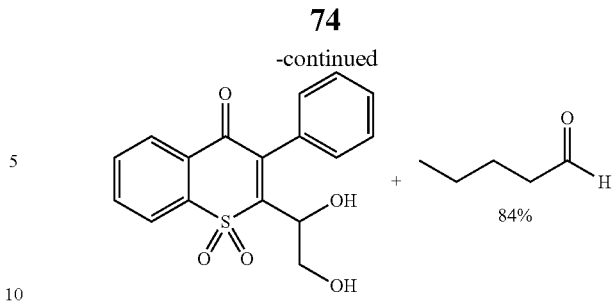

The protected aldehyde group obtained in Example V-1 was irradiated with light. To monitor the reaction by $^1$H-NMR, deuterated methanol was added to the solution to adjust the concentration thereof to $2\times10^{-2}$ M, and deuterated water was further added at a concentration of 1 vol %. Subsequently, the resulting solution was freeze-deaerated, and transferred to an NMR tube. A super-high pressure mercury lamp was used with a Pyrex® filter to filter out wavelengths of 280 nm or less, and light irradiation was performed at room temperature. The table below shows the results. The yield of deprotection was calculated using NMR data; aldehyde was produced in a yield of 84%.

VI. Protection and Deprotection of Phosphodiester

Example VI-1

[Chem. 94]

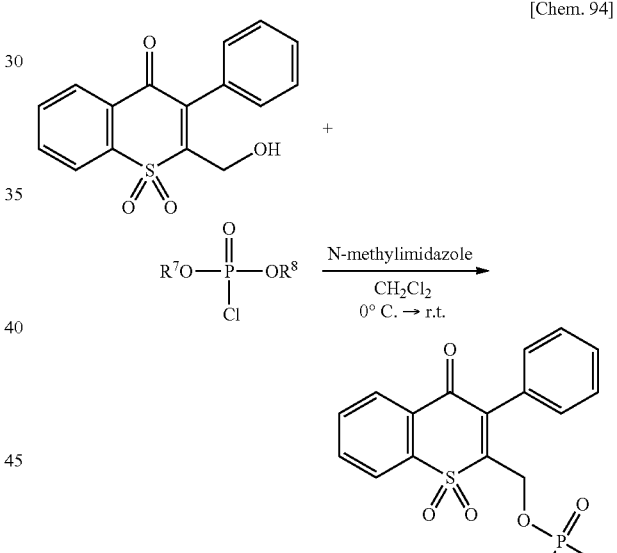

(4-Oxo-3-phenyl-4H-sulfonylchromen-2-yl)methyl diphenyl phosphate

[Chem. 95]

Under a nitrogen atmosphere, chloro diphenyl phosphate (200 mg, 0.8 mmol) was added to methylene chloride (5 mL) and dissolved therein. While cooling the resulting solution at 0° C., a methylene chloride solution (5 mL) of the alcohol compound (300 mg, 1 mmol) obtained in Production Example 1(4) and N-methylimidazole (200 μL, 2.5 mmol) was added dropwise. After completion of the dropwise addition, the solution was stirred for 30 min at room temperature. The resulting solution was then quenched with 1N hydrochloric acid, and extraction was performed with methylene chloride. The extracted product was washed with saturated sodium hydrogen carbonate and a saturated sodium chloride solution, and the obtained organic layer was dried over magnesium sulfate. The solvents were evaporated under reduced pressure, the residue was isolated and purified by flash column chromatography (hexane:ethyl acetate=1:1), and the protected phosphodiester shown above was obtained.
Yield: 93%
Yellow Oil
$^1$H-NMR (CD$_3$OD) δ: 8.09 (1H, J=7.8 Hz, d), 8.06 (1H, J=7.8 Hz, d), 7.91 (1H, J=8.0, 8.0 Hz, dd), 7.78 (1H, J=8.0, 8.0 Hz, dd), 7.37 (1H, J=7.7 Hz, t), 7.32-7.25 (8H, m), 7.17-7.12 (4H, m), 7.08-7.07 (2H, m), 5.07 (2H, J=5.5 Hz, d). $^{13}$C-NMR (CDCl$_3$) δ: 178.59, 150.12, 150.06, 145.68, 143.32, 143.23, 140.17, 134.77, 133.25, 130.24, 129.78, 129.70, 129.67, 129.66, 129.11, 129.04, 128.92, 128.82, 128.35, 125.44, 123.05, 120.11, 120.09, 120.07, 120.04, 120.03, 120.01, 60.23. $^{31}$P-NMR (CD$_3$OD) δ: −14.31.
HRMS (FAB) calcd for C$_{28}$H$_{21}$O$_7$PS (M$^+$-+H) 533.0824; found: 533.0828.

(4-Oxo-3-phenyl-4H-sulfonylchromen-2-yl)methyl diethyl phosphate

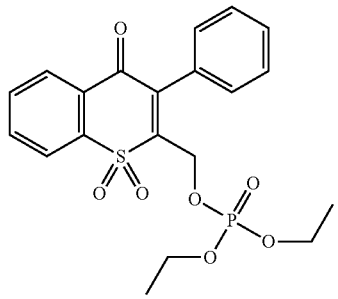

[Chem. 96]

Under a nitrogen atmosphere, chlorodiethylphosphate (17 ®L, 0.08 mmol) was dissolved in methylene chloride (500 μL). While cooling the solution at 0° C., a methylene chloride solution (250 μL) of N-methylimidazole (19 μL, 0.24 mmol) was added dropwise. After 30-min stirring, a methylene chloride solution (250 μL) of the alcohol compound (30 mg, 0.1 mmol) obtained in Production Example 1(4) was further added to the solution dropwise, and stirred at room temperature for 8 hours. The resulting solution was quenched with a saturated aqueous ammonia chloride solution, and extraction was performed with methylene chloride. Then, the extracted product was washed with a saturated sodium chloride solution, and the obtained organic layer was dried over sodium sulfate. The solvents were evaporated under reduced pressure, the residue was isolated and purified by silica gel column chromatography (hexane:ethyl acetate=1:1), and the protected phosphodiester shown above was obtained.
Yield: 73%
Yellow Oil
$^1$H-NMR (500 MHz, CDCl$_3$) δ: 8.19 (1H, d, J=7.8 Hz), 8.12 (1H, d, J=7.8 Hz), 7.91 (1H, dd, J=7.8, 7.8 Hz), 7.79 (1H, dd, J=7.8, 7.8 Hz), 7.50-7.46 (3H, m), 7.32-7.30 (2H, m), 4.96 (2H, d, J$_{PH}$=4.9 Hz), 4.13 (4H, dq, J$_{PH}$=14.5, 7.3 Hz), 1.32 (6H, t, J=7.0 Hz). $^{31}$P-NMR (500 MHz, CDCl$_3$) δ(ppm) −1.99.
HRMS (FAB) calcd for C$_{20}$H$_{21}$O$_7$PS (M$^+$-+Na) 459.0643; found: 459.0638.

Example VI-2

Photodissociation Reaction of Protected Phosphodiester

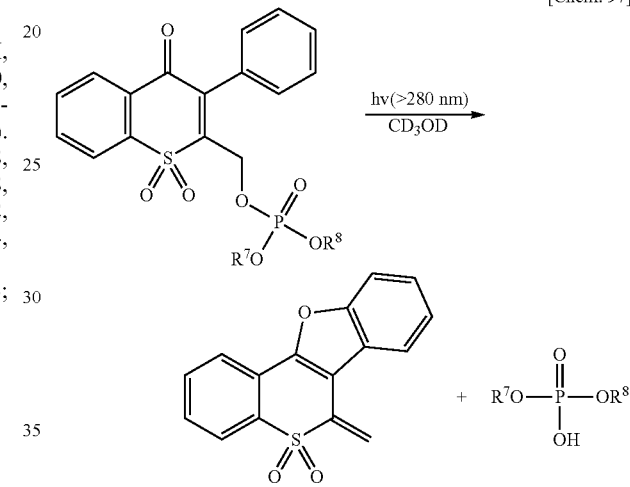

[Chem. 97]

The protected phosphodiester obtained in Example VI-1 was irradiated with light. To monitor the reaction by $^1$H-NMR, deuterated methanol was added to the solution to adjust the concentration thereof to 2×10$^{-2}$ M. Subsequently, the resulting solution was freeze-deaerated, and transferred to an NMR tube. A super-high pressure mercury lamp was used with a Pyrex® filter to filter out wavelengths of 280 nm or less, and light irradiation was performed at room temperature. The yield of deprotection was calculated using NMR data. When the R above was an ethyl group, a phosphoric acid compound was produced in 99%, 1 hour afterward. When the R was a phenyl group, the deprotection reaction was also confirmed to have been proceeded to obtain an isolated yield of 96%.

Figure 1:
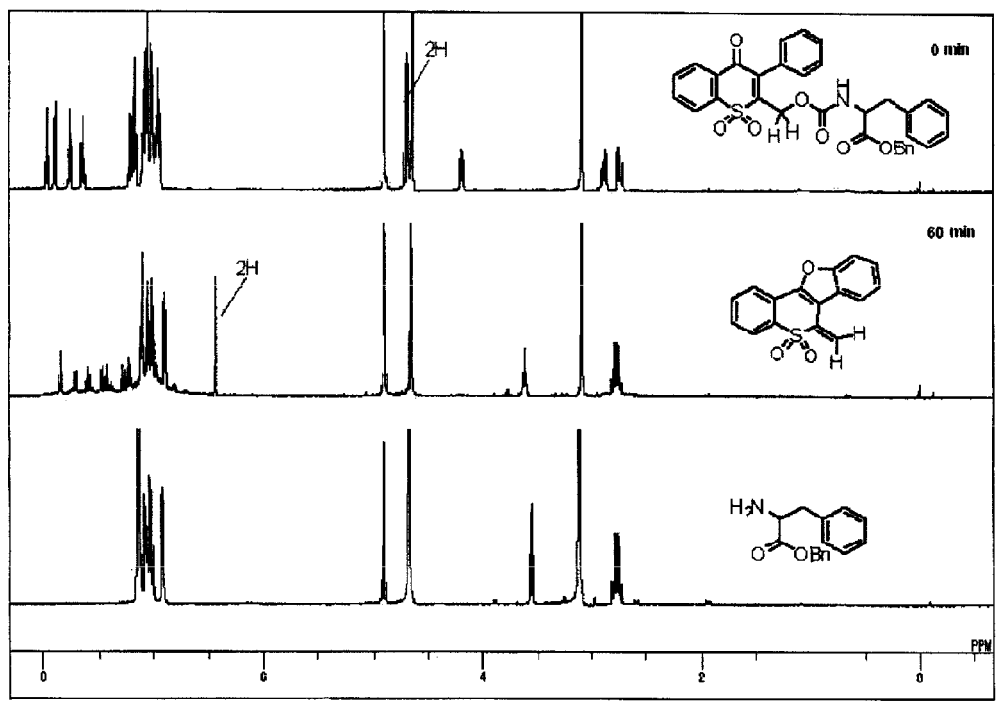
FIG. 1 shows the time course of the photodissociation reaction observed by $^1$H-NMR with regard to the protected amine (Entry 3) of Example I-2.
Figure 2:
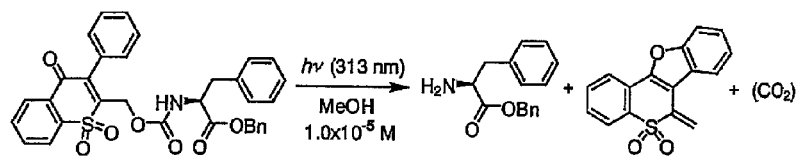
FIG. 2 shows the progress of the reaction observed by ultraviolet visible spectrum with regard to the protected amine (Entry 3) of Example I-4.
Figure 2:
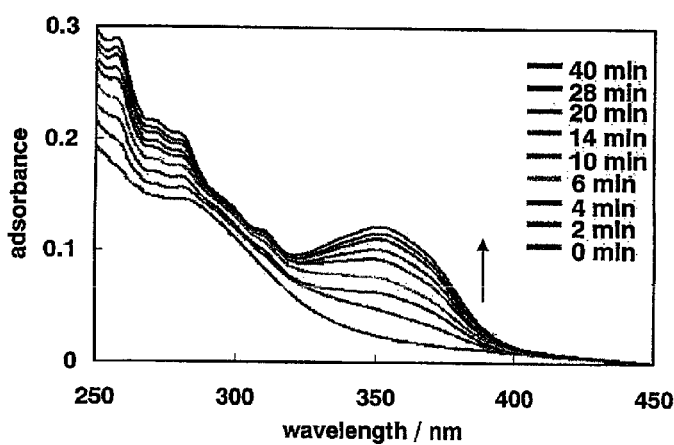
Figure 3:
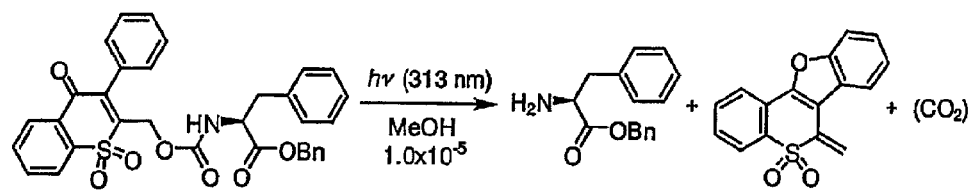
FIG. 3 shows the progress of the reaction observed by fluorescence spectrum with regard to the protected amine (Entry 3) of Example I-4.
Figure 3:
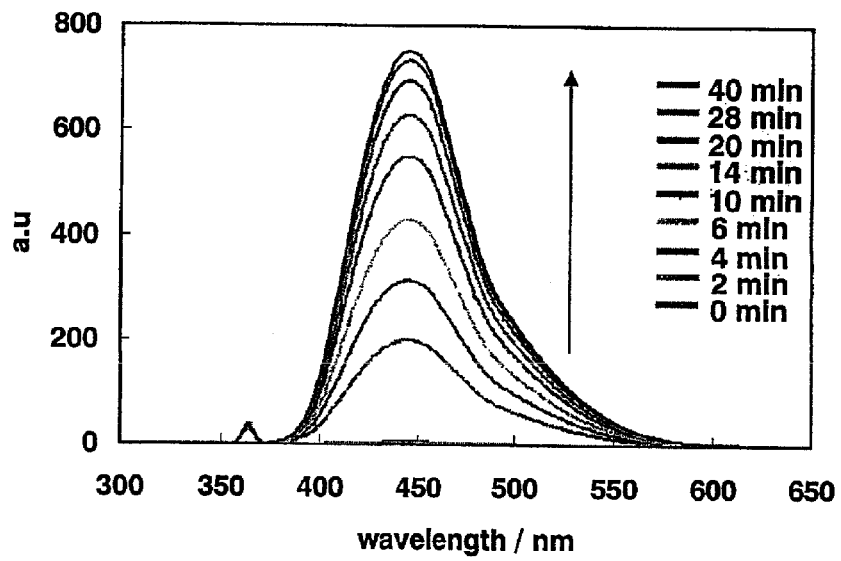
Figure 4:
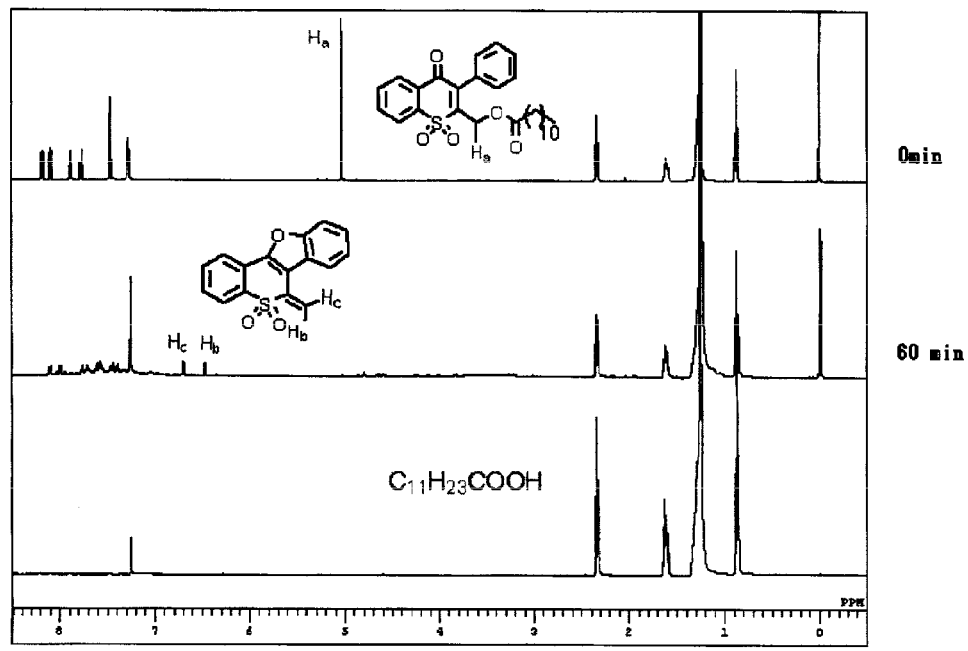
FIG. 4 shows the time course of the photodissociation reaction observed by $^1$H-NMR with regard to the protected carboxylic acid (Entry 1) of Example III-2.

The invention claimed is:

1. A compound represented by Formula (3):

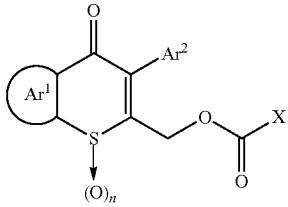
(3)

wherein Ar$^1$ is an optionally substituted aromatic or heteroaromatic ring, Ar$^2$ is an optionally substituted aryl or heteroaryl group, X is a leaving group, and n is an integer of 1 or 2,
wherein the aromatic or heteroaromatic ring of Ar$^1$ is selected from the group consisting of a benzene ring, a naphthalene ring, an anthracene ring, a phenanthrene ring, a fluorene ring, a dibenzo[b,d]furan ring, a pyridine ring, a pyrimidine ring, and a pyrazine ring;
wherein the optionally substituted aromatic ring Ar$^1$ and/or the optionally substituted aryl group Ar$^2$ has one to three substituents selected from the group consisting of an alkyl group, a haloalkyl group, an alkoxy group, a dialkylamino group, a halogen atom, a cyano group, and a nitro group; and
wherein the leaving group X is selected from the group consisting of a halogen atom, an imidazolyl group, and a pentafluorophenyl group.

2. A method of producing a compound represented by Formula (3):

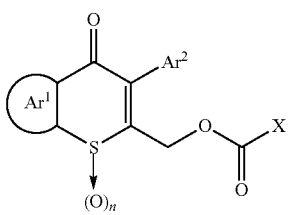
(3)

wherein Ar$^1$ is an optionally substituted aromatic or heteroaromatic ring, Ar$^2$ is an optionally substituted aryl or heteroaryl group, X is a leaving group, and n is an integer of 1 or 2,
wherein the aromatic or heteroaromatic ring of Ar$^1$ is selected from the group consisting of a benzene ring, a naphthalene ring, an anthracene ring, a phenanthrene ring, a fluorene ring, a dibenzo[b,d]furan ring, a pyridine ring, a pyrimidine ring, and a pyrazine ring;
wherein the optionally substituted aromatic ring Ar$^1$ and/or the optionally substituted aryl group Ar$^2$ has one to three substituents selected from the group consisting of an alkyl group, a haloalkyl group, an alkoxy group, a dialkylamino group, a halogen atom, a cyano group, and a nitro group;
wherein the leaving group X is selected from the group consisting of a halogen atom, an imidazolyl group, and a pentafluorophenyl group;
wherein the method comprises reacting a compound represented by Formula (1):

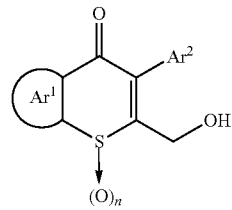
(1)

wherein Ar$^1$, Ar$^2$, and n are as defined above, with a compound represented by Formula (2):

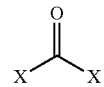
(2)

wherein X are the same or different, and each represent the leaving group as defined above, or an equivalent thereof.

3. A method of protecting an amino group or hydroxyl group, comprising reacting the amino group or hydroxyl group with a compound represented by Formula (3):

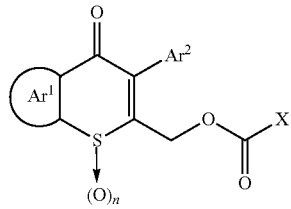
(3)

wherein Ar$^1$ is an optionally substituted aromatic or heteroaromatic ring, Ar$^2$ is an optionally substituted aryl or heteroaryl group, X is a leaving group, and n is an integer of 1 or 2,
wherein the aromatic or heteroaromatic ring of Ar$^1$ is selected from the group consisting of a benzene ring, a naphthalene ring, an anthracene ring, a phenanthrene ring, a fluorene ring, a dibenzo[b,d]furan ring, a pyridine ring, a pyrimidine ring, and a pyrazine ring;
wherein the optionally substituted aromatic ring Ar$^1$ and/or the optionally substituted aryl group Ar$^2$ has one to three substituents selected from the group consisting of an alkyl group, a haloalkyl group, an alkoxy group, a dialkylamino group, a halogen atom, a cyano group, and a nitro group; and
wherein the leaving group X is selected from the group consisting of a halogen atom, an imidazolyl group, and a pentafluorophenyl group.

* * * * *